US008969254B2

(12) United States Patent
Reinherz et al.

(10) Patent No.: US 8,969,254 B2
(45) Date of Patent: Mar. 3, 2015

(54) OLIGONUCLEOTIDE ARRAY FOR TISSUE TYPING

(75) Inventors: Ellis L. Reinherz, Lincoln, MA (US);
Vladimir Brusic, Brookline, MA (US);
Guanglan Zhang, Brighton, MA (US);
Derin Benerci Keskin, Somerville, MA (US); David Deluca, Allston, MA (US);
Honghuang Lin, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/329,161

(22) Filed: Dec. 16, 2011

(65) Prior Publication Data
US 2012/0264627 A1 Oct. 18, 2012

Related U.S. Application Data

(60) Provisional application No. 61/423,991, filed on Dec. 16, 2010.

(51) Int. Cl.
C40B 30/04 (2006.01)
C12Q 1/68 (2006.01)

(52) U.S. Cl.
CPC .................................... *C12Q 1/6881* (2013.01)
USPC ............................................. 506/9; 435/6.11

(58) Field of Classification Search
None
See application file for complete search history.

(56) References Cited

U.S. PATENT DOCUMENTS

| 4,401,796 | A | 8/1983 | Itakura |
|---|---|---|---|
| 4,458,066 | A | 7/1984 | Caruthers et al. |
| 4,500,707 | A | 2/1985 | Caruthers et al. |
| 5,143,854 | A | 9/1992 | Pirrung et al. |
| 5,288,514 | A | 2/1994 | Ellman |
| 5,985,662 | A | 11/1999 | Anderson et al. |
| 6,670,124 | B1 * | 12/2003 | Chow et al. ................... 435/6.12 |
| 2003/0119015 | A1 | 6/2003 | Frazer et al. |
| 2008/0241823 | A1 | 10/2008 | Gut et al. |
| 2009/0099035 | A1 | 4/2009 | Petersdorf et al. |
| 2009/0264307 | A1 | 10/2009 | Gresham et al. |
| 2010/0279889 | A1 | 11/2010 | Mitra et al. |

FOREIGN PATENT DOCUMENTS

| WO | WO 9639154 | 12/1996 | | |
|---|---|---|---|---|
| WO | WO 9703211 | 1/1997 | | |
| WO | WO 98/02749 A1 * | 1/1998 | ........... | G01N 33/576 |
| WO | WO 2007/076577 A1 * | 7/2007 | ............... | C12Q 1/68 |

OTHER PUBLICATIONS

Gresham et al. (2010) "Optimized detection of sequence variation in heterozygous genomes using DNA microarrays with isothermal-melting probes" PNAS 107(4):1482-1487; published online Jan. 8, 2010.*

Avent (2009) "Large-scale blood group genotyping—clinical implications" British Journal of Haematology 144(1):3-13; published online Nov. 4, 2008.*
Saunthararajah et al. (2003) "A simple method to predict response to immunosuppressive therapy in patients with myelodysplastic syndrome" Blood 102(8):3025-3027; published online Jun. 26, 2003.*
John et al. (2005) "Interactive selective pressures of HLA-restricted immune responses and antiretroviral drugs on HIV-1" Antiviral Therapy 10(4):551-555; published 2005.*
Maksymowych et al. "Association of a Specific ERAP1/ARTS1 Haplotype With Disease Susceptibility in Ankylosing Spondylitis" (2009) Arthristis and Rheumatism 60(5):1317-1323; published May 2009.*
Vidal-Castineira et al. (2010) "Effect of killer immunoglobulin-like receptors in the response to combined treatment in patients with chronic hepatitis C virus infection" Journal of Virology 84(1):475-481.*
Authorized Officer J.H. Choi. International Search Report and Written Opinion in International Application No. PCT/US2011/065624, dated Dec. 3, 2012, 14 pages.
Ahlenstiel et al., "Distinct KIR/HLA compound genotypes affect the kinetics of human antiviral natural killer cell responses," *J Clin Invest.*, 2008, 118(3):1017-26.
An and Winkler, "Host genes associated with HIV/AIDS: advances in gene discovery," *Trends Genet*, 2010, 26(3):119-31.
Chen et al., "Activating KIR genes are associated with CMV reactivation and survival after non-T-cell depleted HLA-identical sibling bone marrow transplantation for malignant disorders," *Bone Marrow Transplantation*, 2006, 38:437-444.
De Petris et al., "Correlation between HLA-A2 gene frequency, latitude, ovarian and prostate cancer mortality rates," *Medical Oncology*, 2004, 21(1):49-52.
Geraghty et al., "A human major histocompatibility complex class I gene that encodes a protein with a shortened cytoplasmic segment," *Proc. Natl. Acad. Sci. USA*, 1987, 84:9145-49.
Gonzalez et al., "Killer cell immunoglobulin-like receptor allele discrimination by high-resolution melting," *Hum Immunol.*, 2009, 70(10):858-63.
Gonzalez-Roces et al., "HLA-B27 polymorphism and worldwide susceptibility to ankylosing spondylitis," *Tissue Antigens*, 2008, 49:116-123.
Guo et al., "Direct fluorescence analysis of of genetic polymorphisms by hybridization with oligonucleotide arrays on glass supports," *Nuc. Acids Res.*, 1994, 22:5456-5465.
Khan et al., "Genetics of HLA associated dseases: rheumatoid arthritis," *Tissue Antigens*, 1983, 22:182-185.
Koller et al., "HLA-E. A novel HLA class I gene expressed in resting T lymphocytes," *J. Immunol.*, 1988, 141:897-904.
Kulkarni et al., "The Yin and Yang of HLA and KIR in human disease," *Semin Immunol.*, 2008, 20(6):343-52.
Larsen & Alper, "The genetics of HLA-associated disease," *Current Opinion in Immunology*, 2004, 16:660-667.
Lebedeva et al., "Comprehensive approach to high-resolution KIR typing," *Human Immunol*, 2007, 68(9):789-96.
Lee et al., "HLA-F is a surface marker on activated lymphocytes," *Eur J. Immunol.*, 2010, 40:2308-18.

(Continued)

*Primary Examiner* — Tracy Vivlemore
*Assistant Examiner* — Karen S Weiler
(74) *Attorney, Agent, or Firm* — Fish & Richardson P.C.

(57) ABSTRACT

Oligonucleotide-based microarrays for tissue typing (e.g., HLA tissue typing) are provided. More particularly, the microarrays are high resolution arrays useful for diagnostic evaluations and determining donor/recipient transplant compatibility.

77 Claims, 14 Drawing Sheets

(56) References Cited

OTHER PUBLICATIONS

Lin et al., "HLA Class II DR-DQ and Increased Risk of Cervical Cancer among Senegalese Women," *Cancer Epidemiol Biomarkers Prev.*, 2001, 10(10):1037-45.

Maiers et al., "High-resloution HLA alleles and haplotypes in the United States population," *Hum Immunol*, 2007, 68:779-88.

Marsh et al., "Killer-cell Immunoglobulin-like Receptors (KIR) Nomenclature Report 2002," *J Immunol Methods*, 2003, 281:1-8.

Michallet et al., "The impact of HLA matching on long-term transplant outcome after allogeneic hematopoietic stem cell transplantation for CLL: a retrospective study from the EBMT registry," *Leukemia*, 2010, 10:1725-31.

Passweg et al., "HLA and KIR polymorphisms affect NK-cell antitumor activity," *Trends Immunol*, 2007, 28(10):437-41.

Pearson and Regnier, "High-performance anion-exchange chromatography of oligonucleotides," *J. Chromo A*, 1983, 255:137-149.

Poland et al., "Vaccine Immunogenectics bedside to bench to population," *Vaccine*, 2008, 26(49):6183-8.

Rammensee, "Chemistry of peptides associated with MHC class I and Class II molecules," *Curr. Opin. Immunol.*, 1995, 7:85-96.

Robinson et al., "IPD—the Immuno Polymorphism Database," *Nucleic Acids Res.*, 2010, 38:D863-9.

Yershov et al., "DNA Analysis and Diagnostics on oligonucleotide microchips," *Proc. Natl. Acad. Sci. USA*, 1996, 93:4913-4918.

* cited by examiner

```
A*02:01:01:01    ATGGCCGTCATGGCGCCCCGAACCCTCGTCCTG...
P1               ATGGCCGTCATGGCGCCCCGAAC
P1N              ATGCGGGTCATCGCGCCCCCAAC
P2                TGGCCGTCATGGCGCCCCGAAC
P2N               TGCGGGTCATCGCGCCCCCAAC
P3                 GGCCGTCATGGCGCCCCGAAC
P3N                GCGGGTCATCGCGCCCCCAAC
P4                  GCCGTCATGGCGCCCCGAACC
P4N                 CGGGTCATCGCGCCCCCAACC
P5                   CCGTCATGGCGCCCCGAACCCT
P5N                  GGGTCATCGCGCCCCCAACCCT
P6                    CGTCATGGCGCCCCGAACCCTC
P6N                   GGTCATCGCGCCCCCAACCCTC
P7                     GTCATGGCGCCCCGAACCCTCGT
P7N                    GTCATCGCGCCCCCAACCCTCCT
P8                      TCATGGCGCCCCGAACCCTCGTC
P8N                     TCATCGCGCCCCCAACCCTCCTG
P9                       CATGGCGCCCCGAACCCTCGTC
P9N                      CATCGCGCCCCCAACCCTCCTG
P10                       ATGGCGCCCCGAACCCTCGTCCT
P10N                      ATCGCGCCCCCAACCCTCCTGCT
P11                        TGGCGCCCCGAACCCTCGTCCT
P11N                       TCGCGCCCCCAACCCTCCTGCT
P12                         GGCGCCCCGAACCCTCGTCCT
P12N                        CGCGCCCCCAACCCTCCTGCT
P13                          GCGCCCCGAACCCTCGTCCTG
P13N                         GCGCCCCCAACCCTCCTGCTG
```

FIG. 2

```
A*02:01:01:01  ATGGCCGTCATGGCGCCCCGAACCCTCGTCCTG...
P1             ATGGCCGTCATGGCGCCCCGAAC
P2              TGGCCGTCATGGCGCCCCGAAC
P3               GGCCGTCATGGCGCCCCGAAC
P4                GCCGTCATGGCGCCCCGAACC
P5                 CCGTCATGGCGCCCCGAACCCT
P6                  CGTCATGGCGCCCCGAACCCTC
P7                   GTCATGGCGCCCCGAACCCTCGT
P8                    TCATGGCGCCCCGAACCCTCGTC
P9                     CATGGCGCCCCGAACCCTCGTC
P10                      ATGGCGCCCCGAACCCTCGTCCT
P11                       TGGCGCCCCGAACCCTCGTCCT
P12                        GGCGCCCCGAACCCTCGTCCT
P13                         GCGCCCCGAACCCTCGTCCTG
```

FIG. 3

Total number of unique probes at position 31 is 9

| | E1S1R1 | E1S1R2 | E1S1R3 | E1S1R4 | E1S2R1 | E1S2R2 | E1S2R3 | E1S2R4 | E2S1R1 | E2S1R2 | E2S1R3 | E2S1R4 | E2S2R1 | E2S2R2 |
|---|---|---|---|---|---|---|---|---|---|---|---|---|---|---|
| Max | 222 | 258 | 150 | 211 | 471 | 546 | 355 | 327 | 148 | 157 | 388 | 906 | 518 | 1130 |
| Min | 33 | 40 | 21 | 39 | 55 | 67 | 33 | 25 | 1 | 27 | 1 | 1 | 7 | 6 |
| Mean | 90 | 108 | 70 | 88 | 173 | 209 | 144 | 138 | 64 | 73 | 154 | 233 | 145 | 282 |
| Median | 62 | 98 | 68 | 60 | 126 | 149 | 105 | 99 | 36 | 57 | 121 | 97 | 97 | 128 |
| GeoMean | 73 | 93 | 61 | 73 | 131 | 166 | 115 | 106 | 35 | 60 | 64 | 79 | 80 | 107 |

A*01010101 vs. A*02010101: Times of winning

| Allele | Length | E1S1A1(A0) |
|---|---|---|
| A*01010101 | 1098 | 118 |
| A*02010101 | 1098 | 42 |

A*01010101 vs. A*03010101: Times of winning

| Allele | Length | E1S1A1(A0) |
|---|---|---|
| A*01010101 | 1098 | 8 |
| A*03010101 | 1098 | 47 |

A*01010101 vs. A*110101: Times of winning

| Allele | Length | E1S1A1(A0) |
|---|---|---|
| A*01010101 | 1098 | 14 |
| A*110101 | 1098 | 17 |

A*01010101 vs. A*2301: Times of winning

| Allele | Length | E1S1A1(A0) |
|---|---|---|
| A*01010101 | 1098 | 105 |
| A*2301 | 1098 | 40 |

A*01010101 vs. A*24020101: Times of winning

| Allele | Length | E1S1A1(A0) |
|---|---|---|
| A*01010101 | 1098 | 102 |
| A*24020101 | 1098 | 39 |

FIG. 10B

**Pairwise comparison between A*02010101 and A*03010101**

| Allele | Starting position | Probe | Melting temperature | HLA coverage | ELSLA2(A1) Signal | Voting |
|---|---|---|---|---|---|---|
| A*02010101 | 7 | GTCATGGCGCCCGAACCCTCGT | 64.2 | 90 | 153 1.51 | similar |
| A*03010101 | | GTCATGGCGCCCGAACCCTCCT | 64.2 | 69 | 180 1.78 | |
| A*02010101 | 10 | ATGGCGCCCCGAACCCTCGTCT | 64.2 | 92 | 248 1.33 | similar |
| A*03010101 | | ATGGCGCCCCGAACCCTCCTCT | 64.2 | 81 | 231 1.24 | |
| A*02010101 | 13 | GCGCCCCGAACCCTCGTCCTG | 64.1 | 94 | 6699 1.11 | A*03010101 |
| A*03010101 | | GCGCCCCGAACCCTCCTCCTG | 64.1 | 150 | 13346 2.20 | |
| A*02010101 | 14 | CGCCCCGAACCCTCGTCCTGCTA | 64.2 | 94 | 10867 1.21 | similar |
| A*03010101 | | CGCCCCGAACCCTCCTCCTGCTA | 64.2 | 51 | 20000 2.22 | |
| A*02010101 | 15 | GCCCCGAACCCTCGTCCTGCTACT | 64.2 | 94 | 3933 0.32 | A*03010101 |
| A*03010101 | | GCCCCGAACCCTCCTCCTGCTACT | 64.2 | 51 | 10254 2.12 | |
| A*02010101 | 16 | CCCCGAACCCTCGTCCTGCTACTCT | 64.2 | 95 | 1481 0.46 | A*03010101 |
| A*03010101 | | CCCCGAACCCTCCTCCTGCTACTCT | 64.2 | 51 | 4691 1.45 | |
| A*02010101 | 17 | CCCGAACCCTCGTCCTGCTACTCTC | 64.2 | 95 | 828 0.54 | A*03010101 |
| A*03010101 | | CCCGAACCCTCCTCCTGCTACTCTC | 64.2 | 34 | 1822 1.18 | |
| A*02010101 | 18 | CCGAACCCTCGTCCTGCTACTCTCG | 64.2 | 95 | 418 0.44 | A*03010101 |
| A*03010101 | | CCGAACCCTCCTCCTGCTACTCTCG | 64.2 | 34 | 889 0.94 | |
| A*02010101 | 19 | CGAACCCTCGTCCTGCTACTCTCGG | 64.2 | 95 | 557 0.42 | similar |
| A*03010101 | | CGAACCCTCCTCCTGCTACTCTCGG | 64.2 | 34 | 477 0.57 | |
| A*02010101 | 20 | GAACCCTCGTCCTGCTACTCTCGGG | 64.2 | 95 | 422 0.35 | similar |
| A*03010101 | | GAACCCTCCTCCTGCTACTCTCGGG | 64.2 | 34 | 645 0.54 | |
| A*02010101 | 21 | AACCCTCGTCCTGCTACTCTCGGGG | 64.2 | 96 | 504 0.64 | similar |
| A*03010101 | | AACCCTCCTCCTGCTACTCTCGGGG | 64.2 | 35 | 878 1.12 | |
| A*02010101 | 22 | CCTCGTCCTGCTACTCTCGGGGG | 64.2 | 97 | 201 0.33 | A*03010101 |
| A*03010101 | | CCTCCTCCTGCTACTCTCGGGGGG | 64.2 | 35 | 712 1.18 | |
| A*02010101 | 25 | CGTCCTGCTACTCTCGGGGGCT | 64.2 | 40 | 272 0.73 | similar |
| A*03010101 | | CCTCCTGCTACTCTCGGGGGGC | 64.2 | 35 | 172 0.46 | |
| A*02010101 | 26 | TCGTCCTGCTACTCTCGGGGGCTCT | 64.2 | 41 | 350 1.54 | A*02010101 |
| A*03010101 | | TCCTCCTGCTACTCTCGGGGGGCC | 64.2 | 35 | 113 0.50 | |
| A*02010101 | 28 | GTCCTGCTACTCTCGGGGGCTCTG | 64.2 | 41 | 500 1.97 | A*03010101 |
| A*03010101 | | CTCCTGCTACTCTCGGGGGGCCCT | 64.2 | 35 | 144 0.57 | |
| A*02010101 | 29 | TCCTGCTACTCTCGGGGGCTCTGG | 64.2 | 41 | 187 1.13 | similar |
| A*03010101 | | TCCTGCTACTCTCGGGGGGCCCTG | 64.2 | 92 | 121 0.73 | |
| A*02010101 | 31 | CTGCTACTCTCGGGGGCTCTGGCC | 64.2 | 41 | 98 0.91 | A*02010101 |
| A*03010101 | | CTGCTACTCTCGGGGGGCCCTGG | 64.2 | 92 | 52 0.43 | |
| A*02010101 | 32 | TGCTACTCTCGGGGGCTCTGGCC | 64.2 | 41 | 84 1.45 | |

FIG. 10C

Summary of voting
E1S1A1(A0)

| Winning | A*01010101 | A*02010101 | A*03010101 | A*110101 | A*2301 | A*24020101 | A*250101 | A*260101 | A*2901010 | A*300101 | A*310102 | A*320101 | A*3301 | A*340101 |
|---|---|---|---|---|---|---|---|---|---|---|---|---|---|---|
| A*01010101 | 0 | -76 | 39 | 3 | -65 | -63 | 11 | 29 | -21 | 7 | -18 | -9 | -20 | 10 |
| A*02010101 | 76 | 0 | 106 | 74 | 8 | 8 | 89 | 105 | 61 | 70 | 54 | 83 | 51 | 84 |
| A*03010101 | -39 | -106 | 0 | -32 | -90 | -97 | -22 | -6 | -49 | -27 | -51 | -42 | -49 | -20 |
| A*110101 | -3 | -74 | 32 | 0 | -67 | -70 | 10 | 25 | -24 | 3 | -25 | -12 | -23 | 9 |
| A*2301 | 65 | -8 | 90 | 67 | 0 | -2 | 82 | 99 | 57 | 58 | 62 | 79 | 61 | 78 |
| A*24020101 | 63 | -8 | 97 | 70 | 2 | 0 | 91 | 108 | 63 | 64 | 68 | 85 | 67 | 89 |
| A*250101 | -11 | -89 | 22 | -10 | -82 | -91 | 0 | 18 | -28 | -8 | -28 | -10 | -28 | -11 |
| A*260101 | -29 | -105 | 6 | -25 | -99 | -108 | -18 | 0 | -48 | -24 | -46 | -30 | -46 | -26 |
| A*29010101 | 21 | -61 | 49 | 24 | -57 | -63 | 28 | 48 | 0 | 24 | 3 | 5 | 5 | 21 |
| A*300101 | -7 | -70 | 27 | -3 | -58 | -64 | 8 | 24 | -24 | 0 | -21 | -11 | -21 | 8 |
| A*310102 | 18 | -54 | 51 | 25 | -62 | -68 | 28 | 46 | 3 | 21 | 0 | 4 | 4 | 19 |
| A*320101 | 9 | -83 | 42 | 12 | -79 | -85 | 10 | 30 | -5 | 11 | -4 | 0 | -2 | -1 |
| A*3301 | 20 | -51 | 49 | 23 | -61 | -67 | 28 | 46 | 5 | 21 | 4 | 2 | 0 | 23 |
| A*340101 | -10 | -84 | 20 | -9 | -78 | -89 | 11 | 26 | -21 | -8 | -19 | 1 | -23 | 0 |
| A*3601 | -11 | -84 | 33 | -7 | -72 | -71 | 3 | 21 | -29 | -1 | -26 | -17 | -29 | 2 |
| A*4301 | 19 | -99 | 17 | -14 | 96 | -105 | -7 | 11 | -35 | -16 | -39 | -20 | -35 | -13 |
| A*6601 | -18 | -98 | 14 | -17 | -90 | -99 | -6 | 9 | -38 | -16 | -35 | -20 | -33 | -14 |
| A*680101 | 54 | 39 | 67 | 33 | 46 | -47 | 49 | 65 | 19 | 50 | 12 | 44 | 10 | 43 |
| A*6901 | 41 | -32 | 72 | 40 | 34 | -34 | 59 | 75 | 20 | 36 | 17 | 47 | 15 | 51 |
| A*7401 | 2 | -85 | 37 | 6 | -78 | -84 | 7 | 23 | -12 | 6 | -8 | 3 | -6 | -7 |
| A*8001 | 56 | 13 | 88 | 62 | 10 | 10 | 83 | 99 | 70 | 70 | 63 | 78 | 61 | 78 |
| Avg | 12.29 | -61.57 | 45.62 | 15.33 | -57.05 | -61.19 | 25.90 | 42.90 | 2.48 | 15.29 | -1.67 | 12.10 | -2.33 | 20.14 |

FIG. 10D

OLIGONUCLEOTIDE ARRAY FOR TISSUE TYPING

RELATED APPLICATIONS

The present application claims the benefit of U.S. Provisional Patent Application Ser. No. 61/423,991, filed Dec. 16, 2010, which is herein incorporated by reference in its entirety.

STATEMENT REGARDING FEDERALLY SPONSORED RESEARCH OR DEVELOPMENT

The research described in this application was supported in part by grant (Nos. U19 AI57330 and UO1 AI90043) from the National Institutes of Health. Thus, the government has certain rights in the invention.

REFERENCE TO SEQUENCE LISTING

Pursuant to 37 C.F.R. 1.821(c), a sequence listing is submitted herewith via EFS-Web as an ASCII compliant text file named "Sequencelisting.txt" that was created on Feb. 3, 2012, and has a size of 103,990,947 bytes. The content of the aforementioned file named "Sequencelisting.txt" is hereby incorporated by reference in its entirety.

TECHNICAL FIELD

This invention relates to tissue typing using an oligonucleotide-based microarray. More particularly, the HLA arrays are high resolution arrays useful for diagnostic evaluations and determining donor/recipient transplant compatibility.

BACKGROUND

HLA variation is a crucial determinant of transplant rejection, susceptibility to a large number of infectious and autoimmune diseases, and cancer. The limiting factor in large-scale genetic analysis of, for example, transplant populations has been methodologic and directly involves the technical ability to accurately define the alleles of highly polymorphic HLA genes in a cost-effective and efficient manner. Although recent progress in the development of traditional probe hybridization, sequencing and array-based methods has allowed alleles to be determined with accuracy, large-scale efforts in genetic analysis of transplant populations are hampered by the cost and inefficiency of available methods.

In particular, current array-based methods are inefficient, because resolution of ambiguities is not guaranteed, and multiple arrays are needed to conduct a complete analysis of all HLA genes. Exemplary limitations of currently available HLA arrays include for example, that they are suitable for low-to-medium density genotyping but not for high-density genotyping; they do not have a complete set of probes (i.e. capture oligonucleotides that recognize target HLA encoding nucleic acids), but rather have only a selection of "informative probes", thereby making deconvolution of ambiguities difficult or impossible; they do not cover all currently known HLA alleles from each group; and they do not encode a complete set of classical and non-classical HLA loci. Current methodologies, e.g., microarrays, are typically limited to identifying one or several classical HLA molecules (e.g., HLA-A, HLA-B or HLA-C) per assay, and cannot simultaneously determine the haplotype of all classical MHC molecules. Nor can current methodologies simultaneously determine the haplotype of non-classical HLA molecules or accessory molecules (e.g., those important in antigen processing and peptide loading on HLA molecules) in the same assay, and thus do not efficiently provide a complete picture of an individual's HLA tissue type, as needed, e.g., to understand the linkage between certain tissue types and disease susceptibility, and for determining donor/recipient compatibility in tissue transplant.

There therefore exists a need in the art for new and improved methods for not only the identification of all alleles of any HLA molecule, but the ability to identify all alleles of all HLA molecules known at the time of identification, as well as certain other polymorphic molecules, in a single assay. This invention addresses these and other needs as described in detail below.

SUMMARY OF THE INVENTION

In certain embodiments, the invention provides a method for human leukocyte antigen (HLA) tissue typing, said method comprising: (a) contacting a cDNA- or cRNA-containing sample under hybridization conditions with a plurality of capture oligonucleotides specific for HLA polypeptides, wherein said hybridization conditions facilitate hybridization of a subset of capture oligonucleotides to complementary sequences present in the cDNA or cRNA; (b) detecting a hybridization pattern for said cDNA or cRNA; and (c) assigning to the sample, based on the hybridization pattern, an HLA tissue type; wherein the capture oligonucleotides are from about 17 to about 60 nucleotides in length and each capture oligonucleotide with respect to its exact complement has a melting temperature of about 64 degrees Celsius; wherein said capture oligonucleotides comprise subsets of oligonucleotides that collectively target classical HLA polypeptide-encoding nucleic acids ("classical HLA oligo subsets"), each classical HLA oligo subset targeting a different classical HLA polypeptide-encoding nucleic acid; and wherein each of said classical HLA oligo subsets comprises a set of overlapping oligonucleotides that cover every single nucleotide position in the mRNA sequences coding for the classical HLA polypeptides from 5' to 3' and are sequentially shifted by 1-5 nucleotides from the 5' end of the preceding overlapping oligonucleotide. In certain embodiments, in step (a), said cDNA or cRNA was detectably labeled during the making, and said detecting step (b) comprises detecting said detectably labeled cDNA or cRNA. In other embodiments, the detecting step (d) comprises the use of labeled detection probes. In a specific embodiment, the capture oligonucleotides comprise subsets of oligonucleotides that collectively target all known classical HLA polypeptide-encoding nucleic acids. In one embodiment, the capture oligonucleotides are immobilized on a substrate.

In one embodiment, said classical HLA polypeptide-encoding nucleic acids encode HLA polypeptides selected from the group consisting of HLA-A, HLA-B, HLA-C, HLA-DR, HLA-DP, and HLA-DQ.

In another embodiment, said capture oligonucleotides further comprise a plurality of oligonucleotide subsets that collectively targets non-classical HLA polypeptide-encoding nucleic acids ("non-classical HLA oligo subsets"), each non-classical HLA oligo subset targeting a different non-classical HLA polypeptide-encoding nucleic acid; wherein each of said non-classical HLA oligo subsets comprises a set of overlapping oligonucleotides that cover every single nucleotide position in the mRNA sequences coding for the non-classical HLA polypeptides from 5' to 3' and are sequentially shifted by 1-5 nucleotides from the 5' end of the preceding overlapping oligonucleotide. In a specific embodiment, the plurality of oligonucleotide subsets that collectively targets non-classical HLA polypeptide-encoding nucleic acids collectively target all known non-classical HLA polypeptide-encoding nucleic acids.

In another embodiment, said non-classical HLA polypeptide-encoding nucleic acids encode HLA polypeptides selected from the group consisting of HLA-E, HLA-F, HLA-G, DM, DO and MIC.

In certain embodiments, said capture oligonucleotides further comprise a plurality of oligonucleotide subsets that collectively targets nucleic acids encoding accessory molecules important in HLA-linked peptide presentation and/or processing ("accessory molecule oligo subsets"), and said method further comprises the step of assigning to the sample, based on the hybridization pattern, an accessory molecule phenotype; wherein each of said accessory molecule oligo subsets comprises a set of overlapping oligonucleotides that cover every single nucleotide position in the mRNA sequences coding for the accessory molecules from 5' to 3' and are sequentially shifted by 1-5 nucleotides from the 5' end of the preceding overlapping oligonucleotide. In a specific embodiment, said accessory molecules are selected from the group consisting of LMP2, LMP7, LMP10, tripeptidyl peptidase II (TPPII), bleomycin hydrolase (BLMH), leucine aminopeptidase 3 (LAP3), transporter associated with antigen processing (TAP) 1, TAP2, 2-microglobulin, TAP binding protein (tapasin), calnexin (CANX), calreticulin (CALR), protein disulfide isomerase family A member 2 (PDIA2), protein disulfide isomerase family A member 3 (PDIA3), ERp57, endoplasmic reticulum aminopeptidase (ERAP) 1, ERAP2, proteasome (prosome macropain) subunit althap (PSMA) type I (PSMA1), PSMA2, PSMA3, PSMA4, PSMA5, PSMA6, PSMA7, PSMA8, proteasome (prosome macropain) subunit beta (PSMB) type 1 (PSMB1), PSMB2, PSMB3, PSMB4, PSMB5, PSMB6, PSMB7, PSMB8, PSMB9, PSMB10, PSMB11, proteasome (prosome macropain) 26S subunit ATPase (PSMC) 1 (PSMC1); PSMC2, PSMC3, PSMC4, PSMC5, PSMC6, proteasome (prosome macropain) 26S subunit non-ATPase (PSMD) 1 (PSMD1), PSMD2, PSMD3, PSMD4, PSMD5, PSMD6, PSMD7, PSMD8, PSMD9, PSMD10, PSMD11, PSMD12, PSMD13, and PSMD14.

In certain of the above embodiments, said capture oligonucleotides further comprise a plurality of oligonucleotide subsets targeting killer-cell immunoglobulin-like receptor (KIR) polypeptide-encoding nucleic acids ("KIR oligo subsets"), and said method further comprises the step of assigning to the sample, based on the hybridization pattern, a KIR polypeptide phenotype; wherein each of said KIR oligo subsets comprises a set of overlapping oligonucleotides that cover every single nucleotide position in the mRNA sequences coding for the KIR polypeptides from 5' to 3' and are sequentially shifted by 1-5 nucleotides from the 5' end of the preceding overlapping oligonucleotide.

In certain of the above embodiments, said capture oligonucleotides further comprise a plurality of oligonucleotide subsets targeting blood group-determining polypeptide encoding nucleic acids ("blood group determining oligo subsets"), and said method further comprises the step of assigning to the sample, based on the hybridization pattern, a blood group phenotype; wherein each of said blood group determining oligo subsets comprises a set of overlapping oligonucleotides that cover every single nucleotide position in the mRNA sequences coding for the blood group-determining polypeptides from 5' to 3' and are sequentially shifted by 1-5 nucleotides from the 5' end of the preceding overlapping oligonucleotide. In a specific embodiment, said blood group determining polypeptides are selected from the group consisting ABO (ABO), Chido Rodgers (CH/RG), Colton (CO), Cromer (CROM), Diego (DI) (band 3), Dombrock (DO), Duffy (DARC), Gerbich (Ge), Gill (GIL), Globoside and Pk, H(H), I (I), Indian (IN), John Milton Hagen (JMH), Kell (KEL) and Kx (XK), Kidd (JK), Knops (KN), Landsteiner-Wiener (LW), Lewis (LE), Lutheran (LU), MNS (MNS, Glycophorins A, B and E), Ok (OK), Raph (RAPH), Rh (RH) and Rh-gp (RHAG), Scianna (SC), T/Tn, Xg (XG), and Yt (YT).

In certain of the above embodiments, the method further comprises the step of deriving from the HLA tissue type assigned in step (d) donor/recipient transplant compatibility.

In one embodiment, the classical HLA oligo subsets comprise the sequences set forth in Table I or the normal (indicated by "HPN"), extended (indicated by "HPE") and truncated "indicated by HPT") sequences set forth in Table X. In another embodiment, the non-classical HLA oligo subsets comprise the sequences set forth in Table II. In still another embodiment, the accessory molecule oligo subsets comprise the sequences set forth in Table III. In yet another embodiment, the KIR oligo subsets comprise the sequences set forth in Table IV. In still another embodiment, the blood group determining oligo subsets comprise the sequences set forth in Table V.

In certain of the above embodiments, in each set of overlapping oligonucleotides, each oligonucleotide is sequentially shifted by 1 nucleotide from the 5' end of the preceding overlapping oligonucleotide. In another of the above embodiments, in each set of overlapping oligonucleotides, each oligonucleotide is sequentially shifted by 2 nucleotides from the 5' end of the preceding overlapping oligonucleotide. In certain other of the above embodiments, in each set of overlapping oligonucleotides, each oligonucleotide is sequentially shifted by 3 nucleotides from the 5' end of the preceding overlapping oligonucleotide. In still other of the above embodiments, in each set of overlapping oligonucleotides, each oligonucleotide is sequentially shifted by 4 nucleotides from the 5' end of the preceding overlapping oligonucleotide. In certain of the above embodiments, in each set of overlapping oligonucleotides, each oligonucleotide is sequentially shifted by 5 nucleotides from the 5' end of the preceding overlapping oligonucleotide.

In one embodiment, said sample for HLA tissue tying is obtained from a human subject. In certain embodiments, the method for HLA tissue typing comprises the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, wherein the step is based on one or more assigned tissue types or phenotypes selected from the group consisting of: a classical HLA tissue type, a non-classical HLA tissue type, an accessory molecule phenotype, a KIR polypeptide phenotype, and a blood group phenotype.

In certain of the above embodiments, the method for HLA tissue typing further comprises the step of determining the likely response of said subject to a particular treatment regimen selected from the group consisting of: bone marrow transplantation, immunosuppressive regimen, antiviral drug regimen, antiviral drug resistance, antiretroviral drug regimen, and autoimmunity drug regimen, wherein the step is based on one or more assigned phenotypes selected from the group consisting of: a classical HLA tissue type, a non-classical HLA tissue type, an accessory molecule phenotype, a KIR polypeptide phenotype, and a blood group phenotype. In certain other embodiments, the method for HLA tissue typing further comprises the step of determining whether the subject is likely to develop antiretroviral drug resistance or cancer drug regimen resistance, wherein the step is based on one or more assigned phenotypes selected from the group consisting of: a classical HLA tissue type, a non-classical HLA tissue type, an accessory molecule phenotype, a KIR polypeptide phenotype, and a blood group phenotype.

In certain of the above embodiments, said capture oligonucleotides further comprise at least one set of negative control oligonucleotides. In certain embodiments, said at least one set of negative control nucleotides comprises two or more of the nucleic acid sequences set forth in at least one of Tables VI-X.

In one embodiment, a microarray comprising a substrate having disposed thereon capture oligonucleotides comprising the nucleic acid sequences set forth in Table I is provided. In another embodiment, a microarray comprising a substrate having disposed thereon capture oligonucleotides comprising the nucleic acid sequences set forth in Table I further has disposed thereon capture oligonucleotides comprising the nucleic acid sequences set forth in Table II.

In another embodiment, a microarray comprising a substrate having disposed thereon capture oligonucleotides comprising the nucleic acid sequences set forth in Table X is provided. In another embodiment, a microarray comprising a substrate having disposed thereon capture oligonucleotides comprising the nucleic acid sequences set forth in Table X and denoted by "HPN," "HPE" or "HPT" is provided. In another embodiment, a microarray comprising a substrate having disposed thereon capture oligonucleotides comprising the nucleic acid sequences set forth in Table II is provided.

In certain of the embodiments, the microarray having disposed thereon capture oligonucleotides comprising the nucleic acid sequences set forth in Table I and/or Table II, further has disposed thereon capture oligonucleotides comprising the nucleic acid sequences set forth in one or more of Tables III-X.

Unless otherwise defined, all technical and scientific terms used herein have the same meaning as commonly understood by one of ordinary skill in the art to which this invention pertains. In case of conflict, the present document, including definitions, will control.

All publications, patent applications, patents, and other references mentioned herein are incorporated by reference in their entirety. The materials, methods, and examples disclosed herein are illustrative only and not intended to be limiting.

The details of one or more embodiments of the invention are set forth in the accompanying drawings and the description below. Preferred methods and materials are described below, although methods and materials similar or equivalent to those described herein can also be used in the practice or testing of the present invention. Other features, objects, and advantages of the invention will be apparent from the description and drawings, and from the claims.

DESCRIPTION OF DRAWINGS

FIG. 2 shows a set of oligonucleotides (P1 to P13) covering A*02:01:01:01 sequence and their corresponding negative control oligonucleotides (P1N to P13N) generated based on the consensus sequence of HLA class I sequence group. The oligonucleotide sequences shown in FIG. 2 have, from top to bottom, SEQ ID NOs: 428783-428809.

FIG. 3 shows a set of tiling capture oligonucleotides (P1 to P13) covering the A*02:01:01:01 sequence. The oligonucleotide sequences shown in FIG. 3 have, from top to bottom, SEQ ID NOs: 428810-428823.

FIG. 7 is a table displaying the maximum, minimum, mean, median, and geometric mean of the probe signals at position 31 of alignment of all HLA-A, B, C alleles.

FIG. 10 shows an example of applying a pairwise comparison method on array E1A1A1 for predicting of HLA-A alleles. (A) The input page of pairwise comparison method. A list of representative HLA-A alleles are input in the text box and array E1S1A1 is chosen. (B) Pairwise comparison is performed between each pair of the input alleles. The times of winning of one allele over the other are summarized in a table. (C) The detailed signal comparison table of A*02010101 against A*03010101. Each allele is indicated in the first column (on left); the starting nucleic acid position is shown in the second column; the oligonucleotide sequences are given in the third column, labeled "Probe", and have, numbered from top to bottom, SEQ ID NOs: 428824-428858; the melting temperature (in degrees Celsius) is shown in the fourth column; HLA coverage is shown in the fifth column and the numbers represent the number of different alleles; the sixth column shows the array signal for each oligo; and the seventh column shows the voting results—"similar" means there was no winner and if there was a winner, the winning allele is identified. (D) The final voting table summarizing the voting situation of all the alleles is shown; each individual number describes the difference between number of winning in pairwise comparison; for example 106 in the row 3 column 4 means that A*03010101 won 106 times more than A*02010101 in pairwise comparison. The values in the bottom row are the averages of all results in each column, indicating the overall voting value. The highlighted cells indicate the likely winners, which need to be checked for potential masking.

DETAILED DESCRIPTION

Overview

Figure 1:
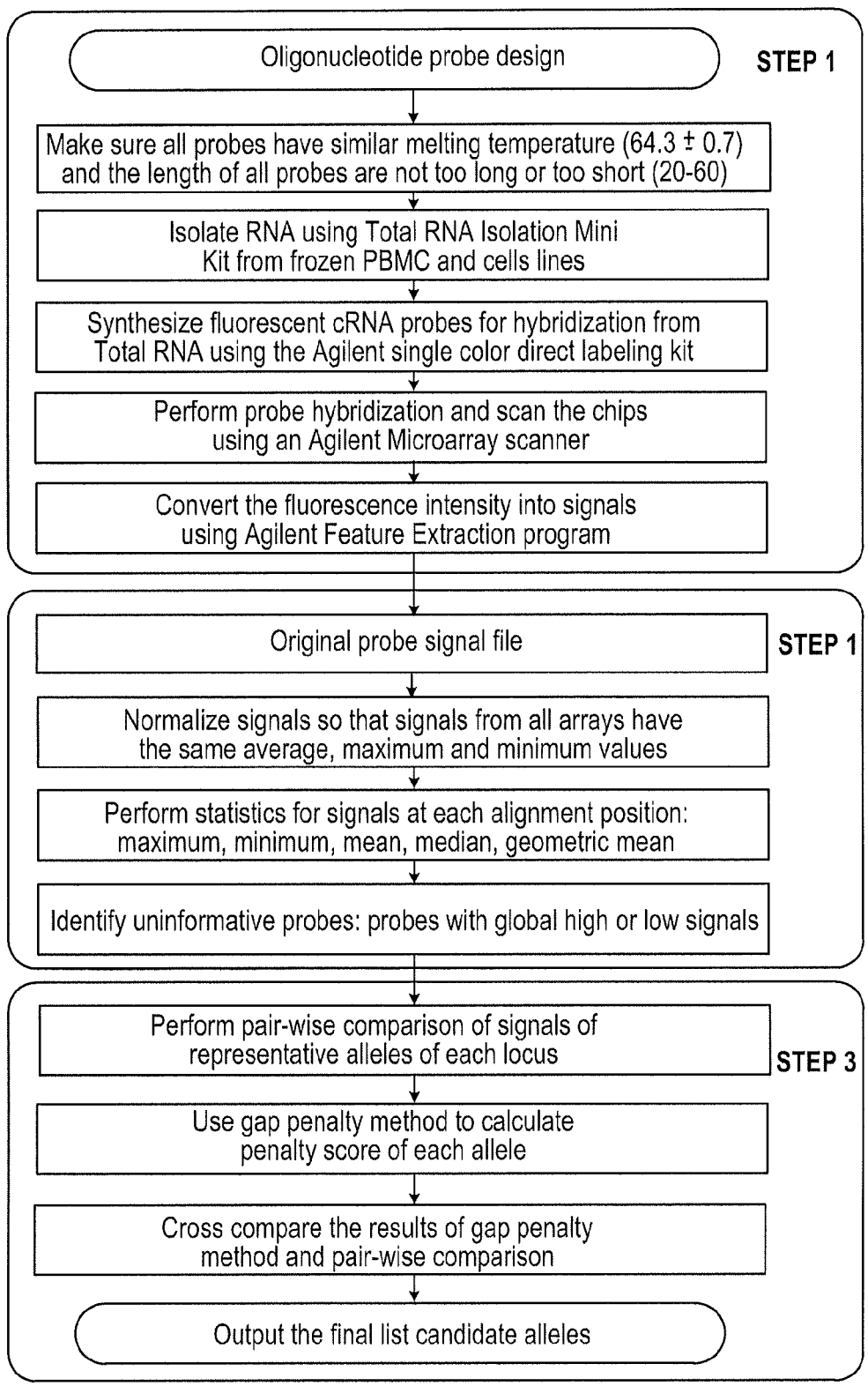
FIG. 1 is a flow chart of HLA typing using an oligonucleotide microarray. The whole process can be organized into three major steps. The first step involves oligonucleotide "probe" design and microarray experiment. The second step covers probe signal (i.e., fluorescent cRNA) preprocessing. The third step covers the signal analysis programs for identification of sample HLA profiles.

Various aspects of the invention are described below.

Provided herein are capture oligonucleotides and methods of their use for determining with high resolution the haplotypes of several families of polymorphic polypeptides. Within a specific embodiment, the polymorphic polypeptides are HLA polypeptides. Within one embodiment, the invention provides an array comprising capture oligonucleotides that target nucleic acids encoding classical HLA polypeptides. Within another embodiment, the array comprises capture oligonucleotides that target nucleic acids encoding non-classical HLA polypeptides. Within yet another embodiment, the array comprises capture oligonucleotides that target nucleic acids encoding all known classical and non-classical HLA polypeptides, and in certain embodiments, the array additionally or alternatively comprises capture oligonucleotides that target nucleic acids encoding accessory molecules important in HLA-linked peptide presentation and/or antigen processing, killer-cell immunoglobulin-like receptor (KIR) polypeptides, and/or blood group determining polypeptides. All of these different targets (e.g., classical and non-classical HLA polypeptides accessory molecules, KIR polypeptides and blood group determining polypeptides) are referred to collectively herein as "array targets."

Within certain embodiments, a key feature of the methods and oligonucleotide arrays provided herein is that they provide an efficient and accurate method for determining the HLA tissue type of a sample using a single assay (e.g., array chip). This feature provides a dramatic improvement over currently available "traditional" technologies, which are inefficient because they typically require multiple assays and follow up nucleic acid sequencing in order to determine the complete HLA tissue type of a sample.

Within certain embodiments, the arrays comprise sets of capture oligonucleotides that provide a highly dense coverage of the entire polypeptide-encoding nucleic acid sequence of each array target using an approach referred to herein as "walking." Using the "walking" approach, each oligonucleotide in a capture oligonucleotide set (i.e. a set targeting one specific array target) is sequentially shifted by about 1 to about 5 nucleotides from the 5' end of the preceding overlapping oligonucleotide. Herein, sequential shifting by 1 nucleotide is also referred to as "step 1", sequential shifting by 2 nucleotides is also referred to as "step 2", and so on. As an example of this process, if a first oligonucleotide has the sequence, ATGGCCGTCATGGCGCCCCGAAC (SEQ ID NO: 1), the next oligonucleotide in the set, if it is sequentially shifted by 1 nucleotide (i.e., a "step 1 shift") will have the sequence TGGCCGTCATGGCGCCCCGAAC (SEQ ID NO: 2), whereas if that oligonucleotide is sequentially shifted by 2 nucleotides, rather than 1, it can have the sequence GGCCGTCATGGCGCCCCGAAC (SEQ ID NO: 3), and so on. This approach produces a set of highly overlapping capture oligonucleotides, thereby providing dense coverage of each target sequence, which is important for high resolution typing of highly polymorphic genes such as HLA.

In other embodiments, the arrays comprise capture oligonucleotides that target accessory molecules important in peptide loading on HLA molecules and/or antigen processing, and/or killer-cell immunoglobulin-like receptor (KIR) polypeptides, and/or blood group determining polypeptides. In a preferred embodiment, the array comprises capture oligonucleotides that target classical HLA molecules and/or non-classical HLA molecules (such arrays being referred to herein in general as "HLA oligonucleotide arrays"), and, in addition, comprises capture oligonucleotides that target accessory molecules important in peptide loading on HLA molecules and/or antigen processing, and/or KIR polypeptides, and/or blood group determining polypeptides. The inclusion of these additional targets, e.g., certain accessory molecules, KIR polypeptides and/or blood group determining polypeptides, in the HLA oligonucleotide array provides an efficient tool for obtaining a detailed analysis of a patient sample relevant for a wide variety of immunologic applications.

For example, within certain embodiments, the arrays and methods of their use described herein are useful for diagnosing or predicting the likelihood of an HLA-linked genetic defect, disease, inadequate or undesirable response to a vaccine, biologic treatment (recombinant protein, biosimilar or equivalent), or infectious organism or condition in said subject, wherein the step is based on one or more assigned tissue types or phenotypes selected from the group consisting of: a classical HLA tissue type, a non-classical HLA tissue type, an accessory molecule phenotype, a KIR polypeptide phenotype, and a blood group phenotype.

Within another embodiment, the immunologic application of the arrays provided herein includes the ability to derive donor/recipient compatibility for bone marrow/tissue/organ transplant.

Definitions

As used herein, the term "HLA polypeptide" refers to an amino acid sequence encoded by a human leukocyte antigen ("HLA") allele. The term, "HLA haplotype" refers to a combination of specific alleles from different HLA loci expressed as a combination of HLA genes characteristic for a given individual.

As used herein, the term "all known" in the context of classical and/or non-classical HLA molecules means all of the HLA alleles for which the nucleic acid sequences are publically available at the time of assigning an HLA haplotype to a sample using the method claimed herein. The sequences are preferably, although not necessarily, available from publically accessible databases, which are constantly updated with all known sequences available, such as, e.g., the HLA database IMGT/HLA, accessible at http://www.ebi.ac.uk/imgt/hla/, the KIR database IPD-KIR, accessible at http://www.ebi.ac.uk/ipd/kir/, and the blood group antigen database accessible at http://www.ncbi.nlm.nih.gov/projects/gv/mhc/xslcgi.cgi?cmd=bgmut/systems. Allele sequences for, e.g., accessory molecules and other molecules, are also available at GenBank® (National Institutes of Health (NIH) genetic sequence database), available at http://www.ncbi.nlm.nih.gov/).

The term "tissue typing" as used herein refers to determining which of a number of isoforms and alleles of one or more families of polymorphic protein molecules are expressed in a cell (e.g., tissue). Such families include, for example, classical HLA polypeptides, non-classical HLA polypeptides, KIR polypeptides, accessory molecule polypeptides, and blood group determining polypeptides.

The terms "HLA typing" and "HLA tissue typing" are used interchangeably herein, and refer to the process that identifies the specific allele expressed for each gene at one or more of the HLA-A, HLA-B, HLA-C, HLA-DR, HLA-DQ, and HLA-DP (classical HLA) gene loci in a sample (e.g., cells such as white blood cells, or cells derived from tissues). The process described by these terms can also, but does not necessarily, include identifying the specific allele expressed for each gene at one or more of the HLA-E, HLA-F, HLA-G, DM, DO, and MIC (non-classical HLA) gene loci.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90% sequence identity, at least 95% sequence identity, or at least 99% sequence identity.

As used herein, the phrase "under hybridization conditions" means conditions under conditions that facilitate specific hybridization of a subset of capture oligonucleotides to complementary sequences present in the cDNA or cRNA. The terms "hybridizing specifically to" and "specific hybridization" and "selectively hybridize to," as used herein refer to the binding, duplexing, or hybridizing of a nucleic acid molecule preferentially to a particular nucleotide sequence under at least moderately stringent conditions, and preferably, highly stringent conditions, as discussed above.

As used herein, the term "complementary sequence," when referring to a nucleic acid sequence, refers to the nucleic acid base sequence that can form a double-stranded structure (duplex) by matching bases to bases in a reference sequence. For example, the complementary sequence to the reference sequence G-T-A-C is C-A-T-G (SEQ ID NOs: 428859 and 428860, respectively). Within certain embodiments, a complementary sequence can have mismatches at certain nucleic acid residues with the reference sequence. In contrast, as used herein, the "exact complement" of a reference nucleic acid sequence refers to a complementary sequence that contains no base mismatches with the reference sequence.

As used herein, the term "hybridization pattern" refers to the raw data of a microarray assay, wherein, for example, the detectably labeled nucleic acid sample (e.g., cDNA or cRNA), or detectably labeled detection probes bound to nucleic acids (cDNA or cRNA sample) hybridized to capture oligonucleotides on the array, are detected in a specific pattern of detectable signal, the specific pattern being determined by which nucleic acid targets are present in the tested sample. Hybridization patterns of different samples can also be compared visually, as long as the samples are hybridized to microarray slides having capture oligonucleotides spotted on the slides in identical locations. Hybridization patterns can be determined using, e.g., pattern recognition algorithms.

As used herein, the term "classical HLA oligo subset" refers to a collection of capture oligonucleotides, the nucleic acid sequences of which collectively represent the nucleic acid sequence encoding a classical HLA polypeptide (e.g., a nucleic acid sequence encoding a specific HLA-A allele (e.g., HLA-A*0101 or HLA-A*0201)). As used herein, the term "non-classical HLA oligo subset" refers to a collection of capture oligonucleotides, the nucleic acid sequences of which collectively represent the nucleic acid sequence encoding a non-classical HLA polypeptide (e.g., a nucleic acid sequence encoding a specific HLA-E allele (e.g., HLA-E* 0101 or HLA-E* 0103)). Similarly, the term "accessory molecule oligo subset" refers to a collection of capture oligonucleotides, the nucleic acid sequences of which collectively represent the nucleic acid sequence encoding a target accessory molecule polypeptide; the term "KIR oligo subset" refers to a collection of capture oligonucleotides, the nucleic acid sequences of which collectively represent the nucleic acid sequence encoding a target KIR polypeptide; and the term "blood group determining oligo subset" refers to a collection of capture oligonucleotides, the nucleic acid sequences of which collectively represent the nucleic acid sequence encoding a target blood group determining polypeptide.

The term, "collectively target(s)" with reference to a set of capture oligonucleotides, means that, taking the entire set together, the nucleic acid sequences of the set are complementary to the full length nucleic acid sequence of their target.

As used herein, the terms "KIR polypeptide phenotype" refers to a specific set of KIR alleles expressed by a sample (e.g., cell), as determined according to the methods described herein.

As used herein, the term "blood group phenotype" refers to the specific blood group of a sample (e.g., cell), including ABO (ABO), Chido Rodgers (CH/RG), Colton (CO), Cromer (CROM), Diego (DI) (band 3), Dombrock (DO), Duffy (DARC), Gerbich (Ge), Gill (GIL), Globoside and Pk, H(H), I (I), Indian (IN), John Milton Hagen (JMH), Kell (KEL) and Kx (XK), Kidd (JK), Knops (KN), Landsteiner-Wiener (LW), Lewis (LE), Lutheran (LU), MNS (MNS)

(Glycophorins A, B and E), Ok (OK), Raph (RAPH), Rh (RH) and Rh-gp (RHAG), Scianna (SC), T/Tn, Xg (XG), and Yt (YT), as determined according to the methods described herein. The term can also, but does not necessarily, encompass a blood group subtype, such as subtype A1 or A2.

As used herein, the term "deriving donor/recipient transplant compatibility" means determining whether a tissue (cell, organ, skin, etc.) from a potential donor is suitable for transplantation into a recipient. Typically, a suitable donor will have an HLA tissue type that is compatible (i.e. the same or highly similar) to that of the transplant recipient.

"Polypeptide" and "protein" are used interchangeably and mean any peptide-linked chain of amino acids, regardless of length or post-translational modification.

As used herein, the term "allele" refers to a specific version of a nucleotide sequence of a polymorphic gene.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, probe and amplification product.

As used herein, the term "capture oligonucleotide" refers to a nucleic acid sequence that specifically hybridizes to a target nucleic acid sequence (e.g., cDNA or cRNA). A capture oligonucleotide is intended to be hybridized to a solid support (e.g., microarray slide) for the detection of the presence of a particular target sequence (e.g., cDNA or cRNA). One of skill will recognize that the precise sequence of the particular capture oligonucleotides described herein can be modified to a certain degree to produce capture oligonucleotides that are "substantially identical" to the disclosed capture oligonucleotides, but retain the ability to specifically bind to (i.e., hybridize specifically to) the same targets or samples as the capture oligonucleotide from which they were derived. Such modifications are specifically covered by reference to the individual capture oligonucleotides described herein.

The word "sample" may be used herein to refer not only to detected nucleic acids, but to the detectable nucleic acids in the form in which they are applied to the target.

The terms "probe", "detection probe", or "nucleic acid probe", as used herein, are defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. Alternatively, the probes of the present invention are synthesized and have sequences corresponding to a source of nucleic acids. The probes of the present invention correspond to or are produced from nucleic acids found in the regions described herein. The probe or genomic nucleic acid sample may be processed in some manner, e.g., by removal of repetitive nucleic acids or enrichment with unique nucleic acids. "Probe signal" means the level of fluorescence measured (e.g., by optical scanner) from hybridized oligonucleotides on the array.

One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

The terms "nucleic acid array," "array" and "microarray", as used herein, refer to a plurality of nucleic acid molecules (capture oligonucleotides) immobilized on a solid surface (e.g., nitrocellulose, glass, quartz, fused silica slides and the like) to which sample nucleic acids (e.g., cDNA or cRNA) are hybridized. The nucleic acids may contain sequence from specific genes or clones, such as the capture oligonucleotides of the invention, as disclosed herein. Other capture oligonucleotides optionally contain, for instance, reference sequences. The capture oligonucleotides of the arrays may be arranged on the solid surface at different densities. The capture oligonucleotides densities will depend upon a number of factors, such as the nature of the label, if any, the solid support, and the like.

An "isolated nucleic acid molecule" (e.g., isolated cDNA) is either (1) a nucleic acid molecule that contains sequence not identical to that of any naturally occurring sequence, or (2), in the context of a nucleic acid molecule with a naturally-occurring sequence (e.g., a cDNA, cRNA or genomic DNA), a nucleic acid molecule free of at least one of the genes that flank the gene containing the nucleic acid molecule of interest in the genome of the organism in which the gene containing the nucleic acid molecule of interest naturally occurs. The term also includes a separate molecule such as: a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a nucleic acid molecule encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein. It will be apparent from the foregoing that an isolated nucleic acid molecule does not mean a nucleic acid molecule present among hundreds to millions of other nucleic acid molecule molecules within, for example, cDNA or genomic DNA libraries or genomic DNA restriction digests in, for example, a restriction digest reaction mixture or an electrophoretic gel slice.

The term "subject" means any animal, including mammals and, in particular, humans.

Human Leukocyte Antigen (HLA) Polypeptides

The human major histocompatibility genes are among the most polymorphic genes in the human genome. HLA antigens are encoded by a series of closely linked genes located at the position p21 on chromosome 6. Genes of the HLA region span approximately 4 million bases of DNA, and are clustered into three distinct regions designated class I, class II and class III. Genes within the class I and class II regions share structural and functional properties and are considered to be part of the immunoglobulin gene super family. Although distinct in sequence and structure, both class I and class II genes encode proteins that are critical in controlling T-cell recognition and determining histocompatibility in marrow transplantation (Rammensee, Curr. Opin. Immunol. 7:85-96 (1995)).

At least 17 loci including several pseudogenes exist in the HLA class I region. Three of these loci encode HLA-A, -B and -C alloantigens that constitute the major class I determinants The HLA-A, -B and -C loci show a striking degree of sequence and structural homology with one another and genes at all three loci are highly polymorphic (Bodmer et al., Tissue Antigens 49:297-321 (1997)). Currently, more than 1,193 HLA-A, 1,799 HLA-B and 829 HLA-C alleles have been described worldwide, and in the U.S. alone, more than 9.7 million different haplotype combinations have been estimated (Maiers et al., Hum Immunol 2007; 68:779-88). More recently, three additional class I genes, HLA-E (9 alleles), -F (21 alleles) and -G (46 alleles), have been defined (Lee et al., Eur J. Immunol. 40:2308-18. (2010); Geraghty et al., Proc. Natl. Acad. Sci. USA 84:9145-49. 54 (1987); Koller et al., J. Immunol. 141:897-904 (1988)).

Class II genes are divided into five families, designated DR, DQ, DO, DM and DP, based on their degree of sequence homology and their location within the HLA-D region. The HLA class II region is comprised of nine distinct genes: DRA, DRB1, DRB3, DRB4, DRB5, DQA, DQB, DPA and DPB. As with class I genes, class II DR, DQ and DP genes show a striking degree of polymorphism, with more than 805 alleles thus far defined at the DRB1 locus (Marsh S G, Hum Immunol, (2010)).

In certain embodiments, the microarrays described herein detect expression of non-classical HLA molecules. Examples of non-classical HLA molecules include without limitation, CD1a-c, CD1d, HLA-E, HLA-G, HLA-H, HLA-J, HLA-K, HLA-L, DM, DOα, DOβ, ULBP, EPCR, MR1, FcRn, HFE, ZAG, and MIC. Preferably, the non-classical HLA molecules detected by the arrays provided herein include at least HLA-E, HLA-F, HLA-G, DM, DO and MIC, although a greater or fewer number of non-classical HLA targets can be included on the arrays.

Role of HLA in Infectious Disease

When a foreign pathogen enters the body, antigen-presenting cells (APCs) engulf the pathogen through a process called phagocytosis. Proteins from the pathogen are digested into peptides and loaded onto HLA molecules (specifically MHC class II). The peptides are then displayed by the APCs to T cells, which then produce a variety of effects to eliminate the pathogen. Through a similar process, proteins (both native and foreign, such as the proteins of viruses) produced inside most cells are displayed on HLA antigens (specifically MHC class I) on the cell surface. Infected cells can be recognized and destroyed by components of the immune system (specifically CD8+ T cells).

Peptides, such as, e.g., infection or disease-related peptides fit into the binding clefts of HLA molecules, and, in these configurations, peptides are presented to T cells. The T cells are restricted by the HLA molecules when certain peptides are within the binding cleft. Each HLA molecule, however, is limited in the number of peptides (e.g. disease or infection related peptides) that it can bind. Thus, an individual's specific combination of different HLA molecules (i.e., "HLA tissue type"), which increases the peptide binding repertoire, is important for how an individual's immune system can respond to infection. The ability to precisely characterize an individual's HLA tissue type can therefore facilitate understanding of how an individual's immune system can respond to a particular infection. A large number of studies have reported correlation with specific HLA profiles and susceptibility to or severity of disease.

Role of HLA in Graft Rejection

Transplant rejection occurs when a transplanted organ or tissue is not accepted by the body of the transplant recipient, typically because the transplanted organ or tissue is recognized by the recipient's immune system as non-self. Any cell displaying an HLA type not expressed by the recipient is recognized as "non-self", resulting in the rejection of the tissue bearing those cells. Thus, it is imperative that tools and methods for carrying out HLA tissue typing with precision and efficiency in order to quickly determine whether a potential donor has an HLA tissue type that is compatible with that of a recipient.

Role of HLA in Autoimmunity

HLA types are inherited, and some of them are connected with autoimmune disorders and other diseases. People with certain HLA tissue types are more likely to develop certain autoimmune diseases, such as Type I Diabetes, Rheumatoid arthritis, Ankylosing spondylitis, Celiac Disease, SLE (Systemic Lupus Erythematosus), Myasthenia Gravis, inclusion body myositis and Sjögren's syndrome. For example, in Celiac disease, HLA tissue typing is the only effective means of discriminating between $1^{st}$ degree relatives who are at risk from those who are not, prior to the appearance of sometimes irreversible symptoms such as allergies and secondary autoimmune disease. For HLA typing to lead to some improvement and acceleration in the diagnosis of Celiac Disease and Type 1 diabetes, DQ2 typing is necessary. However, for DQ2 typing to be useful it requires either high resolution B1*typing (resolving *0201 from *0202), DQA1*typing, or DR serotyping. Thus, the arrays provided herein, which provide high resolution typing of classical HLA polypeptides, and preferably, all known classical HLA polypeptides, are useful for diagnosing such disorders.

Role of HLA in Cancer

Some HLA mediated diseases are directly involved in the promotion of cancer. For example, gluten sensitive enteropathy is associated with increased prevalence of enteropathy-associated T-cell lymphoma, and DR3-DQ2 homozygotes are within the highest risk group with close to 80% of gluten sensitive EATL cases. Thus, the arrays provided herein are useful in diagnosing, e.g., an individual's risk of developing cancer based on the assigned HLA tissue type of the individual (see, e.g., Luigi De Petris, et al. Medical Oncology, Volume 21, Number 1, 49-52, DOI: 10.1385/MO:21:1:49; Lin P, et al. Cancer Epidemiol Biomarkers Prev. 2001 October; 10(10):1037-45; Michallet et al, Leukemia. 10:1725-31, (2010)).

Accessory Molecules

In certain embodiments, the microarrays described herein can detect expression of accessory molecules important in HLA-linked peptide presentation and/or antigen processing, including, for example, and without limitation, LMP2, LMP7, LMP10, tripeptidyl peptidase II (TPPII), bleomycin hydrolase (BLMH), leucine aminopeptidase 3 (LAP3), transporter associated with antigen processing (TAP) 1, TAP2, β2-microglobulin, TAP binding protein (tapasin), calnexin (CANX), calreticulin (CALR), protein disulfide isomerase family A member 2 (PDIA2), protein disulfide isomerase family A member 3 (PDIA3), ERp57, endoplasmic reticulum aminopeptidase (ERAP) 1, ERAP2, proteasome (prosome macropain) subunit althap (PSMA) type I (PSMA1), PSMA2, PSMA3, PSMA4, PSMA5, PSMA6, PSMA7, PSMA8, proteasome (prosome macropain) subunit beta (PSMB) type 1 (PSMB1), PSMB2, PSMB3, PSMB4, PSMB5, PSMB6, PSMB7, PSMB8, PSMB9, PSMB10, PSMB11, proteasome (prosome macropain) 26S subunit ATPase (PSMC) 1 (PSMC1); PSMC2, PSMC3, PSMC4, PSMC5, PSMC6, proteasome (prosome macropain) 26S subunit non-ATPase (PSMD) 1 (PSMD1), PSMD2, PSMD3, PSMD4, PSMD5, PSMD6, PSMD7, PSMD8, PSMD9, PSMD10, PSMD11, PSMD12, PSMD13, and PSMD14. These molecules are summarized by the following nomenclature: CANX, ERAP1-2, B2M, CALR, PDIA2,3, PSMA1-8, PSMB1-11, PSMC1-6, PSMD1-14, TAP1,2, TAPBP, TPP2, BLMH, and LAP3.

In a preferred embodiment, the arrays provided herein can simultaneously determine HLA tissue type and an accessory molecule phenotype (expression of one or more accessory molecules important in peptide loading and/or antigen processing) in a single assay (e.g. on a single microarray slide). However, in other embodiments, the array specific for detecting expression of such accessory molecules can be carried out separately (e.g., on a separate microarray slide and/or in a separate assay). Within one embodiment, arrays comprising both HLA oligonucleotides (classical and/or non-classical HLA oligonucleotides) and accessory molecule oligonucleotides targeting, e.g., the accessory molecules described above, are useful for determining donor/recipient transplant compatibility.

Within other embodiments, such combined HLA/accessory molecule arrays are useful for diagnosing or predicting the likelihood of an HLA-linked genetic defect, disease, inadequate or undesirable response to a vaccine, biologic treatment (recombinant protein, biosimilar or equivalent), or infectious organism, or condition in a subject, wherein the step is based on one or more assigned HLA tissue types (including classical and/or non-classical HLA alleles) and an accessory molecule phenotype.

Within other embodiments, such combined HLA/accessory molecule arrays are useful for determining the likely response of a subject to a particular treatment regimen selected from the group consisting of: bone marrow transplantation, immunosuppressive regimen, antiviral drug regimen, antiviral drug resistance, antiretroviral drug regimen, and autoimmunity drug regimen, wherein the step is based on one or more assigned HLA tissue types (including classical and/or non-classical HLA alleles) and an accessory molecule phenotype.

Within other embodiments, such combined HLA/accessory molecule arrays are useful for determining whether the subject is likely to develop antiretroviral drug resistance or cancer drug regimen resistance, wherein the step is based on one or more assigned HLA tissue types (including classical and/or non-classical HLA alleles) and an accessory molecule phenotype.

Killer-cell Immunoglobulin-Like Receptor (KIR) Molecules

Killer-cell immunoglobulin-like receptors (KIR molecules) are a family of cell surface proteins found on natural killer (NK) cells. KIR molecules regulate the killing function of NK cells by interacting with MHC class I molecules, which are expressed on all cell types. This interaction allows them to detect virally infected cells or tumor cells that have a characteristic low level of Class I MHC on their surface. Most KIR molecules are inhibitory, meaning that their recognition of MHC suppresses the cytotoxic activity of the NK cell. Only a limited number of KIRs have the ability to activate cells. KIR genes are highly polymorphic, so that different individuals possess different arrays/repertoires of KIR genes. The polymorphic KIR genes are found in a cluster on chromosome 19q13.4 within the 1 Mb leukocyte receptor complex (LRC). The gene content of the KIR gene cluster varies among haplotypes, although several "framework" genes are found in all haplotypes (KIR3DL3, KIR3DP1, KIR3DL4, KIR3DL2). The KIR proteins are classified by the number of extracellular immunoglobulin domains (2D or 3D) and by whether they have a long (L) or short (S) cytoplasmic domain. KIR proteins with the long cytoplasmic domain transduce inhibitory signals upon ligand binding via an immune tyrosine-based inhibitory motif (ITIM), while KIR proteins with the short cytoplasmic domain lack the ITIM motif and instead associate with the TYRO protein tyrosine kinase binding protein to transduce activating signals. The ligands for several KIR proteins are subsets of HLA class I molecules; thus, KIR proteins are thought to play an important role in regulation of the immune response.

KIR involvement in tissue transplant has been reported. Specifically, it has been reported that certain combinations of HLA and KIR haplotypes may affect outcome in T-cell depleted haematopoietic stem cell transplantation (HSCT) (Chen, C. et al. Bone Marrow Transplantation (2006) 38, 437-444). Thus, the determination of the KIR phenotype of an individual can be useful for determining donor/recipient transplant compatibility. Examples of KIR molecules, the expression of which can be determined by the assays and method provided herein, include without limitation, KIR 2DL1, 2DL2, 2DL3, 3DL1, 3DL2, 2DS1, 2DS2, 2DS3, 2DS4, 2DS5, and 3DS1. Furthermore, within certain embodiments, the present arrays provide the ability to simultaneously determine both HLA tissue type and KIR haplotype of a sample on a single array, which provides a highly efficient and informative assay for determining donor/recipient compatibility, in addition to other diagnostic uses. For example, within certain embodiments, such combined HLA/KIR polypeptide arrays are useful for diagnosing or predicting the likelihood of an HLA-linked genetic defect, disease, inadequate or undesirable response to a vaccine, biologic treatment (recombinant protein, biosimilar or equivalent), or infectious organism, or condition in a subject, wherein the step is based on one or more assigned HLA tissue types (including classical and/or non-classical HLA alleles) and a KIR phenotype.

Within other embodiments, such combined HLA/KIR polypeptide arrays are useful for determining the likely response of a subject to a particular treatment regimen selected from the group consisting of: bone marrow transplantation, immunosuppressive regimen, antiviral drug regimen, antiviral drug resistance, antiretroviral drug regimen, and autoimmunity drug regimen, wherein the step is based on one or more assigned HLA tissue types (including classical and/or non-classical HLA alleles) and a KIR phenotype.

Within other embodiments, such combined HLA/KIR polypeptide arrays are useful for determining whether the subject is likely to develop antiretroviral drug resistance or cancer drug regimen resistance, wherein the step is based on one or more assigned HLA tissue types (including classical and/or non-classical HLA alleles) and KIR phenotype.

Blood Group Determining Molecules

Distinct molecules called agglutinogens are attached to the surface of red blood cells. There are two different types of agglutinogens, type "A" and type "B". Each type has different properties. The ABO blood type classification system uses the presence or absence of these molecules to categorize blood into four types: A, B, AB, and O. In each individual, two alleles encoding the enzymes responsible for determining blood group antigens are inherited, one from each parent. The possible combinations of alleles produce blood types in the following way: AA, AB, AO, BA BB, BO, OA, OB, OO. The A and B antigen molecules on the surface of red blood cells are produced by two different enzymes. These two enzymes are encoded by different versions, or alleles, of the same gene: A and B.

The A and B alleles code for enzymes that produce the type A and B antigens respectively. The A allele encodes a glycosyltransferase that bonds α-N-acetylgalactosamine to the D-galactose end of the H antigen, producing the A antigen. The B allele encodes a glycosyltransferase that joins α-D-galactose bonded to the D-galactose end of the H antigen, creating the B antigen. A third version of this gene, the O allele, contains a deletion of a single nucleotide (guanine at position 261 in exon 6), which results in loss of enzymatic activity of the encoded protein, thereby leading to failure to modify the H antigen.

Another level of specificity is added to blood type by examining the presence or absence of the Rh protein. Each blood type is either positive "+" (has the Rh protein) or negative "−" (no Rh protein). For example, a person whose blood type is "A positive" (A +), has both type A and Rh proteins on the surface of their red blood cells.

Determining the blood type of a sample, in addition to the HLA tissue type can be useful, e.g., for the determination of donor/recipient compatibility for e.g., tissue transplant. The arrays provided herein provide an efficient method for simultaneously determining both HLA tissue type and blood group in a single assay. In the transplant field, in particular, it is critical that donor/recipient compatibility results be obtained as quickly and cost-efficiently as possible, and the efficiency of the arrays provided herein address that need.

Further, the A, B and O blood types also contain subgroups. For example, there are six common alleles in white individuals of the ABO gene that produce one's blood type, including A101 (A1), A201 (A2), B101 (B1), O01 (O1), O02 (O1v), and O03 (O2). The different blood groups, and in some cases specific subgroups, can be associated with different diseases, and thus, determining the specific allele of a cell can be important for determining disease susceptibility. For example, O group compared to non-O group (A, AB, and B) individuals have a 14% reduced risk of squamous cell carcinoma and 4% reduced risk of basal cell carcinoma. O group is also associated with a reduced risk of pancreatic cancer. Further, the B antigen is linked with increased risk of ovarian cancer, and gastric cancer has been reported to be more common in blood group A and least in group O.

Non-limiting examples of blood group determining molecules that can be determined according to the arrays and methods provided herein include ABO (ABO), Chido Rodgers (CH/RG), Colton (CO), Cromer (CROM), Diego (DI) (band 3), Dombrock (DO), Duffy (DARC), Gerbich (Ge), Gill (GIL), Globoside and Pk, H (H), I (I), Indian (IN), John Milton Hagen (JMH), Kell (KEL) and Kx (XK), Kidd (JK), Knops (KN), Landsteiner-Wiener (LW), Lewis (LE), Lutheran (LU), MNS (MNS, Glycophorins A, B and E), Ok (OK), Raph (RAPH), Rh (RH) and Rh-gp (RHAG), Scianna (SC), T/Tn, Xg (XG), and Yt (YT).

Within certain embodiments, the characterization of blood group determining molecules by the arrays and methods provided herein are useful, e.g., in the context of blood transfusions. Prior to blood transfusion, the compatibility of the blood donor and recipient is dependent upon the blood group factors mentioned above. Compatibility is a clinical necessity due to the fatal consequences of blood agglutination which can result from incompatibility. By determining these factors of both donor and recipient using the array and methods herein, compatible donors can be selected.

Solid Supports

The solid supports, e.g., microarray slides, used in the present invention may be biological, nonbiological, organic, inorganic, or a combination of any of these, existing as particles, strands, precipitates, gels, sheets, tubing, spheres, containers, capillaries, pads, slices, films, plates, slides, etc. The solid support is preferably flat but may take on alternative surface configurations. For example, the solid support may contain raised or depressed regions on which synthesis takes place. In some embodiments, the solid support will be chosen to provide appropriate light-absorbing characteristics. For example, the support may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface Si—OH functionalities, such as are found on silica surfaces.

Linking Groups

Attached to the solid support is an optional spacer or linking group. The spacer molecules are preferably of sufficient length to permit the capture oligonucleotides in the completed array to interact freely with molecules exposed to the array. The spacer molecules, when present, are typically 6-50 atoms long to provide sufficient exposure for the attached probes. The spacer will typically be comprised of a surface attaching portion and a longer chain portion. The surface attaching portion is that part of the linking group or spacer which is directly attached to the solid support. This portion can be attached to the solid support via carbon-carbon bonds using, for example, supports having (poly)trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The surface attaching groups will also have a site for attachment of the longer chain portion. For example, groups which are suitable for attachment to a longer chain portion would include amines, hydroxyl, thiol, and carboxyl. Preferred surface attaching portions include aminoalkylsilanes and hydroxyalkylsilanes. In particularly preferred embodiments, the surface attaching portion of the linking group is either aminopropyltriethoxysilane or aminopropyltrimethoxysilane.

The longer chain portion can be any of a variety of molecules which are inert to the subsequent conditions necessary for attaching the oligonucleotide probes, or for hybridization of a sample to the oligonucleotide array. These longer chain portions will typically be ethylene glycol oligomers containing 2-14 monomer units, diamines, diacids, amino acids, peptides, or combinations thereof. In some embodiments, the longer chain portion is a polynucleotide (e.g., a 15-mer of poly dT). Additionally, for use in synthesis of the oligonucleotide arrays, the linking group will typically have a protecting group, attached to a functional group (i.e., hydroxyl, amino or carboxylic acid) on the distal or terminal end of the chain portion (opposite the solid support). After deprotection and coupling, the distal end is covalently bound to a capture oligonucleotide (e.g., an HLA-A capture oligonucleotide).
Synthesis of Oligonucleotide Arrays on Solid Supports The attachment of nucleic acids or oligonucleotide molecules to solid supports to create highly dense patterns of diverse capture oligonucleotides on a single surface has been demonstrated by, for example, Maskos and Southern (Nuc. Acids. Res. 20:1679-1684 (1992)), Blanchard and Hood (Bioelectronics 11:687-690 (1996)), and Fodor et al. (Science 251:767-773 (1991)). For example, two methodologies that have been used to synthesize oligonucleotide arrays are described by Saiki et al. (Proc. Natl. Acad. Sci. USA. 86:6230-6234 (1989)) and Chrisey et al. (Nuc. Acids Res. 24:3040-3047 (1996)). Presynthesized capture oligonucleotides can be delivered to a solid support by high-speed robotics, and then immobilized on the surface. The resolution of the resulting oligonucleotide array is determined by both the spatial resolution of the delivery systems and the physical space requirement of the delivered oligonucleotide solution volume. The surface density of the immobilized capture oligonucleotides varies greatly with different solid surface and linkage chemistries (Guo, et al., Nuc. Acids Res. 22:5456-5465 (1994); Fahy, et al., Nuc. Acids Res. 21:1819-1826 (1993); Wolf, et al., Nuc. Acids Res. 15:2911-2926 (1987); and Ghosh, et al., Nuc. Acids Res. 15:5353-5372 (1987)).

In another approach, capture oligonucleotides are synthesized directly onto the solid support, nucleotide by nucleotide, through a series of coupling and deprotection steps. Both conventional solid-phase oligonucleotide synthesis methods and light-directed combinatorial synthesis methods have been successfully applied in this in situ fabrication process (Fodor et al., supra (1991) and Gilham, Biochemistry 7:2809-2813 (1968)). High reaction yields in both the coupling and the deprotection steps are critical for the success of in situ synthesis. The preparation of in situ arrays can be automated and thereby increase the complexity of the array compared to the use of presynthesized oligonucleotides.

a) Spatially-Resolved Attachment Chemistry

Preferably, a capture oligonucleotide is immobilized onto a solid support through a single covalent bond. Gilham (Biochemistry, 7:2809-2813 (1968)), for example, described the attachment of DNA molecules to paper using carbodiimide via the 5'-end terminal phosphate group. Suitable supports for covalent immobilization of DNA include glass, acrylamide gel, latex particles, controlled pore glass, dextran supports, polystyrene matrices and avidin-coated polystyrene beads and have been described (Guo, et al., Nuc. Acids Res. 22:5456-5465 (1994); Fahy, et al., Nuc. Acids Res. 21:1819-1826 (1993); Wolf, et al., Nuc. Acids Res. 15:2911-2926 (1987); Ghosh, et al., Nuc. Acids Res. 15:5353-5372 (1987); Gingeras et al., Nuc Acids Res. 15:5773-5790 (1987); Rasmussen et al., Anal. Biochem. 198:138-142 (1991); and Lund et al., Nuc. Acids Res. 16:10861-10880 (1988)). Several other solid supports, such as nitrocellulose and nylon membranes were employed for oligonucleotide immobilization using UV-activated DNA-surface cross-linking chemistry (Meinkoth and Wahl, Anal. Biochem. 138:267-284 (1984)). However, in these cases, DNA molecules were non-covalently bound to the surface at multiple sites, hampering reproducibility and stability.

Fodor, et al. (supra, (1991)) demonstrated the use of photolithographic technology to synthesize high-density oligonucleotide arrays on silicon substrates. In this process, crosslinkers are first made by exposing a photochemically-labile organosilane surface to UV light. The resulting pattern is then reacted with heterobifunctional crosslinking molecules. The oligonucleotide molecules are then bound to these crosslinkers to form a well-defined DNA pattern on the surface. Spatial resolution of 1 micron per DNA spot is feasible using this approach.

Three-dimensional immobilization matrices have been developed to increase capacity and are contemplated for use for the array provided herein. Yershor, et al. (Genetics 93:4913-4918 (1996)), for example, have produced DNA arrays by immobilizing oligonucleotides in acrylamide gel at a density of 20,000 to 30,000 different capture oligonucleotides per $cm^2$, two orders of magnitude higher than the capacity of two-dimensional supports, with density increasing as technology advances. The three-dimensional support permits high oligonucleotide loading and enhanced hybridization. However, because only short oligonucleotides can diffuse into gel matrix, the application of this approach is limited.

b) Spatially Addressable Parallel Chemical Synthesis

Solid phase DNA synthesis can be accomplished with a number of different chemistries. Froehler et al. (Nuc. Acids Res. 14:5399-5407 (1986) and McBride and Caruthers (Tetrahedron Lett. 24:245-248 (1983) have demonstrated solid phase DNA synthesis chemistries utilizing H-phosphonate and phosphoramidites, which covalently attach an organic linker molecule to a surface and build the oligonucleotide off the terminus of the linker through successive coupling and deprotection steps.

Based on this scheme, two distinct approaches have been developed to construct surface-bound oligonucleotide arrays. One approach (Fodor, et al., supra (1991)) combines solid-phase DNA synthesis with semiconductor-based photolithography. The major advantage of this approach is the potential to synthesize very high-density arrays comprised of 50 micron spots or less. However, the major drawback to this approach is the need for a photolithographic mask for each unique array of oligonucleotides. For example, an array of 25-mers would require 100 different masks. The expense of synthesizing these arrays is proportional to the number of unique masks.

Microfabricated ink-jet pumps, similar to those used in certain ink-jet printers to deliver synthesis reagents onto the surface of a solid support can also be used. Within this method, the surface is scanned across a set of ink-jet pumps using a computer-controlled x-y translation stage. In each coupling step, DNA monomers are delivered to the defined area at rates of several hundred drops per second.

Each of these in situ approaches permits large numbers of arrays of unlimited combinatorial matrices to be made in fairly few steps.

It is to be understood that the oligonucleotide arrays described herein can be prepared according to the above-described methods or according to any other suitable method known in the art.

In one embodiment, oligonucleotide arrays can be prepared by:

(a) contacting a solid support with an aminoalkyltrialkoxysilane in the vapor phase at reduced pressure to form an aminoalkylsilane-derivatized solid support;

(b) contacting the aminoalkylsilane-derivatized solid support with a linking group to covalently attach the linking group to the aminoalkylsilane-derivatized solid support to form a linking group-modified solid support; and (c) attaching a plurality of capture oligonucleotides to the linking group-modified solid support to form the array of covalently-attached oligonucleotide probes.

The solid supports can be any of those described above which are conveniently derivatized with a vapor phase deposition of an aminoalkyltrialkoxysilane. The aminoalkyltrialkoxysilanes useful in this aspect of the invention are any of those that can be utilized in the vapor phase at temperatures of from about ambient temperature to about 150° C. at pressures of from about 760 mmHg to about 0.1 mmHg. Typically, the aminoalkyl portion of the silane will be aminopropyl, aminoethyl or aminomethyl. The trialkoxysilane portion can be one in which the alkoxy groups are all the same (e.g., trimethoxysilane, triethoxysilane) or one in which the alkoxy groups are not all alike (e.g., dimethoxyethoxysilane). Accordingly, the aminoalkyltrialkoxysilane will typically be selected from aminopropyltrimethoxysilane, aminopropyltriethoxysilane, aminopropyldiethoxy-methoxysilane, aminoethyltrimethoxysilane, and the like. More preferably, the aminoalkyltrialkoxysilane is aminopropyltrimethoxysilane.

As indicated above, a more uniform coating of amino groups on the solid support can be achieved by applying an aminoalkyltrialkoxysilane in the vapor phase, typically at reduced pressure. This can be accomplished by placing the solid support into a vacuum chamber, evacuating the chamber, and introducing the silane. In some embodiments, the vacuum chamber can be heated to facilitate silane vaporization and even coating of the solid support. For example, when aminopropyltrimethoxysilane is used, the pressure will typically be from about 5 to 35 mmHg and the vacuum chamber will be heated to a temperature of from about 60 to about 110° C. After a period of time sufficient for formation of an aminoalkylsilane-derivatized solid support, the support is removed from the vacuum chamber and rinsed to remove any unbound spacer.

The resultant support can then be contacted with a suitable amount of a linking group to covalently attach the linking group to the aminoalkylsilane-derivatized solid support. In some embodiments, the aminoalkylsilane-derivatized solid support will first be treated with a reagent capable of facilitating linking group attachment to the derivatized support. A variety of reagents are useful in this aspect of the invention including diisocyanates, diisothiocyanates, dicarboxylic acids (and their activated esters), and the like. Particular preferred are diisothiocyanates (e.g., 1,4-phenylenediisothiocyanate).

Once the solid support has been suitably derivatized, a linking group is attached to provide a spacing between the oligonucleotide probe and the support which is optimized for interactions between the probes and the sample. As provided above, a variety of linking groups can be used in this aspect of the invention. Preferred groups are those that provide a spacing similar to that provided by a 15-mer poly dT spacing group. Additionally, the linking group will have a reactive portion that is selected to be compatible with the amino group of the aminoalkylsilane-derivatized support, or with the functional group present on the reagent used to facilitate linking group attachment (e.g., the isothiocyanate portion of 1,4-phenylenediisothiocyanate). Accordingly, at the proximal end (that forming an attachment closest to the support), the linking group will have a functional group that is reactive with an amino moiety (e.g., a carboxylic acid, anhydride, isothiocyanate, and the like) or a functional group that is reactive with an isocyanate, isothiocyanate or carboxylic acid moiety (e.g., an amino group, a hydroxyl group or the like).

In one embodiment, the support is derivatized first with aminopropyltrimethoxysilane, followed by attachment of 1,4-phenylenediisothiocyanate, followed by attachment of a 15-mer oligonucleotide, preferably a 15-mer of poly-dT.

Following constriction of the linking group-modified solid support, a plurality of capture oligonucleotides is attached to form an array of covalently-attached capture oligonucleotides. In this aspect of the invention, the capture oligonucleotides can be any collection of nucleic acids or polymer. Preferably, the capture oligonucleotides are those that represent one or more of the groups selected from all known classical HLA polypeptides, all known non-classical HLA polypeptides, accessory molecules important in antigen processing and presentation, KIR polypeptides, and blood group determining polypeptides. The capture oligonucleotides are typically 17 to 60 nucleotides in length, although shorter or longer sequences are also contemplated, so that each has a melting temperature ($T_m$) with respect to its exact complement of about 64° C. (e.g., about 64.0, 64.1, 64.2, 64.3, 64.4, 64.5 or 64.6° C.). In a specific embodiment, the preferred Tm is about 64.3. Preferred capture oligonucleotides have the nucleic acid sequences set forth in Tables I-V, below. The capture oligonucleotides can be prepared by any conventional methods known to those of skill in the art. Alternatively, the oligonucleotides can be constructed on the array using the techniques described above (e.g., photolithography, flow channel, ink jetspotting, and the like). In preferred embodiments, the oligonucleotides are constructed using conventional solution or solid phase chemistry, and then attached to the array's solid support component (e.g., slide).

Construction of the present arrays is preferably carried out in a manner that ensures that the capture oligonucleotides are present at a surface density of about 250 to about 450 angstrom$^2$/molecule, preferably about 325 to about 375 angstrom$^2$/molecule, or higher. Methods of measuring oligonucleotide density are well known to those of skill in the art.

Hybridization

Hybridization of DNA to a solid support has similar thermodynamic behavior compared to hybridization of DNA in solution. The stability of the double helix can be characterized by its melting temperature, which is strongly dependent upon oligonucleotide sequence and composition of the solvent (Wetmur, Crit. Rev. Biochem. & Mol. Bio. 26:227-259 (1991)). This strong-dependence of the duplex stability on oligonucleotide sequence, especially for short oligonucleotides, makes it difficult to design adequately stringent conditions for hybridization with oligonucleotide arrays, which usually vary widely in base composition. Thus, a large number of false positive or negative signals may occur when hybridization is performed on complex oligonucleotide arrays. Several approaches have been employed to eliminate the sequence-dependence of the stability of duplexes. Utilization of tetramethylammonium chloride (TMAC) in the hybridization solution is the most popular approach (Wood, et al., Proc. Natl. Acad. Sci. USA 82:1585-1588 (1985) and Riccelli and Benight, Nuc. Acids Res. 21:3785-3788 (1993)). TMAC was found to neutralize stability of duplexes imparted by sequences and allow the stringency of hybridization to be controlled as a function of probe length. Similar "isostabilization" function has also been described for other reagents (Rees, et al., Biochemistry 32: 137-144 (1993)).

The thermodynamic stability of solid-phase hybridization is also affected by differences between the perfectly matched duplex versus the mismatched duplex, which constitutes the fundamental limitation to sequence-specific recognition in hybridization. The binding of a capture oligonucleotide mismatched at a single base is compared with that of a perfectly matched capture oligonucleotide (i.e., its "exact complement"); the difference in duplex stability is used to identify the target sequence. In many cases, the differences in stability of a perfect match and a single-base mismatch are so small that discrimination between a perfect match and a single base mismatch cannot be achieved using common hybridization-washing procedures. Guo et al. described an approach to substantially increase the discrimination of single-base mismatches by using artificial mismatches (Guo et al., Nature Biotech. 15:331-335 (1997)). In this approach, an "artificial" mismatch is intentionally inserted into the capture oligonucleotide sequence, and the discrimination compares the stability of two mismatches versus one mismatch. An enhancement of the discrimination, as high as 200% of differential melting temperature, is generally achieved in hybridization with oligonucleotide arrays.

In vitro data indicate that nucleic acid hybridization in free solution and on surfaces is often a reaction rate-limited process. In a study of nitrocellulose membrane arrays, the hybridization kinetics was found to be proportional to the concentration of immobilized DNA. A mathematical model of hybridization on solid supports has been proposed that hypothesizes two different mechanisms by which nucleic acid targets can hybridize with immobilized oligonucleotide probes: direct hybridization from solution and hybridization by nucleic acid targets that adsorb nonspecifically on the surface and then diffuse to the capture oligonucleotides (Chan et al., Biophysical J. 69:2243-2255 (1995)). The hybridization rate depends strongly on both the nucleic acid diffusion constant in solution and the nucleic acid adsorption/desorption constant on surface.

Electric fields can be used to facilitate the diffusion of DNA targets to the immobilized capture oligonucleotides (Sosnowski et al., Proc. Natl. Acad. Sci. USA 94:1119-1123 (1997) and Cheng et al., Nature Biotech. 16:541-546 (1998)). In this system, oligonucleotide arrays are synthesized on the surface of a silicon electrode. Nucleic acid molecules, which have a large negative charge, can be moved in an electric field to an area of net positive charge and concentrate significantly on the electrode surface. The concentrating effect accelerates the hybridization of nucleic acid targets. Another advantage of this system is the reversibility of the hybridization in which non-specifically bound nucleic acid target molecules can be easily removed from the oligonucleotide arrays by reversing the polarity of the field.

Detection of Hybridization Events on Solid Supports

In certain embodiments, the nucleic acid sample (e.g., cDNA or cRNA) is directly labeled with a detectable marker. For example, cDNA or cRNA can be made from RNA obtained from a sample (e.g. blood or tissue) and fluorescent labels (e.g., dyes) can be incorporated into the cDNA or cRNA. In other embodiments, the nucleic acid samples themselves are not detectably labeled, but labeled detection probes are used that bind to target nucleic acids hybridized to capture oligonucleotides on the arrays.

Several methods for the detection of labeled nucleic acids or detection probes are currently available, of which the fluorescence-based methods are the most popular. Quantitative hybridization data available from these methods affords the advantages of rapid image analysis, direct comparison and digital archiving. Both the intensity of the fluorescent signal and the background depend strongly on environmental factors, such as dryness of the surface and the support materials. The influence of environmental factors on the strength of the signal and background mandates stringency for conditions and often precludes the use of highly fluorescent supports, such as nylon membranes.

In the analysis of complex genome systems, the use of multiple fluorescent dyes to simultaneously distinguish different nucleic acid molecules is an important methodologic advancement. Nucleic acid targets, including cDNA and cRNA and detection probes, in hybridization systems can be fluorescently labeled either directly or indirectly. The direct fluorescent label systems for nucleic acid molecules include derivatives of fluorescein and rhodamine dyes, which can be easily attached to the end of a nucleic acid strand.

Biotin is the most commonly used indirect fluorescent label. Biotin can be easily incorporated into nucleic acid molecules and detected using avidin or streptavidin by a covalently linked reporter group, such as alkaline phosphatase and horseradish peroxidase (Rees and Kurz, Nuc. Acids Res. 12:3435-3439 (1984)). The indirect nature of the biotin labeling method limits the applicability for quantitative analysis, but the sensitivity of biotin assays are as high as that which can be achieved using radioisotopes.

The fluorescence detection systems require that excess label be washed off; furthermore, after hybridization real-time monitoring of the hybridization process is not feasible. In order to observe ongoing hybridization events on the surface, surface-related detection methods have been developed. These methods are based on different optical phenomenon on the surface and can detect subtle changes such as the formation of nucleic acid duplexes on the surface, without interfering with the excess nucleic acid in solution. Duplex electron transfer, optical wave-guide, surface plasmon resonance and resonant mirror are a few examples of currently developed surface-based detection methods (Wood, Microchem. J. 47:330-337 (1993); Stimpson and Gordon, Biomolecular Engineering 13:73-80 (1996); Wats et al., Biosensor. Anal. Chem. 67:4283-4289 (1995); and Stimpson et al., Proc. Natl. Acad. Sci. USA 92:6379-6380 (1995)).

Oligonucleotide Arrays

Within certain embodiments, the present invention provides an array of capture oligonucleotides specific for nucleic acids encoding HLA polypeptides. The array is a useful tool for performing HLA tissue typing on a cell or tissue sample to determine, for example, whether a particular donor is suitable for matching in bone marrow, tissue (e.g., skin or organ) transplantation. Generally, the array will comprise a series of capture oligonucleotides which represent at least 80%, preferably at least 90%, more preferably at least 98%, and most preferably 100% of all known classical HLA polypeptides. In one embodiment, the array will comprise a series of capture oligonucleotides which represent at least 80%, preferably at least 90%, more preferably at least 98%, and most preferably 100% of all known non-classical HLA polypeptides. In one preferred embodiment, the arrays will represent all known non-classical HLA polypeptides. In another preferred embodiment, the arrays will represent all known classical HLA polypeptides and/or all known non-classical HLA polypeptides. The capture oligonucleotides are provided on the array at known or preselected positions to facilitate analysis. Additionally, the capture oligonucleotides are generally covalently attached to the solid support using a linking group that is sufficient to provide optimum binding of a sample nucleic acid to the oligonucleotide array.

Within certain embodiments, the above-described HLA oligonucleotide arrays (which can comprise capture oligonucleotides specific for either classical HLA polypeptides or non-classical HLA polypeptides or specific for both classical and nonclassical HLA polypeptides), further comprise negative control oligonucleotides.

Within other embodiments, the arrays provided herein comprise capture oligonucleotides that target nucleic acids encoding all known classical and non-classical HLA polypeptides, and, additionally or alternatively, comprise other capture oligonucleotides that target nucleic acids encoding other array targets, including but not limited to accessory molecules important in HLA-linked peptide presentation and/or processing, KIR polypeptides, and/or blood group determining polypeptides. In any of these arrays, negative control capture oligonucleotides can be optionally be included in the array, or can be included on a separate array (e.g., separate slide).

An important feature of the oligonucleotide arrays provided herein is the high redundancy (overlapping sequences offset by "walking" down the target nucleic acid sequences) of capture oligonucleotides. In one embodiment of the invention, capture oligonucleotides are designed to represent at least 80%, preferably at least 90% and more preferably at least 98% of the target polypeptide-encoding nucleic acid sequences (e.g., all classical and/or non-classical HLA polypeptides). Within certain embodiments, each oligonucleotide in a set of overlapping oligonucleotides is sequentially shifted by 1, 2, 3, 4, 5 or more nucleotides from the 5' end of the preceding overlapping oligonucleotide (i.e., each oligonucleotide contains a step 1, step 2, step 3, step 4, or step 5 shift from the preceding oligonucleotide in the set).

In order for the melting temperature of the capture oligonucleotide sequences to be comparable, capture oligonucleotides should be designed with careful attention to size, base composition, and placement of mismatched position within the hybridization sequence. Within certain embodiments, capture oligonucleotides can range in length from about 5 nucleotides (nt) to about 80 nt, about 7 nt to about 75 nt, about 10 nt to about 70 nt, about 15 nt to about 65 nt, or, preferably, about 17 nt to about 60 nt in length.

Within certain embodiments, the melting temperature ($T_m$) of the capture oligonucleotides (with respect to their exact complement) can range from about 64.3±0.7° C. In a preferred embodiment, all capture oligonucleotides have a Tm of about 64.3° C.

Within a specific embodiment, the oligonucleotide array comprises the capture oligonucleotides having the nucleic acid sequences set forth in Table I, below. The oligonucleotides in Table I are designed to collectively target transcripts (e.g., cDNA or cRNA) encoding target classical HLA molecules.

Within another specific embodiment, the oligonucleotide array comprises the capture oligonucleotides having the nucleic acid sequences set forth in Table II, below. The oligonucleotides in Table II are designed to collectively target transcripts (e.g., cDNA or cRNA) encoding non-classical HLA molecules.

Within yet another specific embodiment, the oligonucleotide array comprises the capture oligonucleotides having the nucleic acid sequences set forth in Table III, below. The oligonucleotides in Table III are designed to collectively target transcripts (e.g., cDNA or cRNA) encoding accessory molecules.

Within still another specific embodiment, the oligonucleotide array comprises the capture oligonucleotides having the nucleic acid sequences set forth in Table IV, below. The oligonucleotides in Table IV are designed to collectively target transcripts (e.g., cDNA or cRNA) encoding KIR polypeptides.

Within another specific embodiment, the oligonucleotide array comprises the capture oligonucleotides having the nucleic acid sequences set forth in Table V, below. The oligonucleotides in Table V are designed to collectively target transcripts (e.g., cDNA or cRNA) encoding blood group determining molecules.

The oligonucleotides set forth in Tables I-V, below, were designed to target the following alleles, however, it is to be understood that an array according to the present invention may also target other and/or additional alleles: A*01:01:01:01, A*01:01:02, A*01:01:03, A*01:01:04, A*01:01:05, A*01:01:06, A*01:01:07, A*01:01:08, A*01:01:09, A*01:01:10, A*01:01:11, A*01:01:12, A*01:01:13, A*01:01:14, A*01:01:15, A*01:01:16, A*01:01:17, A*01:01:18, A*01:01:19, A*01:02, A*01:03, A*01:06, A*01:07, A*01:08, A*01:09, A*01:10, A*01:12, A*01:13, A*01:14, A*01:17, A*01:19, A*01:20, A*01:21, A*01:23, A*01:24, A*01:25, A*01:26, A*01:28, A*01:29, A*01:30, A*01:32, A*01:33, A*01:35, A*01:36, A*01:37, A*01:38, A*01:39, A*01:40, A*01:41, A*01:42, A*01:43, A*01:44, A*01:45, A*01:46, A*01:47, A*01:48, A*01:49, A*01:50, A*01:51, A*01:54, A*01:55, A*01:58, A*01:59, A*01:60, A*01:61, A*01:62, A*01:63, A*01:64, A*01:65, A*01:66, A*02:01:01:01, A*02:01:01:03, A*02:01:02, A*02:01:03, A*02:01:04, A*02:01:05, A*02:01:06, A*02:01:07, A*02:01:08, A*02:01:09, A*02:01:10, A*02:01:11, A*02:01:12, A*02:01:13, A*02:01:14, A*02:01:15, A*02:01:17, A*02:01:18, A*02:01:19, A*02:01:21, A*02:01:22, A*02:01:23, A*02:01:24, A*02:01:25, A*02:01:26, A*02:01:27, A*02:01:28, A*02:01:29, A*02:01:30, A*02:01:31, A*02:01:32, A*02:01:33, A*02:01:34, A*02:01:35, A*02:01:36, A*02:01:37, A*02:01:38, A*02:01:39, A*02:01:40, A*02:01:41, A*02:01:42, A*02:01:43, A*02:01:44, A*02:01:45, A*02:01:46, A*02:01:47, A*02:01:48, A*02:01:49, A*02:01:50, A*02:02, A*02:03:01, A*02:03:02, A*02:03:03, A*02:04, A*02:05:01, A*02:05:02, A*02:05:03, A*02:06:01, A*02:06:02, A*02:06:03, A*02:06:04, A*02:06:05, A*02:06:06, A*02:06:07, A*02:06:08, A*02:06:09, A*02:07, A*02:08, A*02:09, A*02:10, A*02:101, A*02:102, A*02:103, A*02:104, A*02:105, A*02:106, A*02:107, A*02:108, A*02:109, A*02:11, A*02:110, A*02:111, A*02:112, A*02:114, A*02:115, A*02:116, A*02:117, A*02:118, A*02:119, A*02:12, A*02:120, A*02:121, A*02:122, A*02:123, A*02:124, A*02:126, A*02:127, A*02:128, A*02:129, A*02:13, A*02:130, A*02:131, A*02:132, A*02:133, A*02:134, A*02:135, A*02:136, A*02:137, A*02:138, A*02:139, A*02:14, A*02:140, A*02:141, A*02:142, A*02:143, A*02:144, A*02:145, A*02:146, A*02:147, A*02:148, A*02:149, A*02:150, A*02:151, A*02:152, A*02:153, A*02:154, A*02:155, A*02:156, A*02:157, A*02:158, A*02:159, A*02:16, A*02:160, A*02:161, A*02:162, A*02:163, A*02:164, A*02:165, A*02:166, A*02:167, A*02:168, A*02:169, A*02:170, A*02:171:01, A*02:171:02, A*02:172, A*02:173, A*02:174, A*02:175, A*02:176, A*02:177, A*02:178, A*02:179, A*02:17:01, A*02:17:02, A*02:18, A*02:180, A*02:181, A*02:182, A*02:183, A*02:184, A*02:185, A*02:186, A*02:187, A*02:188, A*02:189, A*02:19, A*02:190, A*02:191, A*02:192, A*02:193, A*02:194, A*02:195, A*02:196, A*02:197, A*02:198, A*02:199, A*02:200, A*02:201, A*02:202, A*02:203, A*02:204, A*02:205, A*02:206, A*02:207, A*02:208, A*02:209, A*02:20:01, A*02:20:02, A*02:21, A*02:210, A*02:211, A*02:212, A*02:213, A*02:214, A*02:215, A*02:216, A*02:217, A*02:218, A*02:219, A*02:220, A*02:221, A*02:224, A*02:228, A*02:229, A*02:22:01, A*02:22:02, A*02:230, A*02:231, A*02:232, A*02:233, A*02:234, A*02:235, A*02:236, A*02:237, A*02:238, A*02:239, A*02:24, A*02:240, A*02:241, A*02:242, A*02:243, A*02:244, A*02:245, A*02:246, A*02:247, A*02:248, A*02:249, A*02:25, A*02:251, A*02:252, A*02:253, A*02:254, A*02:255, A*02:256, A*02:257, A*02:258, A*02:259, A*02:26, A*02:260, A*02:261, A*02:262, A*02:263, A*02:264, A*02:265, A*02:266, A*02:27, A*02:28, A*02:29, A*02:30, A*02:31, A*02:33, A*02:34, A*02:35:01, A*02:35:02, A*02:35:03, A*02:36, A*02:37, A*02:38, A*02:39, A*02:40, A*02:41, A*02:42, A*02:44, A*02:45, A*02:46, A*02:47, A*02:48, A*02:49, A*02:50, A*02:51, A*02:52, A*02:54, A*02:55, A*02:56:01, A*02:56:02, A*02:57, A*02:58, A*02:59, A*02:60, A*02:61, A*02:62, A*02:63, A*02:64, A*02:65, A*02:66, A*02:67, A*02:68, A*02:69, A*02:70, A*02:71, A*02:72, A*02:73, A*02:74: 01, A*02:74:02, A*02:75, A*02:76, A*02:77, A*02:78, A*02:79, A*02:80, A*02:81, A*02:84, A*02:85, A*02:86, A*02:87, A*02:89, A*02:90, A*02:91, A*02:92, A*02:93, A*02:95, A*02:96, A*02:97:01, A*02:97:02, A*02:99, A*03:01:01:01, A*03:01:01:03, A*03:01:02, A*03:01:03, A*03:01:04, A*03:01:05, A*03:01:06, A*03:01:07, A*03: 01:08, A*03:01:09, A*03:01:10, A*03:01:11, A*03:01:12, A*03:01:13, A*03:01:14, A*03:01:15, A*03:01:16, A*03: 01:17, A*03:01:18, A*03:01:19, A*03:02, A*03:04, A*03: 05, A*03:06, A*03:07, A*03:08, A*03:09, A*03:10, A*03: 12, A*03:13, A*03:14, A*03:15, A*03:16, A*03:17, A*03: 18, A*03:19, A*03:20, A*03:22, A*03:23, A*03:24, A*03: 25, A*03:26, A*03:27, A*03:28, A*03:29, A*03:30, A*03: 31, A*03:32, A*03:33, A*03:34, A*03:35, A*03:37, A*03: 38, A*03:39, A*03:40, A*03:41, A*03:42, A*03:43, A*03: 44, A*03:45, A*03:46, A*03:47, A*03:48, A*03:49, A*03: 50, A*03:51, A*03:52, A*03:53, A*03:54, A*03:55, A*03: 56, A*03:57, A*03:58, A*03:59, A*03:60, A*03:61, A*03: 62, A*03:63, A*03:64, A*03:65, A*03:66, A*03:67, A*03: 70, A*03:71, A*03:72, A*03:73, A*03:74, A*03:75, A*03: 76, A*03:77, A*03:78, A*03:79, A*03:80, A*03:81, A*03: 82, A*11:01:01, A*11:01:02, A*11:01:03, A*11:01:04, A*11:01:05, A*11:01:06, A*11:01:07, A*11:01:08, A*11: 01:09, A*11:01:10, A*11:01:11, A*11:01:12, A*11:01:13, A*11:01:14, A*11:01:15, A*11:01:16, A*11:01:17, A*11: 01:18, A*11:01:19, A*11:01:20, A*11:01:21, A*11:01:22, A*11:02:01, A*11:02:02, A*11:02:03, A*11:03, A*11:04, A*11:05, A*11:06, A*11:07, A*11:08, A*11:09, A*11:10, A*11:11, A*11:12, A*11:13, A*11:14, A*11:15:01, A*11: 15:02, A*11:16, A*11:17, A*11:18, A*11:19, A*11:20, A*11:22, A*11:23, A*11:24:01, A*11:24:02, A*11:25, A*11:26, A*11:27, A*11:29, A*11:30, A*11:31, A*11:32, A*11:33, A*11:34, A*11:35, A*11:36, A*11:37, A*11:38, A*11:39, A*11:40, A*11:41, A*11:42, A*11:43, A*11:44, A*11:45, A*11:46, A*11:47, A*11:48, A*11:49, A*11:51, A*11:53, A*11:54, A*11:55, A*11:56, A*11:57, A*11:58, A*11:59, A*11:60, A*11:61, A*11:62, A*11:63, A*11:64, A*23:01:01, A*23:01:02, A*23:02, A*23:03:01, A*23: 03:02, A*23:04, A*23:05, A*23:06, A*23:09, A*23:10, A*23: 12, A*23:13, A*23:14, A*23:15, A*23:16, A*23:17, A*23: 18, A*23:20, A*23:21, A*23:22, A*23:23, A*23:24, A*23: 25, A*23:26, A*24:02:01:01, A*24:02:02, A*24:02:03, A*24:02:04, A*24:02:05, A*24:02:06, A*24:02:07, A*24: 02:08, A*24:02:09, A*24:02:10, A*24:02:11, A*24:02:12, A*24:02:13, A*24:02:14, A*24:02:15, A*24:02:16, A*24: 02:17, A*24:02:18, A*24:02:19, A*24:02:20, A*24:02:21, A*24:02:22, A*24:02:23, A*24:02:24, A*24:02:25, A*24: 02:26, A*24:02:27, A*24:02:28, A*24:02:29, A*24:02:30, A*24:02:31, A*24:02:32, A*24:02:33, A*24:02:34, A*24: 02:35, A*24:02:36, A*24:03:01, A*24:03:02, A*24:04, A*24:05, A*24:06, A*24:07, A*24:08, A*24:10, A*24:100, A*24:101, A*24:102, A*24:103, A*24:104, A*24:105, A*24:106, A*24:107, A*24:108, A*24:109, A*24:110, A*24:111, A*24:112, A*24:113, A*24:114, A*24:115, A*24:116, A*24:117, A*24:118, A*24:119, A*24:120, A*24:121, A*24:122, A*24:123, A*24:124, A*24:125, A*24:126, A*24:127, A*24:128, A*24:129, A*24:130, A*24:131, A*24:133, A*24:134, A*24:135, A*24:136, A*24:137, A*24:138, A*24:139, A*24:13:01, A*24:13:02, A*24:14, A*24:140, A*24:141, A*24:142, A*24:143, A*24: 144, A*24:15, A*24:17, A*24:18, A*24:19, A*24:20, A*24: 21:01, A*24:21:02, A*24:22, A*24:23, A*24:24, A*24:25, A*24:26, A*24:27, A*24:28, A*24:29, A*24:30, A*24:31, A*24:32, A*24:33, A*24:34, A*24:35, A*24:37, A*24:38, A*24:39, A*24:41, A*24:42, A*24:43, A*24:44, A*24:46, A*24:47, A*24:49, A*24:50, A*24:51, A*24:52, A*24:53, A*24:54, A*24:55, A*24:56, A*24:57, A*24:58, A*24:59, A*24:61, A*24:62, A*24:63, A*24:64, A*24:66, A*24:67, A*24:68, A*24:69, A*24:70, A*24:71, A*24:72, A*24:73, A*24:74, A*24:75, A*24:76, A*24:77, A*24:78, A*24:79, A*24:80, A*24:81, A*24:82, A*24:85, A*24:87, A*24:88, A*24:89, A*24:91, A*24:92, A*24:93, A*24:94, A*24:95, A*24:96, A*24:97, A*24:98, A*24:99, A*25:01:01, A*25: 01:02, A*25:02, A*25:03, A*25:04, A*25:05, A*25:06, A*25:07, A*25:08, A*25:09, A*25:10, A*25:11, A*25:13, A*26:01:01, A*26:01:02, A*26:01:03, A*26:01:04, A*26: 01:05, A*26:01:06, A*26:01:07, A*26:01:08, A*26:01:09, A*26:01:10, A*26:01:11, A*26:01:12, A*26:01:13, A*26: 01:14, A*26:01:15, A*26:01:16, A*26:02, A*26:03:01, A*26:03:02, A*26:04, A*26:05, A*26:06, A*26:07:01, A*26:07:02, A*26:08, A*26:09, A*26:10, A*26:12, A*26: 13, A*26:14, A*26:15, A*26:16, A*26:17, A*26:18, A*26: 19, A*26:20, A*26:21, A*26:22, A*26:23, A*26:24, A*26: 26, A*26:27, A*26:28, A*26:29, A*26:30, A*26:31, A*26: 32, A*26:33, A*26:34, A*26:35, A*26:36, A*26:37, A*26: 38, A*26:39, A*26:40, A*26:41, A*26:42, A*26:43:01, A*26:43:02, A*26:45, A*26:46, A*26:47, A*26:48, A*26: 49, A*26:50, A*29:01:01:01, A*29:01:02, A*29:02:01, A*29:02:02, A*29:02:03, A*29:02:04, A*29:02:05, A*29: 03, A*29:04, A*29:05, A*29:06, A*29:07, A*29:09, A*29: 10, A*29:11, A*29:12, A*29:13, A*29:14, A*29:15, A*29: 16, A*29:17, A*29:18, A*29:19, A*29:20, A*29:21, A*29: 22, A*30:01:01, A*30:01:02, A*30:01:03, A*30:02:01, A*30:02:02, A*30:02:03, A*30:02:04, A*30:02:05, A*30: 03, A*30:04, A*30:06, A*30:07, A*30:08, A*30:09, A*30: 10, A*30:11:01, A*30:11:02, A*30:12, A*30:13, A*30:15, A*30:16, A*30:17, A*30:18, A*30:19, A*30:20, A*30:22, A*30:23, A*30:24, A*30:25, A*30:26, A*30:28, A*30:29, A*30:30, A*30:31, A*30:32, A*30:33, A*30:34, A*30:35, A*30:36, A*30:37, A*30:38, A*30:39, A*30:40, A*30:41, A*31:01:02, A*31:01:03, A*31:01:04, A*31:01:05, A*31: 01:06, A*31:01:07, A*31:01:08, A*31:01:09, A*31:02, A*31:03, A*31:04, A*31:05, A*31:06, A*31:07, A*31:08, A*31:09, A*31:10, A*31:11, A*31:12, A*31:13, A*31:15, A*31:16, A*31:17, A*31:18, A*31:19, A*31:20, A*31:21, A*31:22, A*31:23, A*31:24, A*31:25, A*31:26, A*31:27, A*31:28, A*31:29, A*31:30, A*31:31, A*31:32, A*31:33, A*31:34, A*31:35, A*31:36, A*31:37, A*32:01:01, A*32: 01:02, A*32:01:03, A*32:01:04, A*32:01:05, A*32:02, A*32:03, A*32:04, A*32:05, A*32:06, A*32:07, A*32:08, A*32:09, A*32:10, A*32:12, A*32:13, A*32:14, A*32:15, A*32:16, A*32:17, A*32:18, A*32:20, A*32:21, A*32:22, A*32:23, A*32:24, A*32:25, A*33:01:01, A*33:01:02, A*33:01:03, A*33:03:01, A*33:03:02, A*33:03:03, A*33: 03:04, A*33:03:05, A*33:03:06, A*33:04, A*33:05, A*33: 06, A*33:07, A*33:08, A*33:09, A*33:10, A*33:11, A*33: 12, A*33:13, A*33:14, A*33:15, A*33:16, A*33:17, A*33: 18, A*33:19, A*33:20, A*33:21, A*33:22, A*33:23, A*33: 24, A*33:25, A*33:26, A*33:27, A*33:28, A*33:29, A*33: 30, A*33:31, A*34:01:01, A*34:01:02, A*34:02, A*34:03, A*34:04, A*34:05, A*34:06, A*34:07, A*34:08, A*36:01, A*36:02, A*36:03, A*36:04, A*36:05, A*43:01, A*66:01, A*66:02, A*66:03, A*66:04, A*66:05, A*66:06, A*66:07, A*66:08, A*66:09, A*66:10, A*66:11, A*66:12, A*66:13, A*66:14, A*66:15, A*68:01:01, A*68:01:02, A*68:01:03, A*68:01:04, A*68:01:05, A*68:01:06, A*68:01:07, A*68: 02:01:01, A*68:02:01:02, A*68:02:01:03, A*68:02:02, A*68:02:03, A*68:02:04, A*68:03:01, A*68:03:02, A*68: 04, A*68:05, A*68:06, A*68:07, A*68:08:01, A*68:08:02, A*68:09, A*68:10, A*68:12, A*68:13, A*68:14, A*68:15, A*68:16, A*68:17, A*68:19, A*68:20, A*68:21, A*68:22, A*68:23, A*68:24, A*68:25, A*68:26, A*68:27, A*68:28, A*68:29, A*68:30, A*68:31, A*68:32, A*68:33, A*68:34, A*68:35, A*68:36, A*68:37, A*68:38, A*68:39, A*68:40, A*68:41, A*68:42, A*68:43, A*68:44, A*68:45, A*68:46, A*68:47, A*68:48, A*68:50, A*68:51, A*68:52, A*68:53, A*68:54, A*69:01, A*74:01, A*74:02, A*74:03, A*74:04, A*74:05, A*74:06, A*74:07, A*74:08, A*74:09, A*74:10, A*74:11, A*74:13, A*80:01, A*80:02, B*07:02:01, B*07:02:02, B*07:02:03, B*07:02:04, B*07:02:05, B*07:02:06, B*07:02:07, B*07:02:08, B*07:02:09, B*07:02:10, B*07:02:11, B*07:02:12, B*07:02:13, B*07:02:14, B*07:02:15, B*07:02:16, B*07:02:17, B*07:02:18, B*07:02:19, B*07:02:20, B*07:03, B*07:04, B*07:05:01, B*07:05:02, B*07:05:03, B*07:05:04, B*07:05:05, B*07:06, B*07:07, B*07:08, B*07:09, B*07:10, B*07:100, B*07:101, B*07:102, B*07:103, B*07:104, B*07:105, B*07:106, B*07:107, B*07:108, B*07:109, B*07:11, B*07:110, B*07:112, B*07:113, B*07:114, B*07:115, B*07:12, B*07:13, B*07:14, B*07:15, B*07:16, B*07:17, B*07:18:01, B*07:18:02, B*07:19, B*07:20, B*07:21, B*07:22:01, B*07:22:02, B*07:23, B*07:24, B*07:25, B*07:26, B*07:27, B*07:28, B*07:29, B*07:30, B*07:31, B*07:32, B*07:33, B*07:34, B*07:35, B*07:36, B*07:37, B*07:38, B*07:39, B*07:40, B*07:41, B*07:42, B*07:43, B*07:44, B*07:45, B*07:46, B*07:47, B*07:48, B*07:50, B*07:51, B*07:52, B*07:53, B*07:54, B*07:55, B*07:56, B*07:57, B*07:58, B*07:59, B*07:60, B*07:61, B*07:62, B*07:63, B*07:64, B*07:65, B*07:66, B*07:68:01, B*07:68:02, B*07:69, B*07:70, B*07:71, B*07:72, B*07:73, B*07:74, B*07:75, B*07:76, B*07:77, B*07:78, B*07:79, B*07:80, B*07:81, B*07:82, B*07:83, B*07:84, B*07:85, B*07:86, B*07:87, B*07:88, B*07:89, B*07:90, B*07:91, B*07:92, B*07:93, B*07:94, B*07:95, B*07:96, B*07:97, B*07:98, B*07:99, B*08:01:01, B*08:01:02, B*08:01:03, B*08:01:04, B*08:01:05, B*08:01:06, B*08:01:07, B*08:01:08, B*08:01:09, B*08:01:10, B*08:01:11, B*08:01:12, B*08:02, B*08:03, B*08:04, B*08:05, B*08:07, B*08:09, B*08:10, B*08:11, B*08:12:01, B*08:12:02, B*08:12:03, B*08:13, B*08:14, B*08:15, B*08:16, B*08:17, B*08:18, B*08:20, B*08:21, B*08:22, B*08:23, B*08:24, B*08:25, B*08:26, B*08:27, B*08:28, B*08:29, B*08:31, B*08:32, B*08:33, B*08:34, B*08:35, B*08:36, B*08:37, B*08:38, B*08:39, B*08:40, B*08:41, B*08:42, B*08:43, B*08:44, B*08:45, B*08:46, B*08:47, B*08:48, B*08:49, B*08:50, B*08:51, B*08:52, B*08:53, B*08:54, B*08:55, B*08:56, B*08:57, B*08:58, B*08:59, B*08:60, B*08:61, B*08:62, B*13:01:01, B*13:01:02, B*13:01:03, B*13:01:04, B*13:01:05, B*13:02:01, B*13:02:02, B*13:02:03, B*13:02:04, B*13:02:05, B*13:02:06, B*13:02:07, B*13:02:08, B*13:02:09, B*13:03, B*13:04, B*13:06, B*13:09, B*13:10, B*13:11, B*13:12, B*13:13, B*13:14, B*13:15, B*13:16, B*13:17, B*13:18, B*13:19, B*13:20, B*13:21, B*13:22:01, B*13:22:02, B*13:23, B*13:25, B*13:26, B*13:27, B*13:28, B*13:29, B*13:30, B*13:31, B*13:32, B*13:33, B*13:34, B*13:35, B*13:36, B*13:37, B*13:38, B*13:39, B*14:01, B*14:02:01, B*14:02:02, B*14:02:03, B*14:02:04, B*14:02:05, B*14:03, B*14:04, B*14:05, B*14:06:01, B*14:06:02, B*14:08, B*14:09, B*14:10, B*14:11, B*14:12, B*14:13, B*14:14, B*14:15, B*14:16, B*14:17, B*14:18, B*15:01:01:01, B*15:01:02, B*15:01:03, B*15:01:04, B*15:01:06, B*15:01:07, B*15:01:08, B*15:01:09, B*15:01:10, B*15:01:11, B*15:01:12, B*15:01:13, B*15:01:14, B*15:01:15, B*15:01:16, B*15:01:17, B*15:01:18, B*15:02:01, B*15:02:02, B*15:02:03, B*15:02:04, B*15:03:01, B*15:03:02, B*15:03:03, B*15:04, B*15:05:01, B*15:05:02, B*15:06, B*15:07:01, B*15:07:02, B*15:08, B*15:09, B*15:101, B*15:102, B*15:103, B*15:104, B*15:105, B*15:106, B*15:107, B*15:108, B*15:109, B*15:10:01, B*15:10:02, B*15:110, B*15:112, B*15:113, B*15:114, B*15:115, B*15:116, B*15:117, B*15:118, B*15:119, B*15:11:01, B*15:11:02, B*15:11:03, B*15:11:04, B*15:11:05, B*15:12, B*15:120, B*15:121, B*15:122, B*15:123, B*15:124, B*15:125, B*15:126, B*15:127, B*15:128, B*15:129, B*15:13, B*15:131, B*15:132, B*15:133, B*15:134, B*15:135, B*15:136, B*15:137, B*15:138, B*15:139, B*15:14, B*15:140, B*15:141, B*15:142, B*15:143, B*15:144, B*15:145, B*15:146, B*15:147, B*15:148, B*15:15, B*15:150, B*15:151, B*15:152, B*15:153, B*15:154, B*15:155, B*15:156, B*15:157, B*15:158, B*15:159, B*15:16, B*15:160, B*15:161, B*15:162, B*15:163, B*15:164, B*15:165, B*15:166, B*15:167, B*15:168, B*15:169, B*15:170, B*15:171, B*15:172, B*15:173, B*15:174, B*15:175, B*15:176, B*15:177, B*15:178, B*15:179, B*15:17:01:01, B*15:17:01:02, B*15:17:02, B*15:180, B*15:183, B*15:184, B*15:185, B*15:186, B*15:187, B*15:188, B*15:189, B*15:18:01, B*15:18:02, B*15:18:03, B*15:18:04, B*15:19, B*15:191, B*15:192, B*15:193, B*15:194, B*15:195, B*15:196, B*15:197, B*15:198, B*15:199, B*15:20, B*15:200, B*15:201, B*15:202, B*15:21, B*15:23, B*15:24, B*15:25:01, B*15:25:02, B*15:27:01, B*15:27:02, B*15:27:03, B*15:28, B*15:29, B*15:30, B*15:31, B*15:32, B*15:33, B*15:34, B*15:35, B*15:36, B*15:37, B*15:38:01, B*15:38:02, B*15:39, B*15:40, B*15:42, B*15:43, B*15:44, B*15:45, B*15:46, B*15:47, B*15:48, B*15:49, B*15:50, B*15:51, B*15:52, B*15:53, B*15:54, B*15:55, B*15:56, B*15:57, B*15:58, B*15:60, B*15:61, B*15:62, B*15:63, B*15:64, B*15:65, B*15:66, B*15:67, B*15:68, B*15:69, B*15:70, B*15:71, B*15:72, B*15:73, B*15:74, B*15:75, B*15:76, B*15:77, B*15:78:01, B*15:78:02, B*15:80, B*15:81, B*15:82, B*15:83, B*15:84, B*15:85, B*15:86, B*15:87, B*15:88, B*15:89, B*15:90, B*15:91, B*15:92, B*15:93, B*15:95, B*15:96, B*15:97, B*15:98, B*15:99, B*18:01:01, B*18:01:02, B*18:01:03, B*18:01:04, B*18:01:05, B*18:01:06, B*18:01:07, B*18:01:08, B*18:02, B*18:03, B*18:04, B*18:05, B*18:06, B*18:07:01, B*18:07:02, B*18:08, B*18:09, B*18:10, B*18:11, B*18:12, B*18:13, B*18:14, B*18:15, B*18:18, B*18:19, B*18:20, B*18:21, B*18:22, B*18:24, B*18:25, B*18:26, B*18:27, B*18:28, B*18:29, B*18:30, B*18:31, B*18:32, B*18:33, B*18:34, B*18:35, B*18:36, B*18:37, B*18:38, B*18:39, B*18:40, B*18:41, B*18:42, B*18:43, B*18:44, B*18:45, B*18:46, B*18:47, B*18:48, B*18:49, B*18:50, B*27:01, B*27:02, B*27:03, B*27:04:01, B*27:04:02, B*27:04:03, B*27:05:02, B*27:05:03, B*27:05:04, B*27:05:05, B*27:05:06, B*27:05:07, B*27:05:08, B*27:05:09, B*27:05:10, B*27:05:11, B*27:05:12, B*27:05:13, B*27:05:14, B*27:06, B*27:07, B*27:08, B*27:09, B*27:10, B*27:11, B*27:12, B*27:13, B*27:14, B*27:15, B*27:16, B*27:17, B*27:18, B*27:19, B*27:20, B*27:21, B*27:23, B*27:24, B*27:25, B*27:26, B*27:27, B*27:28, B*27:29, B*27:30, B*27:31, B*27:32, B*27:33, B*27:34, B*27:35, B*27:36, B*27:37, B*27:38, B*27:39, B*27:40, B*27:41, B*27:42, B*27:43, B*27:44, B*27:45, B*27:46, B*27:47, B*27:48, B*27:49, B*27:50, B*27:51, B*27:52, B*27:53, B*27:54, B*27:55, B*27:56, B*27:57, B*27:58, B*27:60, B*27:61, B*27:62, B*27:63, B*27:67, B*27:68, B*27:69, B*35:01:01:01, B*35:01:01:02, B*35:01:02, B*35:01:03, B*35:01:04, B*35:01:05, B*35:01:06, B*35:01:07, B*35:01:08, B*35:01:09, B*35:01:10, B*35:01:11, B*35:01:12, B*35:01:13, B*35:01:14, B*35:01:15, B*35:01:16, B*35:01:17, B*35:01:18, B*35:01:19, B*35:01:20, B*35:01:21, B*35:02:01, B*35:02:02, B*35:02:03, B*35:02:04, B*35:03:01, B*35:03:02, B*35:03:03, B*35:03:04, B*35:04:01, B*35:04:02, B*35:04:03, B*35:05:01, B*35:05:02, B*35:06, B*35:07, B*35:08:01, B*35:08:02, B*35:08:03, B*35:08:04, B*35:09:01, B*35:09:02, B*35:10, B*35:100, B*35:101:01, B*35:101:02, B*35:102, B*35:103, B*35:104, B*35:105, B*35:106, B*35:107, B*35:108:01, B*35:108:02, B*35:109, B*35:110, B*35:111, B*35:112, B*35:113, B*35:114, B*35:115, B*35:116, B*35:117, B*35:118, B*35:119, B*35:11:01, B*35:11:02, B*35:120, B*35:121, B*35:122, B*35:123, B*35:124, B*35:125, B*35:126, B*35:127, B*35:128, B*35:12:01, B*35:12:02, B*35:13, B*35:131, B*35:132, B*35:133, B*35:135, B*35:136, B*35:137, B*35:138, B*35:139, B*35:140, B*35:141, B*35:142, B*35:143, B*35:144, B*35:14:01, B*35:14:02, B*35:15, B*35:16, B*35:17, B*35:18, B*35:19, B*35:20:01, B*35:20:02, B*35:21, B*35:22, B*35:23, B*35:24:01, B*35:24:02, B*35:25, B*35:26, B*35:27, B*35:28, B*35:29, B*35:30, B*35:31, B*35:32, B*35:33, B*35:34, B*35:35, B*35:36, B*35:37, B*35:38, B*35:39, B*35:41, B*35:42:01, B*35:42:02, B*35:43:01, B*35:43:02, B*35:44, B*35:45, B*35:46, B*35:47, B*35:48, B*35:49, B*35:50, B*35:51, B*35:52, B*35:54, B*35:55, B*35:56, B*35:57, B*35:58, B*35:59, B*35:60, B*35:61, B*35:62, B*35:63, B*35:64, B*35:66, B*35:67, B*35:68:01, B*35:68:02, B*35:69, B*35:70, B*35:71, B*35:72, B*35:74, B*35:75, B*35:76, B*35:77, B*35:78, B*35:79, B*35:80, B*35:81, B*35:82, B*35:83, B*35:84, B*35:85, B*35:86, B*35:87, B*35:88, B*35:89, B*35:90, B*35:91, B*35:92, B*35:93, B*35:94, B*35:95, B*35:96, B*35:97, B*35:98, B*35:99, B*37:01:01, B*37:01:02, B*37:01:03, B*37:01:04, B*37:01:05, B*37:01:06, B*37:01:07, B*37:02, B*37:04:01, B*37:04:02, B*37:05, B*37:06, B*37:07, B*37:08, B*37:09, B*37:10, B*37:11, B*37:12, B*37:13, B*37:14, B*37:15, B*37:17, B*37:18, B*37:19, B*37:20, B*37:21, B*37:22, B*37:23, B*38:01:01, B*38:01:02, B*38:01:03, B*38:01:04, B*38:02:01, B*38:02:02, B*38:03, B*38:04, B*38:05, B*38:06, B*38:07, B*38:08, B*38:09, B*38:10, B*38:11, B*38:12, B*38:13, B*38:14, B*38:15, B*38:16, B*38:17, B*38:18, B*38:19, B*38:20, B*38:21, B*38:22, B*38:23, B*39:01:01:01, B*39:01:03, B*39:01:04, B*39:01:05, B*39:01:06, B*39:01:07, B*39:01:08, B*39:01:09, B*39:01:10, B*39:01:11, B*39:02:01, B*39:02:02, B*39:03, B*39:04, B*39:05:01, B*39:05:02, B*39:06:01, B*39:06:02, B*39:07, B*39:08, B*39:09, B*39:10, B*39:11, B*39:12, B*39:13:01, B*39:13:02, B*39:14, B*39:15, B*39:16, B*39:17, B*39:18, B*39:19:01, B*39:19:02, B*39:20, B*39:22, B*39:23, B*39:24, B*39:26, B*39:27, B*39:28, B*39:29, B*39:30, B*39:31, B*39:32, B*39:33, B*39:34, B*39:35, B*39:36, B*39:37, B*39:39, B*39:41, B*39:42, B*39:43, B*39:44, B*39:45, B*39:46, B*39:47, B*39:48, B*39:49, B*39:50, B*39:51, B*39:52, B*39:53, B*39:54, B*39:55, B*39:56, B*39:57, B*39:58, B*39:59, B*39:60, B*40:01:01, B*40:01:02, B*40:01:03, B*40:01:04, B*40:01:05, B*40:01:06, B*40:01:07, B*40:01:08, B*40:01:09, B*40:01:10, B*40:01:11, B*40:01:12, B*40:02:01, B*40:02:02, B*40:02:03, B*40:02:04, B*40:02:05, B*40:02:06, B*40:02:07, B*40:02:08, B*40:02:09, B*40:02:10, B*40:02:11, B*40:03, B*40:04, B*40:05, B*40:06:01:01, B*40:06:01:02, B*40:06:02, B*40:06:03, B*40:07, B*40:08, B*40:09, B*40:100, B*40:101, B*40:102, B*40:103, B*40:104, B*40:105, B*40:106, B*40:107, B*40:108, B*40:109, B*40:10:01, B*40:10:02, B*40:110, B*40:111, B*40:112, B*40:113, B*40:114, B*40:115, B*40:116, B*40:117, B*40:119, B*40:11:01, B*40:11:02, B*40:12, B*40:120, B*40:121, B*40:122, B*40:123, B*40:124:01, B*40:124:02, B*40:125, B*40:126, B*40:127, B*40:128, B*40:129, B*40:13, B*40:130, B*40:131, B*40:132, B*40:134, B*40:135, B*40:136, B*40:137, B*40:138, B*40:139, B*40:140, B*40:141, B*40:143, B*40:145, B*40:146, B*40:147, B*40:14:01, B*40:14:02, B*40:14:03, B*40:15, B*40:16, B*40:18, B*40:19, B*40:20, B*40:21, B*40:23, B*40:24, B*40:25, B*40:26, B*40:27, B*40:28, B*40:29, B*40:30, B*40:31, B*40:32, B*40:33, B*40:34, B*40:35, B*40:36, B*40:37, B*40:38, B*40:39, B*40:40, B*40:42, B*40:43, B*40:44, B*40:45, B*40:46, B*40:47, B*40:48, B*40:49, B*40:50, B*40:51, B*40:52, B*40:53, B*40:54, B*40:55, B*40:56, B*40:57, B*40:58, B*40:59, B*40:60, B*40:61, B*40:62, B*40:63, B*40:64, B*40:65, B*40:66, B*40:67, B*40:68, B*40:69, B*40:70, B*40:71, B*40:72:01, B*40:72:02, B*40:73, B*40:74, B*40:75, B*40:76, B*40:77, B*40:78, B*40:79, B*40:80, B*40:81, B*40:82, B*40:83, B*40:84, B*40:85, B*40:86, B*40:87, B*40:88, B*40:89, B*40:90, B*40:91, B*40:92, B*40:93, B*40:94, B*40:95, B*40:96, B*40:97, B*40:98, B*40:99, B*41:01, B*41:02:01, B*41:02:02, B*41:03:01, B*41:03:02, B*41:04, B*41:05, B*41:06, B*41:07, B*41:08, B*41:09, B*41:10, B*41:11, B*41:12, B*42:01:01, B*42:01:02, B*42:02, B*42:04, B*42:05:01, B*42:05:02, B*42:06, B*42:07, B*42:08, B*42:09, B*42:10, B*42:11, B*42:12, B*42:13, B*42:14, B*44:02:01:01, B*44:02:02, B*44:02:03, B*44:02:04, B*44:02:05, B*44:02:06, B*44:02:07, B*44:02:08, B*44:02:09, B*44:02:10, B*44:02:11, B*44:02:12, B*44:02:13, B*44:03:01, B*44:03:02, B*44:03:03, B*44:03:04, B*44:03:05, B*44:03:06, B*44:03:07, B*44:03:08, B*44:03:09, B*44:03:10, B*44:03:11, B*44:04, B*44:05:01, B*44:05:02, B*44:06, B*44:07, B*44:08, B*44:09, B*44:10, B*44:100, B*44:101, B*44:102, B*44:103, B*44:104, B*44:105, B*44:106, B*44:107, B*44:109, B*44:11, B*44:110, B*44:12, B*44:13, B*44:14, B*44:15, B*44:16, B*44:17, B*44:18, B*44:20, B*44:21, B*44:22, B*44:24, B*44:25, B*44:26, B*44:27, B*44:28:01, B*44:28:02, B*44:29, B*44:30, B*44:31, B*44:32, B*44:33, B*44:34, B*44:35, B*44:36, B*44:37, B*44:38, B*44:39, B*44:40, B*44:41, B*44:42, B*44:43, B*44:44, B*44:45, B*44:46, B*44:47, B*44:48, B*44:49, B*44:50, B*44:51, B*44:53, B*44:54, B*44:55, B*44:57, B*44:59, B*44:60, B*44:62, B*44:63, B*44:64:01, B*44:64:02, B*44:65, B*44:66, B*44:67, B*44:68, B*44:69, B*44:70, B*44:71, B*44:72, B*44:73, B*44:74, B*44:75, B*44:76, B*44:77, B*44:78, B*44:79, B*44:80, B*44:81, B*44:82, B*44:83, B*44:84, B*44:85, B*44:86, B*44:87, B*44:88, B*44:89, B*44:90, B*44:91, B*44:92, B*44:93, B*44:94, B*44:95, B*44:96, B*44:97, B*44:98, B*44:99, B*45:01, B*45:02, B*45:03, B*45:04, B*45:05, B*45:06, B*45:07, B*45:08, B*45:09, B*45:10, B*45:11, B*45:12, B*46:01:01, B*46:01:02, B*46:01:03, B*46:01:04, B*46:02, B*46:03, B*46:04, B*46:05, B*46:06, B*46:08, B*46:09, B*46:10, B*46:11, B*46:12, B*46:13:01, B*46:13:02, B*46:13:03, B*46:14, B*46:16, B*46:17, B*46:18, B*46:19, B*46:20, B*46:21, B*46:22, B*46:23, B*46:24, B*47:01:01:01, B*47:01:01:02, B*47:02, B*47:03, B*47:04, B*47:05, B*47:06, B*47:07, B*48:01:01, B*48:01:02, B*48:01:03, B*48:02:01, B*48:02:02, B*48:03:01, B*48:03:02, B*48:04, B*48:05, B*48:06, B*48:07, B*48:08, B*48:09, B*48:10, B*48:11, B*48:12, B*48:13, B*48:14, B*48:15, B*48:16, B*48:17, B*48:18, B*48:19, B*48:20, B*48:21, B*48:22, B*48:23, B*49:01:01, B*49:01:02, B*49:02, B*49:03, B*49:04, B*49:05, B*49:06, B*49:07, B*49:08, B*49:09, B*49:10, B*50:01:01, B*50:01:02, B*50:02, B*50:04, B*50:05, B*50:06, B*50:07, B*50:08, B*50:09, B*51:01:01, B*51:01:02, B*51:01:03, B*51:01:04, B*51:01:05, B*51:01:06, B*51:01:07, B*51:01:08, B*51:01:09, B*51:01:10, B*51:01:11, B*51:01:12, B*51:01:13, B*51:01:14, B*51:01:15, B*51:01:16, B*51:01:17, B*51:02:01, B*51:02:02, B*51:02:03, B*51:02:04, B*51:03, B*51:04, B*51:05, B*51:06, B*51:07:01, B*51:07:02, B*51:08, B*51:09:01, B*51:09:02, B*51:10, B*51:12, B*51:13:01, B*51:13:02, B*51:14, B*51:15, B*51:16, B*51:17, B*51:18, B*51:19, B*51:20, B*51:21, B*51:22, B*51:23, B*51:24:01, B*51:24:02, B*51:24:03, B*51:26, B*51:28, B*51:29, B*51:30, B*51:31, B*51:32, B*51:33, B*51:34, B*51:35, B*51:36, B*51:37, B*51:38, B*51:39, B*51:40, B*51:42, B*51:43, B*51:45, B*51:46, B*51:48, B*51:49, B*51:50, B*51:51, B*51:52, B*51:53, B*51:54, B*51:55, B*51:56, B*51:57, B*51:58, B*51:59, B*51:60, B*51:61, B*51:62, B*51:63, B*51:64, B*51:65, B*51:66, B*51:67, B*51:68, B*51:69, B*51:70, B*51:71, B*51:72, B*51:73, B*51:74, B*51:75, B*51:76, B*51:77, B*51:78, B*51:79, B*51:80, B*51:81, B*51:82, B*51:83, B*51:84, B*51:85, B*51:86, B*51:87, B*51:88, B*51:89, B*51:90, B*51:91, B*51:92, B*51:93, B*51:94, B*51:95, B*51:96, B*52:01:01, B*52:01:02, B*52:01:03, B*52:01:04, B*52:01:05, B*52:02, B*52:03, B*52:04, B*52:05, B*52:06:01, B*52:06:02, B*52:07, B*52:08, B*52:09, B*52:10, B*52:11, B*52:12, B*52:13, B*52:14, B*52:15, B*52:16, B*52:17, B*52:18, B*52:19, B*52:20, B*52:21, B*53:01:01, B*53:01:02, B*53:01:03, B*53:01:04, B*53:01:05, B*53:02, B*53:03, B*53:04, B*53:05, B*53:06, B*53:07, B*53:08:01, B*53:08:02, B*53:09, B*53:10, B*53:11, B*53:12, B*53:13, B*53:14, B*53:15, B*53:16, B*53:17, B*53:18, B*53:19, B*53:20, B*53:21, B*53:22, B*53:23, B*54:01, B*54:02, B*54:03, B*54:04, B*54:06, B*54:07, B*54:09, B*54:10, B*54:11, B*54:12, B*54:13, B*54:14, B*54:15, B*54:16, B*54:17, B*54:18, B*54:19, B*54:20, B*54:21, B*54:22, B*54:23, B*55:01:01, B*55:01:02, B*55:01:03, B*55:01:04, B*55:01:05, B*55:01:06, B*55:02:01, B*55:02:02, B*55:02:03, B*55:02:04, B*55:02:05, B*55:02:06, B*55:03, B*55:04, B*55:05, B*55:07, B*55:08, B*55:09, B*55:10, B*55:11, B*55:12, B*55:13, B*55:14, B*55:15, B*55:16, B*55:17, B*55:18, B*55:19, B*55:20, B*55:21, B*55:22, B*55:23, B*55:24, B*55:25, B*55:26, B*55:27, B*55:28, B*55:29, B*55:30, B*55:31, B*55:32, B*55:33, B*55:34, B*55:35, B*55:36, B*55:37, B*55:38, B*55:39, B*55:40, B*55:41, B*55:42, B*55:43, B*56:01:01, B*56:01:02, B*56:01:03, B*56:01:04, B*56:02, B*56:03, B*56:04, B*56:05:01, B*56:05:02, B*56:06, B*56:07, B*56:08, B*56:09, B*56:10, B*56:11, B*56:12, B*56:13, B*56:14, B*56:15, B*56:16, B*56:17, B*56:18, B*56:20, B*56:21, B*56:22, B*56:23, B*56:24, B*56:25, B*56:26, B*56:27, B*56:29, B*57:01:01, B*57:01:02, B*57:01:03, B*57:01:04, B*57:01:05, B*57:01:06, B*57:01:07, B*57:01:08, B*57:02:01, B*57:02:02, B*57:03:01, B*57:03:02, B*57:04, B*57:05, B*57:06, B*57:07, B*57:08, B*57:09, B*57:10, B*57:11, B*57:12, B*57:13, B*57:14, B*57:15, B*57:16, B*57:17, B*57:18, B*57:19, B*57:20, B*57:21, B*57:22, B*57:23, B*57:24, B*57:25, B*57:26, B*57:27, B*57:29, B*57:30, B*57:31, B*57:32, B*58:01:01, B*58:01:02, B*58:01:03, B*58:01:04, B*58:01:05, B*58:01:06, B*58:01:07, B*58:02, B*58:04, B*58:05, B*58:06, B*58:07, B*58:08, B*58:09, B*58:11, B*58:12, B*58:13, B*58:14, B*58:15, B*58:16, B*58:18, B*58:19, B*58:20, B*58:21, B*58:22, B*58:23, B*58:24, B*58:25, B*58:26, B*58:27, B*58:28, B*58:29, B*58:30, B*59:01, B*59:02, B*59:03, B*59:04, B*59:05, B*67:01:01, B*67:01:02, B*67:02, B*73:01, B*73:02, B*78:01, B*78:02:01, B*78:02:02, B*78:03, B*78:04, B*78:05, B*78:06, B*78:07, B*81:01, B*81:02, B*81:03, B*81:05, B*82:01, B*82:02, B*82:03, B*83:01, C*01:02:01, C*01:02:02, C*01:02:03, C*01:02:04, C*01:02:05, C*01:02:06, C*01:02:07, C*01:02:08, C*01:02:09, C*01:02:10, C*01:02:11, C*01:03, C*01:04, C*01:05, C*01:06, C*01:07, C*01:08, C*01:09, C*01:10, C*01:11, C*01:12, C*01:13, C*01:14, C*01:15, C*01:16, C*01:17, C*01:18, C*01:19, C*01:20, C*01:21, C*01:22, C*01:23, C*01:24, C*01:25, C*01:26, C*01:27, C*01:28, C*01:29, C*01:30, C*01:31, C*01:32, C*01:33, C*01:34, C*01:35, C*01:36, C*01:38, C*01:39, C*01:40, C*02:02:01, C*02:02:02, C*02:02:03, C*02:02:05, C*02:02:06, C*02:02:07, C*02:02:08, C*02:02:09, C*02:02:10, C*02:02:11, C*02:02:12, C*02:02:13, C*02:03, C*02:04, C*02:05, C*02:06, C*02:07, C*02:08, C*02:09, C*02:10, C*02:11, C*02:12, C*02:13, C*02:14, C*02:15, C*02:16:01, C*02:16:02, C*02:17, C*02:18, C*02:19, C*02:20, C*02:21, C*02:22, C*02:23, C*02:24, C*02:26:01, C*02:26:02, C*02:27:01, C*02:27:02, C*02:28, C*02:29, C*02:30, C*02:31, C*02:32, C*02:33, C*02:34, C*02:35, C*02:36, C*02:37, C*02:39, C*02:40, C*03:02:01, C*03:02:02, C*03:02:03, C*03:02:04, C*03:02:05, C*03:02:06, C*03:03:01, C*03:03:02, C*03:03:03, C*03:03:04, C*03:03:05, C*03:03:06, C*03:03:07, C*03:03:08, C*03:03:09, C*03:03:10, C*03:03:11, C*03:03:12, C*03:04:01:01, C*03:04:01:02, C*03:04:02, C*03:04:03, C*03:04:04, C*03:04:05, C*03:04:06, C*03:04:07, C*03:04:08, C*03:04:09, C*03:04:10, C*03:04:11, C*03:04:12, C*03:04:13, C*03:04:14, C*03:04:15, C*03:04:16, C*03:04:17, C*03:04:18, C*03:04:19, C*03:05, C*03:06, C*03:07, C*03:08, C*03:09, C*03:10, C*03:11:01, C*03:11:02, C*03:12, C*03:13, C*03:14, C*03:15, C*03:16, C*03:17, C*03:18, C*03:19, C*03:21, C*03:23, C*03:24, C*03:25, C*03:26, C*03:27, C*03:28, C*03:29, C*03:30, C*03:31, C*03:32, C*03:33, C*03:34, C*03:35, C*03:36, C*03:37, C*03:38:01, C*03:38:02, C*03:39, C*03:40, C*03:41, C*03:42, C*03:43:01, C*03:43:02, C*03:44, C*03:45, C*03:46, C*03:47, C*03:48, C*03:49, C*03:50, C*03:51, C*03:52, C*03:53, C*03:54, C*03:55, C*03:56, C*03:57, C*03:58, C*03:59, C*03:60, C*03:61, C*03:62, C*03:63, C*03:64, C*03:65, C*03:66, C*03:67, C*03:68, C*03:69, C*03:70, C*03:71, C*03:72, C*03:73, C*03:74, C*03:75, C*03:76, C*03:77, C*03:78, C*03:79, C*03:80, C*03:81, C*03:82, C*03:83, C*03:84, C*03:85, C*03:86, C*03:87, C*03:88, C*03:89, C*03:90, C*03:91, C*03:92, C*03:93, C*03:94, C*04:01:01:01, C*04:01:01:02, C*04:01:01:03, C*04:01:02, C*04:01:03, C*04:01:04, C*04:01:05, C*04:01:06, C*04:01:07, C*04:01:08, C*04:01:09, C*04:01:10, C*04:01:11, C*04:01:12, C*04:01:13, C*04:01:14, C*04:01:15, C*04:01:16, C*04:01:17, C*04:01:18, C*04:01:19, C*04:01:20, C*04:01:21, C*04:03, C*04:04:01, C*04:04:02, C*04:05, C*04:06, C*04:07, C*04:08, C*04:10, C*04:11, C*04:12, C*04:13, C*04:14, C*04:15:01, C*04:15:02, C*04:16, C*04:17, C*04:18, C*04:19, C*04:20, C*04:23, C*04:24, C*04:25, C*04:26, C*04:27, C*04:28, C*04:29, C*04:30, C*04:31, C*04:32, C*04:33, C*04:34, C*04:35, C*04:36, C*04:37, C*04:38, C*04:39, C*04:40, C*04:41, C*04:42, C*04:43, C*04:44, C*04:45, C*04:46, C*04:47, C*04:48, C*04:49, C*04:50, C*04:51, C*04:52, C*04:53, C*04:54, C*04:55, C*04:56, C*04:57, C*04:58, C*04:60, C*04:61, C*04:62, C*04:63, C*04:64, C*04:65, C*04:66, C*04:67, C*04:68, C*04:69, C*04:70, C*05:01:01:01, C*05:01:01:02, C*05:01:02, C*05:01:03, C*05:01:04, C*05:01:05, C*05:01:06, C*05:01:07, C*05:01:08, C*05:01:09, C*05:01:10, C*05:01:11, C*05:01:12, C*05:01:13, C*05:03, C*05:04, C*05:05, C*05:06, C*05:08, C*05:09, C*05:10, C*05:11, C*05:12, C*05:13, C*05:14, C*05:15, C*05:16, C*05:17, C*05:18, C*05:19, C*05:20, C*05:21, C*05:22, C*05:23, C*05:24, C*05:25, C*05:26, C*05:27, C*05:28, C*05:29, C*05:30, C*05:31, C*05:32, C*05:33, C*05:34, C*05:35, C*05:36, C*05:37, C*05:38, C*05:39, C*05:40, C*05:41, C*05:42, C*05:43, C*05:44, C*05:45, C*06:02:01:01, C*06:02:01:02, C*06:02:03, C*06:02:04, C*06:02:05, C*06:02:06, C*06:02:07, C*06:02:08, C*06:03, C*06:04, C*06:05, C*06:06, C*06:07, C*06:08, C*06:09, C*06:10, C*06:11, C*06:12, C*06:13, C*06:14, C*06:15, C*06:17, C*06:18, C*06:19, C*06:20, C*06:21, C*06:22, C*06:23, C*06:24, C*06:25, C*06:26, C*06:27, C*06:28, C*06:29, C*06:30, C*06:31, C*06:32, C*06:33, C*06:34, C*06:35, C*06:36, C*06:37, C*06:38, C*06:39, C*06:40, C*06:41, C*06:42, C*06:43, C*06:44, C*06:45, C*07:01:01, C*07:01:02, C*07:01:03, C*07:01:04, C*07:01:05, C*07:01:06, C*07:01:07, C*07:01:08, C*07:01:09, C*07:01:10, C*07:01:11, C*07:01:12, C*07:02:01:01, C*07:02:01:02, C*07:02:01:03, C*07:02:02, C*07:02:03, C*07:02:04, C*07:02:05, C*07:02:06, C*07:02:07, C*07:02:08, C*07:02:09, C*07:02:10, C*07:02:11, C*07:02:12, C*07:02:13, C*07:02:14, C*07:02:15, C*07:02:16, C*07:03, C*07:04:01, C*07:04:02, C*07:04:03, C*07:04:04, C*07:05, C*07:06, C*07:07, C*07:08, C*07:09, C*07:10, C*07:100, C*07:101, C*07:102, C*07:103, C*07:105, C*07:106, C*07:107, C*07:108, C*07:109, C*07:11, C*07:110, C*07:111, C*07:112, C*07:113, C*07:114, C*07:115, C*07:116, C*07:117, C*07:118, C*07:119, C*07:12, C*07:120, C*07:122, C*07:123, C*07:124, C*07:125, C*07:126, C*07:127, C*07:128, C*07:129, C*07:13, C*07:130, C*07:131, C*07:132, C*07:133, C*07:134, C*07:135, C*07:136, C*07:137, C*07:138, C*07:139, C*07:14, C*07:140, C*07:141, C*07:142, C*07:143, C*07:144, C*07:145, C*07:146, C*07:147, C*07:148, C*07:149, C*07:15, C*07:16, C*07:17, C*07:18, C*07:19, C*07:20, C*07:21, C*07:22, C*07:23, C*07:24, C*07:25, C*07:26, C*07:27:01, C*07:27:02, C*07:28, C*07:29, C*07:30, C*07:31, C*07:35, C*07:36, C*07:37, C*07:38, C*07:39, C*07:40, C*07:41, C*07:42, C*07:43, C*07:44, C*07:45, C*07:46, C*07:47, C*07:48, C*07:49, C*07:50, C*07:51, C*07:52, C*07:53, C*07:54, C*07:56:01, C*07:56:02, C*07:57, C*07:58, C*07:59, C*07:60, C*07:62, C*07:63, C*07:64, C*07:65, C*07:66, C*07:67, C*07:68, C*07:69, C*07:70, C*07:71, C*07:72, C*07:73, C*07:74, C*07:75, C*07:76, C*07:77, C*07:78, C*07:79, C*07:80, C*07:81, C*07:82, C*07:83, C*07:84, C*07:85, C*07:86, C*07:87, C*07:88, C*07:89, C*07:90, C*07:91, C*07:92, C*07:93, C*07:94, C*07:95, C*07:96, C*07:97, C*07:99, C*08:01:01, C*08:01:02, C*08:02:01, C*08:02:02, C*08:02:03, C*08:02:04, C*08:03:01, C*08:03:02, C*08:04, C*08:05, C*08:06, C*08:07, C*08:08, C*08:09, C*08:10, C*08:11, C*08:12, C*08:13, C*08:14, C*08:15, C*08:16, C*08:17, C*08:18, C*08:19, C*08:20, C*08:21, C*08:22, C*08:23, C*08:24, C*08:25, C*08:27, C*08:28, C*08:29, C*08:30, C*08:31, C*08:32, C*08:33, C*08:34, C*08:35, C*12:02:01, C*12:02:02, C*12:02:03, C*12:02:04, C*12:02:05, C*12:02:06, C*12:03:01:01, C*12:03:01:02, C*12:03:02, C*12:03:03, C*12:03:04, C*12:03:05, C*12:03:06, C*12:03:07, C*12:03:08, C*12:03:09, C*12:03:10, C*12:03:11, C*12:03:12, C*12:04:01, C*12:04:02, C*12:05, C*12:06, C*12:07, C*12:08, C*12:09, C*12:10:01, C*12:10:02, C*12:11, C*12:12, C*12:13, C*12:14:01, C*12:14:02, C*12:15, C*12:16, C*12:17, C*12:18, C*12:19, C*12:20, C*12:21, C*12:22, C*12:23, C*12:24, C*12:25, C*12:26, C*12:27, C*12:28, C*12:29, C*12:30, C*12:31, C*12:32, C*12:33, C*12:34, C*12:35, C*12:36, C*12:37, C*12:38, C*12:40, C*12:41, C*12:43, C*12:44, C*14:02:01, C*14:02:02, C*14:02:03, C*14:02:04, C*14:02:05, C*14:03, C*14:04, C*14:05, C*14:06, C*14:08, C*14:09, C*14:10, C*14:11, C*14:12, C*14:13, C*14:14, C*14:15, C*14:16, C*14:17, C*14:18, C*14:19, C*14:20, C*15:02:01, C*15:02:02, C*15:02:03, C*15:02:04, C*15:02:05, C*15:02:06, C*15:03, C*15:04, C*15:05:01, C*15:05:02, C*15:05:03, C*15:05:04, C*15:05:05, C*15:06:01, C*15:06:02, C*15:07, C*15:08, C*15:09, C*15:10:01, C*15:10:02, C*15:11, C*15:12, C*15:13, C*15:15, C*15:16, C*15:17, C*15:18, C*15:19, C*15:20, C*15:21, C*15:22, C*15:23, C*15:24, C*15:25, C*15:26, C*15:27, C*15:28, C*15:29, C*15:30, C*15:31, C*15:33, C*15:34, C*15:35, C*16:01:01, C*16:01:02, C*16:01:03, C*16:01:04, C*16:02:01, C*16:02:02, C*16:02:03, C*16:02:04, C*16:04:01, C*16:06, C*16:07, C*16:08, C*16:09, C*16:10, C*16:11, C*16:12, C*16:13, C*16:14, C*16:15, C*16:17, C*16:18, C*16:19, C*16:20, C*16:21, C*16:22, C*16:23, C*16:24, C*16:25, C*16:26, C*17:01:01:01, C*17:01:01:02, C*17:01:02, C*17:01:03, C*17:01:04, C*17:02, C*17:03, C*17:04, C*17:05, C*17:06, C*17:07, C*18:01, C*18:02, C*18:03, E*01:01:01:01, E*01:01:01:02, E*01:01:01:03, E*01:03:01:01, E*01:03:01:02, E*01:03:02, E*01:03:03, E*01:03:04, E*01:04, F*01:01:01:01, F*01:01:01:02, F*01:01:01:03, F*01:01:01:04, F*01:01:01:05, F*01:01:01:06, F*01:01:01:07, F*01:01:01:08, F*01:01:02:01, F*01:01:02:02, F*01:01:02:03, F*01:01:02:04, F*01:01:02:05, F*01:01:03:01, F*01:01:03:02, F*01:01:03:03, F*01:01:03:04, F*01:02, F*01:03:01:01, F*01:03:01:02, F*01:04, G*01:01:01:01, G*01:01:01:02, G*01:01:01:03, G*01:01:01:04, G*01:01:01:05, G*01:01:01:06, G*01:01:02:01, G*01:01:02:02, G*01:01:03:01, G*01:01:03:02, G*01:01:04, G*01:01:05, G*01:01:06, G*01:01:07, G*01:01:08, G*01:01:09, G*01:01:11, G*01:01:12, G*01:01:13, G*01:01:14, G*01:01:15, G*01:01:16, G*01:01:17, G*01:01:18, G*01:01:19, G*01:01:20, G*01:02, G*01:03, G*01:04:01, G*01:04:02, G*01:04:03, G*01:04:04, G*01:04:05, G*01:06, G*01:07, G*01:08, G*01:09, G*01:10, G*01:11, G*01:12, G*01:14, G*01:15, G*01:16, G*01:17, DRA*01:01, DRA*01:02:01, DRA*01:02:02, DRB1*01:01:01, DRB1*01:01:02, DRB1*01:01:03, DRB1*01:01:04, DRB1*01:01:05, DRB1*01:01:06, DRB1*01:01:07, DRB1*01:01:08, DRB1*01:01:09, DRB1*01:01:10, DRB1*01:01:11, DRB1*01:01:12, DRB1*01:01:13, DRB1*01:01:14, DRB1*01:01:15, DRB1*01:01:16, DRB1*01:01:17, DRB1*01:01:18, DRB1*01:02:01, DRB1*01:02:02, DRB1*01:02:03, DRB1*01:02:04, DRB1*01:02:05, DRB1*01:03, DRB1*01:04, DRB1*01:05, DRB1*01:06, DRB1*01:07, DRB1*01:08, DRB1*01:09, DRB1*01:10, DRB1*01:11, DRB1*01:12, DRB1*01:13, DRB1*01:14, DRB1*01:15, DRB1*01:16, DRB1*01:17, DRB1*01:18, DRB1*01:19, DRB1*01:20, DRB1*01:21, DRB1*01:22, DRB1*01:23, DRB1*01:24, DRB1*01:25, DRB1*01:26, DRB1*01:27, DRB1*01:28, DRB1*01:29, DRB1*01:30, DRB1*01:31, DRB1*01:32, DRB1*03:01:01, DRB1*03:01:01:02, DRB1*03:01:02, DRB1*03:01:03, DRB1*03:01:04, DRB1*03:01:05, DRB1*03:01:06, DRB1*03:01:07, DRB1*03:01:08, DRB1*03:01:09, DRB1*03:02:01, DRB1*03:02:02, DRB1*03:03, DRB1*03:04, DRB1*03:05:01, DRB1*03:05:02, DRB1*03:05:03, DRB1*03:06, DRB1*03:07, DRB1*03:08, DRB1*03:09, DRB1*03:10, DRB1*03:11:01, DRB1*03:11:02, DRB1*03:12, DRB1*03:13:01, DRB1*03:13:02, DRB1*03:14, DRB1*03:15, DRB1*03:16, DRB1*03:17, DRB1*03:18, DRB1*03:19, DRB1*03:20, DRB1*03:21, DRB1*03:22, DRB1*03:23, DRB1*03:24, DRB1*03:25, DRB1*03:26, DRB1*03:27, DRB1*03:28, DRB1*03:29, DRB1*03:30, DRB1*03:31, DRB1*03:32, DRB1*03:33, DRB1*03:34, DRB1*03:35, DRB1*03:36, DRB1*03:37, DRB1*03:38, DRB1*03:39, DRB1*03:40, DRB1*03:41, DRB1*03:42, DRB1*03:43, DRB1*03:44, DRB1*03:45, DRB1*03:46, DRB1*03:47, DRB1*03:48, DRB1*03:49, DRB1*03:50, DRB1*03:51, DRB1*03:52, DRB1*03:53, DRB1*03:54, DRB1*03:55, DRB1*04:01:01, DRB1*04:01:02, DRB1*04:01:03, DRB1*04:01:04, DRB1*04:01:05, DRB1*04:01:06, DRB1*04:02, DRB1*04:03:01, DRB1*04:03:02, DRB1*04:03:03, DRB1*04:03:04, DRB1*04:03:05, DRB1*04:04:01, DRB1*04:04:02, DRB1*04:04:03, DRB1*04:04:04, DRB1*04:05, DRB1*04:05:01, DRB1*04:05:02, DRB1*04:05:03, DRB1*04:05:04, DRB1*04:05:05, DRB1*04:05:06, DRB1*04:05:07, DRB1*04:05:08, DRB1*04:05:09, DRB1*04:05:10, DRB1*04:06:01, DRB1*04:06:02, DRB1*04:06:03, DRB1*04:07:01, DRB1*04:07:02, DRB1*04:07:03, DRB1*04:07:04, DRB1*04:08:01, DRB1*04:08:02, DRB1*04:08:09, DRB1*04:10, DRB1*04:11, DRB1*04:12, DRB1*04:13, DRB1*04:14, DRB1*04:15, DRB1*04:16, DRB1*04:17:01, DRB1*04:17:02, DRB1*04:18, DRB1*04:19, DRB1*04:20, DRB1*04:21, DRB1*04:22, DRB1*04:23, DRB1*04:24, DRB1*04:25, DRB1*04:26, DRB1*04:27, DRB1*04:28, DRB1*04:29, DRB1*04:30, DRB1*04:31, DRB1*04:32, DRB1*04:33, DRB1*04:34, DRB1*04:35, DRB1*04:36, DRB1*04:37, DRB1*04:38, DRB1*04:39, DRB1*04:40, DRB1*04:41, DRB1*04:42, DRB1*04:43, DRB1*04:44, DRB1*04:45, DRB1*04:46, DRB1*04:47, DRB1*04:48, DRB1*04:49, DRB1*04:50, DRB1*04:51, DRB1*04:52, DRB1*04:53, DRB1*04:54, DRB1*04:55, DRB1*04:56, DRB1*04:57, DRB1*04:58, DRB1*04:59, DRB1*04:60, DRB1*04:61, DRB1*04:62, DRB1*04:63, DRB1*04:64, DRB1*04:65, DRB1*04:66, DRB1*04:67, DRB1*04:68, DRB1*04:69, DRB1*04:70, DRB1*04:71, DRB1*04:72:01, DRB1*04:72:02, DRB1*04:73, DRB1*04:74, DRB1*04:75, DRB1*04:76, DRB1*04:77, DRB1*04:78, DRB1*04:79, DRB1*04:80, DRB1*04:82, DRB1*04:83, DRB1*04:84, DRB1*04:85, DRB1*04:86, DRB1*04:87, DRB1*04:88, DRB1*04:89, DRB1*04:91, DRB1*07:01:01:01, DRB1*07:01:01:02, DRB1*07:01:02, DRB1*07:01:03, DRB1*07:03, DRB1*07:04, DRB1*07:05, DRB1*07:06, DRB1*07:07, DRB1*07:08, DRB1*07:09, DRB1*07:11, DRB1*07:12, DRB1*07:13, DRB1*07:14, DRB1*07:15, DRB1*07:16, DRB1*07:17, DRB1*07:19, DRB1*08:01:01, DRB1*08:01:02, DRB1*08:01:03, DRB1*08:01:04, DRB1*08:01:05, DRB1*08:02:01, DRB1*08:02:02, DRB1*08:02:03, DRB1*08:03:02, DRB1*08:04:01, DRB1*08:04:02, DRB1*08:04:03, DRB1*08:04:04, DRB1*08:04:05, DRB1*08:05, DRB1*08:06, DRB1*08:07, DRB1*08:08, DRB1*08:09, DRB1*08:10, DRB1*08:11, DRB1*08:12, DRB1*08:13, DRB1*08:14, DRB1*08:15, DRB1*08:16, DRB1*08:17, DRB1*08:18, DRB1*08:19, DRB1*08:20, DRB1*08:21, DRB1*08:22, DRB1*08:23, DRB1*08:24, DRB1*08:25, DRB1*08:26, DRB1*08:27, DRB1*08:28, DRB1*08:29, DRB1*08:30:01, DRB1*08:30:02, DRB1*08:31, DRB1*08:32, DRB1*08:33, DRB1*08:34, DRB1*08:35, DRB1*08:36, DRB1*08:37, DRB1*08:38, DRB1*08:39, DRB1*08:40, DRB1*09:01:02, DRB1*09:01:03, DRB1*09:01:04, DRB1*09:01:05, DRB1*09:01:06, DRB1*09:01:07, DRB1*09:02:01, DRB1*09:02:02, DRB1*09:03, DRB1*09:04, DRB1*09:05, DRB1*09:06, DRB1*09:07, DRB1*09:08, DRB1*09:09, DRB1*10:01:01, DRB1*10:01:02, DRB1*10:01:03, DRB1*10:02, DRB1*10:03, DRB1*11:01:01, DRB1*11:01:02, DRB1*11:01:03, DRB1*11:01:04, DRB1*11:01:05, DRB1*11:01:06, DRB1*11:01:07, DRB1*11:01:08, DRB1*11:01:09, DRB1*11:01:10, DRB1*11:01:11, DRB1*11:02:01, DRB1*11:02:02, DRB1*11:03, DRB1*11:04:01, DRB1*11:04:02, DRB1*11:04:03, DRB1*11:04:04, DRB1*11:04:05, DRB1*11:05, DRB1*11:06:01, DRB1*11:06:02, DRB1*11:07, DRB1*11:08:01, DRB1*11:08:02, DRB1*11:09, DRB1*11:10:01, DRB1*11:10:02, DRB1*11:11:01, DRB1*11:11:02, DRB1*11:12:01, DRB1*11:12:02, DRB1*11:13:01, DRB1*11:13:02, DRB1*11:14:01, DRB1*11:14:02, DRB1*11:15, DRB1*11:16, DRB1*11:17, DRB1*11:18, DRB1*11:19:01, DRB1*11:19:02, DRB1*11:20, DRB1*11:21, DRB1*11:22, DRB1*11:23, DRB1*11:24, DRB1*11:25, DRB1*11:26, DRB1*11:27:01, DRB1*11:27:02, DRB1*11:28:01, DRB1*11:28:02, DRB1*11:29, DRB1*11:30, DRB1*11:31, DRB1*11:32, DRB1*11:33, DRB1*11:34, DRB1*11:35, DRB1*11:36, DRB1*11:37, DRB1*11:38, DRB1*11:39, DRB1*11:40, DRB1*11:41, DRB1*11:42, DRB1*11:43, DRB1*11:44, DRB1*11:45, DRB1*11:46, DRB1*11:47, DRB1*11:48, DRB1*11:49, DRB1*11:50, DRB1*11:51, DRB1*11:52, DRB1*11:53, DRB1*11:54:01, DRB1*11:54:02, DRB1*11:55, DRB1*11:56, DRB1*11:57, DRB1*11:58:01, DRB1*11:58:02, DRB1*11:59, DRB1*11:60, DRB1*11:61, DRB1*11:62, DRB1*11:63, DRB1*11:64, DRB1*11:65:01, DRB1*11:65:02, DRB1*11:66, DRB1*11:67, DRB1*11:68, DRB1*11:69, DRB1*11:70, DRB1*11:72, DRB1*11:73, DRB1*11:74, DRB1*11:75, DRB1*11:76, DRB1*11:77, DRB1*11:78, DRB1*11:79, DRB1*11:80, DRB1*11:81, DRB1*11:82, DRB1*11:83, DRB1*11:84, DRB1*11:85, DRB1*11:86, DRB1*11:87, DRB1*11:88, DRB1*11:89, DRB1*11:90, DRB1*11:91, DRB1*11:92, DRB1*11:93, DRB1*11:94, DRB1*11:95, DRB1*11:96, DRB1*12:01:01, DRB1*12:01:02, DRB1*12:01:03, DRB1*12:02:01, DRB1*12:02:02, DRB1*12:02:03, DRB1*12:02:04, DRB1*12:02:05, DRB1*12:03:02, DRB1*12:04, DRB1*12:05, DRB1*12:06, DRB1*12:07, DRB1*12:08, DRB1*12:09, DRB1*12:10, DRB1*12:11, DRB1*12:12, DRB1*12:13, DRB1*12:14, DRB1*12:15, DRB1*12:16, DRB1*12:17, DRB1*12:18, DRB1*12:19, DRB1*12:20, DRB1*12:21, DRB1*12:22, DRB1*12:23, DRB1*13:01:01, DRB1*13:01:02, DRB1*13:01:03, DRB1*13:01:04, DRB1*13:01:05, DRB1*13:01:06, DRB1*13:01:07, DRB1*13:02:01, DRB1*13:02:02, DRB1*13:02:03, DRB1*13:03:01, DRB1*13:03:02, DRB1*13:03:03, DRB1*13:03:04, DRB1*13:03:05, DRB1*13:03:06, DRB1*13:04, DRB1*13:05:01, DRB1*13:05:02, DRB1*13:06, DRB1*13:07:01, DRB1*13:07:02, DRB1*13:08, DRB1*13:09, DRB1*13:10, DRB1*13:100, DRB1*13:101, DRB1*13:11:01, DRB1*13:11:02, DRB1*13:12, DRB1*13:13, DRB1*13:14:01, DRB1*13:14:02, DRB1*13:14:03, DRB1*13:15, DRB1*13:16, DRB1*13:17, DRB1*13:18, DRB1*13:19, DRB1*13:20, DRB1*13:21:01, DRB1*13:21:02, DRB1*13:22, DRB1*13:23, DRB1*13:24, DRB1*13:25, DRB1*13:26, DRB1*13:27, DRB1*13:28, DRB1*13:29, DRB1*13:30, DRB1*13:31, DRB1*13:32, DRB1*13:33:01, DRB1*13:33:02, DRB1*13:33:03, DRB1*13:34, DRB1*13:35, DRB1*13:36, DRB1*13:37, DRB1*13:38, DRB1*13:39, DRB1*13:40, DRB1*13:41, DRB1*13:42, DRB1*13:43, DRB1*13:44, DRB1*13:45, DRB1*13:46, DRB1*13:47, DRB1*13:48, DRB1*13:49, DRB1*13:50:01, DRB1*13:50:02, DRB1*13:51, DRB1*13:52, DRB1*13:53, DRB1*13:54, DRB1*13:55, DRB1*13:56, DRB1*13:57, DRB1*13:58, DRB1*13:59, DRB1*13:60, DRB1*13:61, DRB1*13:62, DRB1*13:63, DRB1*13:64, DRB1*13:65, DRB1*13:66:01, DRB1*13:66:02, DRB1*13:67, DRB1*13:68, DRB1*13:69, DRB1*13:70, DRB1*13:71, DRB1*13:72, DRB1*13:73, DRB1*13:74, DRB1*13:75, DRB1*13:76, DRB1*13:77, DRB1*13:78, DRB1*13:79, DRB1*13:80, DRB1*13:81, DRB1*13:82, DRB1*13:83, DRB1*13:84, DRB1*13:85, DRB1*13:86, DRB1*13:87, DRB1*13:88, DRB1*13:89, DRB1*13:90, DRB1*13:91, DRB1*13:92, DRB1*13:93, DRB1*13:94, DRB1*13:95, DRB1*13:96, DRB1*13:97, DRB1*13:98, DRB1*13:99, DRB1*14:01:01, DRB1*14:01:02, DRB1*14:01:03, DRB1*14:02, DRB1*14:03:01, DRB1*14:03:02, DRB1*14:04, DRB1*14:05:01, DRB1*14:05:02, DRB1*14:05:03, DRB1*14:06:01, DRB1*14:06:02, DRB1*14:07:01, DRB1*14:07:02, DRB1*14:08, DRB1*14:09, DRB1*14:10, DRB1*14:11, DRB1*14:12, DRB1*14:13, DRB1*14:

14, DRB1*14:15, DRB1*14:16, DRB1*14:17, DRB1*14:18, DRB1*14:19, DRB1*14:20, DRB1*14:21, DRB1*14:22, DRB1*14:23:01, DRB1*14:23:02, DRB1*14:23:03, DRB1*14:24, DRB1*14:25, DRB1*14:26, DRB1*14:27, DRB1*14:28, DRB1*14:29, DRB1*14:30, DRB1*14:31, DRB1*14:32:01, DRB1*14:32:02, DRB1*14:33, DRB1*14:34, DRB1*14:35, DRB1*14:36, DRB1*14:37, DRB1*14:38, DRB1*14:39, DRB1*14:40, DRB1*14:41, DRB1*14:42, DRB1*14:43, DRB1*14:44:01, DRB1*14:44:02, DRB1*14:45, DRB1*14:46, DRB1*14:47, DRB1*14:48, DRB1*14:49, DRB1*14:50, DRB1*14:51, DRB1*14:52, DRB1*14:53, DRB1*14:54, DRB1*14:55, DRB1*14:56, DRB1*14:57, DRB1*14:58, DRB1*14:59, DRB1*14:60, DRB1*14:61, DRB1*14:62, DRB1*14:63, DRB1*14:64, DRB1*14:65, DRB1*14:67, DRB1*14:68, DRB1*14:69, DRB1*14:70, DRB1*14:71, DRB1*14:72, DRB1*14:73, DRB1*14:74, DRB1*14:75, DRB1*14:76, DRB1*14:77, DRB1*14:78, DRB1*14:79, DRB1*14:80, DRB1*14:81, DRB1*14:82, DRB1*14:83, DRB1*14:84, DRB1*14:85, DRB1*14:86, DRB1*14:87, DRB1*14:88, DRB1*14:89, DRB1*14:90, DRB1*14:91, DRB1*14:93, DRB1*14:94, DRB1*14:95, DRB1*14:96, DRB1*14:97, DRB1*14:98, DRB1*14:99, DRB1*15:01:01:01, DRB1*15:01:01:02, DRB1*15:01:02, DRB1*15:01:03, DRB1*15:01:04, DRB1*15:01:05, DRB1*15:01:06, DRB1*15:01:07, DRB1*15:01:08, DRB1*15:01:09, DRB1*15:01:10, DRB1*15:01:11, DRB1*15:01:12, DRB1*15:02:01, DRB1*15:02:02, DRB1*15:02:03, DRB1*15:02:04, DRB1*15:02:05, DRB1*15:02:06, DRB1*15:02:07, DRB1*15:03:01:01, DRB1*15:03:01:02, DRB1*15:04, DRB1*15:05, DRB1*15:06, DRB1*15:07, DRB1*15:08, DRB1*15:09, DRB1*15:10, DRB1*15:11, DRB1*15:12, DRB1*15:13, DRB1*15:14, DRB1*15:15, DRB1*15:16, DRB1*15:18, DRB1*15:19, DRB1*15:20, DRB1*15:21, DRB1*15:22, DRB1*15:23, DRB1*15:24, DRB1*15:25, DRB1*15:26, DRB1*15:27, DRB1*15:28, DRB1*15:29, DRB1*15:30, DRB1*15:31, DRB1*15:32, DRB1*15:33, DRB1*15:34, DRB1*15:35, DRB1*15:36, DRB1*15:37, DRB1*15:38, DRB1*15:39, DRB1*15:40, DRB1*15:41, DRB1*15:42, DRB1*15:43, DRB1*15:44, DRB1*15:45, DRB1*15:46, DRB1*15:47, DRB1*15:48, DRB1*15:49, DRB1*16:01:01, DRB1*16:01:02, DRB1*16:02:01, DRB1*16:02:02, DRB1*16:03, DRB1*16:04, DRB1*16:05:01, DRB1*16:05:02, DRB1*16:07, DRB1*16:08, DRB1*16:09, DRB1*16:10, DRB1*16:11, DRB1*16:12, DRB1*16:14, DRB1*16:15, DRB1*16:16, DRB2*01:01, DRB3*01:01:02:01, DRB3*01:01:02:02, DRB3*01:01:03, DRB3*01:01:04, DRB3*01:01:05, DRB3*01:02, DRB3*01:03, DRB3*01:04, DRB3*01:05, DRB3*01:06, DRB3*01:07, DRB3*01:08, DRB3*01:09, DRB3*01:10, DRB3*01:11, DRB3*01:12, DRB3*01:13, DRB3*01:14, DRB3*02:01, DRB3*02:02:01, DRB3*02:02:02, DRB3*02:02:03, DRB3*02:02:04, DRB3*02:02:05, DRB3*02:03, DRB3*02:04, DRB3*02:05, DRB3*02:06, DRB3*02:07, DRB3*02:08, DRB3*02:09, DRB3*02:10, DRB3*02:11, DRB3*02:12, DRB3*02:13, DRB3*02:14, DRB3*02:15, DRB3*02:16, DRB3*02:17, DRB3*02:18, DRB3*02:19, DRB3*02:20, DRB3*02:21, DRB3*02:22, DRB3*02:23, DRB3*02:24, DRB3*02:25, DRB3*03:01:01, DRB3*03:01:02, DRB3*03:01:03, DRB3*03:02, DRB3*03:03, DRB4*01:01:01:01, DRB4*01:02, DRB4*01:03:01:01, DRB4*01:03:02, DRB4*01:03:03, DRB4*01:03:04, DRB4*01:04, DRB4*01:05, DRB4*01:06, DRB4*01:07, DRB4*01:08, DRB5*01:01:01, DRB5*01:01:02, DRB5*01:02, DRB5*01:03, DRB5*01:04, DRB5*01:05, DRB5*01:06, DRB5*01:07, DRB5*01:09, DRB5*01:11, DRB5*01:12, DRB5*01:13, DRB5*01:14, DRB5*02:02, DRB5*02:03, DRB5*02:04, DRB5*02:05, DRB6*01:01, DRB6*02:01, DRB6*02:02, DRB7*01:01:01, DRB7*01:01:02, DRB8*01:01, DRB9*01:01, DQA1*01:01:01, DQA1*01:01:02, DQA1*01:02:01, DQA1*01:02:02, DQA1*01:02:03, DQA1*01:02:04, DQA1*01:03, DQA1*01:04:01, DQA1*01:04:02, DQA1*01:05, DQA1*01:06, DQA1*01:07, DQA1*02:01, DQA1*03:01:01, DQA1*03:02, DQA1*03:03, DQA1*04:01:01, DQA1*04:01:02, DQA1*04:02, DQA1*04:04, DQA1*05:01:01, DQA1*05:01:02, DQA1*05:02, DQA1*05:03, DQA1*05:04, DQA1*05:05, DQA1*05:06, DQA1*05:07, DQA1*05:08, DQA1*05:09, DQA1*05:10, DQA1*06:01:01, DQA1*06:01:02, DQA1*06:02, DQB1*02:01:01, DQB1*02:01:02, DQB1*02:02, DQB1*02:03, DQB1*02:04, DQB1*02:05, DQB1*03:01:01, DQB1*03:01:02, DQB1*03:01:03, DQB1*03:01:04, DQB1*03:02:01, DQB1*03:02:02, DQB1*03:02:03, DQB1*03:02:04, DQB1*03:02:05, DQB1*03:03:02, DQB1*03:03:03, DQB1*03:04, DQB1*03:05:01, DQB1*03:05:02, DQB1*03:05:03, DQB1*03:05:04, DQB1*03:06, DQB1*03:07, DQB1*03:08, DQB1*03:09, DQB1*03:10, DQB1*03:11, DQB1*03:12, DQB1*03:13, DQB1*03:14, DQB1*03:15, DQB1*03:16, DQB1*03:17, DQB1*03:18, DQB1*03:19, DQB1*03:20, DQB1*03:21, DQB1*03:22, DQB1*03:23, DQB1*03:24, DQB1*03:25, DQB1*03:26, DQB1*03:27, DQB1*04:01:01, DQB1*04:01:02, DQB1*04:02, DQB1*04:03:01, DQB1*04:03:02, DQB1*04:04, DQB1*04:05, DQB1*05:01:01, DQB1*05:01:02, DQB1*05:02:01, DQB1*05:02:02, DQB1*05:03:01, DQB1*05:03:02, DQB1*05:04, DQB1*05:05, DQB1*05:06, DQB1*06:01:01, DQB1*06:01:02, DQB1*06:01:03, DQB1*06:01:04, DQB1*06:01:05, DQB1*06:02:01, DQB1*06:02:02, DQB1*06:03:01, DQB1*06:03:02, DQB1*06:04:01, DQB1*06:04:02, DQB1*06:04:03, DQB1*06:05:01, DQB1*06:05:02, DQB1*06:06, DQB1*06:07, DQB1*06:08:01, DQB1*06:08:02, DQB1*06:09, DQB1*06:10, DQB1*06:11:01, DQB1*06:11:02, DQB1*06:12, DQB1*06:13, DQB1*06:14:01, DQB1*06:14:02, DQB1*06:15, DQB1*06:16, DQB1*06:17, DQB1*06:18, DQB1*06:19, DQB1*06:20, DQB1*06:21, DQB1*06:22, DQB1*06:23, DQB1*06:24, DQB1*06:25, DQB1*06:27, DQB1*06:28, DQB1*06:29, DQB1*06:30, DQB1*06:31, DQB1*06:32, DQB1*06:33, DQB1*06:34, DQB1*06:35, DQB1*06:36, DQB1*06:37, DQB1*06:38, DQB1*06:39, DQB1*06:40, DPA1*01:03:01, DPA1*01:03:02, DPA1*01:03:03, DPA1*01:03:04, DPA1*01:04, DPA1*01:05, DPA1*01:06:01, DPA1*01:06:02, DPA1*01:07, DPA1*01:08, DPA1*01:09, DPA1*01:10, DPA1*02:01:01, DPA1*02:01:02, DPA1*02:01:03, DPA1*02:01:04, DPA1*02:01:05, DPA1*02:01:06, DPA1*02:01:07, DPA1*02:02:01, DPA1*02:02:02, DPA1*02:02:03, DPA1*02:03, DPA1*02:04, DPA1*03:01, DPA1*03:02, DPA1*03:03, DPA1*04:01, DPB1*01:01:01, DPB1*01:01:02, DPB1*01:01:03, DPB1*02:01:02, DPB1*02:01:03, DPB1*02:01:04, DPB1*02:01:05, DPB1*02:01:06, DPB1*02:01:07, DPB1*02:02, DPB1*03:01:01, DPB1*03:01:02, DPB1*04:01:01, DPB1*04:01:02, DPB1*04:02, DPB1*05:01:01, DPB1*05:01:02, DPB1*06:01, DPB1*08:01, DPB1*09:01, DPB1*100:01, DPB1*101:01, DPB1*102:01, DPB1*103:01, DPB1*104:01, DPB1*105:01, DPB1*106:01, DPB1*107:01, DPB1*108:01, DPB1*109:01, DPB1*10:01, DPB1*110:01, DPB1*111:01, DPB1*112:01, DPB1*113:01, DPB1*114:01, DPB1*115:01, DPB1*116:01, DPB1*117:01, DPB1*118:01, DPB1*119:01, DPB1*11:01:01, DPB1*11:01:02, DPB1*121:01, DPB1*122:01, DPB1*123:01, DPB1*124:01, DPB1*125:01, DPB1*126:01, DPB1*127:01,

DPB1*128:01, DPB1*13:01, DPB1*14:01, DPB1*15:01, DPB1*16:01, DPB1*17:01, DPB1*18:01, DPB1*19:01, DPB1*20:01:01, DPB1*20:01:02, DPB1*21:01, DPB1*22:01, DPB1*23:01, DPB1*24:01, DPB1*25:01, DPB1*26:01, DPB1*26:01:02, DPB1*27:01, DPB1*28:01, DPB1*29:01, DPB1*30:01, DPB1*31:01, DPB1*32:01, DPB1*33:01, DPB1*34:01, DPB1*35:01:01, DPB1*35:01:02, DPB1*36:01, DPB1*37:01, DPB1*38:01, DPB1*39:01, DPB1*40:01, DPB1*41:01:01, DPB1*41:01:02, DPB1*44:01, DPB1*45:01, DPB1*46:01, DPB1*47:01, DPB1*48:01, DPB1*49:01, DPB1*50:01, DPB1*51:01, DPB1*52:01, DPB1*53:01, DPB1*54:01, DPB1*55:01, DPB1*56:01, DPB1*57:01, DPB1*58:01, DPB1*59:01, DPB1*60:01, DPB1*62:01, DPB1*63:01, DPB1*65:01, DPB1*66:01, DPB1*67:01, DPB1*68:01, DPB1*69:01, DPB1*70:01, DPB1*71:01, DPB1*72:01, DPB1*73:01, DPB1*74:01, DPB1*75:01, DPB1*76:01, DPB1*77:01, DPB1*78:01, DPB1*79:01, DPB1*80:01, DPB1*81:01, DPB1*82:01, DPB1*83:01, DPB1*84:01, DPB1*85:01, DPB1*86:01, DPB1*87:01, DPB1*88:01, DPB1*89:01, DPB1*90:01, DPB1*91:01, DPB1*92:01, DPB1*93:01, DPB1*94:01, DPB1*95:01, DPB1*96:01, DPB1*97:01, DPB1*98:01, DPB1*99:01, DMA*01:01, DMA*01:02, DMA*01:03, DMA*01:04, DMB*01:01, DMB*01:02, DMB*01:03, DMB*01:04, DMB*01:05, DMB*01:06, DMB*01:07, DOA*01:01:01, DOA*01:01:02:01, DOA*01:01:02:02, DOA*01:01:02:03, DOA*01:01:03, DOA*01:01:04:01, DOA*01:01:04:02, DOA*01:01:05, DOA*01:01:06, DOA*01:02, DOA*01:03, DOB*01:01:01:01, DOB*01:01:01:02, DOB*01:01:02, DOB*01:01:03, DOB*01:02:01, DOB*01:02:02, DOB*01:03, DOB*01:04:01:01, DOB*01:04:01:02, MICA*001, MICA*002:01, MICA*002:02, MICA*002:03, MICA*004, MICA*005, MICA*006, MICA*007:01, MICA*007:02, MICA*007:03, MICA*008:01, MICA*008:02, MICA*008:03, MICA*008:04, MICA*009:01, MICA*009:02, MICA*010, MICA*011, MICA*012:01, MICA*012:02, MICA*012:03, MICA*013, MICA*014, MICA*015, MICA*016, MICA*017, MICA*018:01, MICA*018:02, MICA*019, MICA*020, MICA*022, MICA*023, MICA*024, MICA*025, MICA*026, MICA*027, MICA*028, MICA*029, MICA*030, MICA*031, MICA*032, MICA*033, MICA*034, MICA*035, MICA*036, MICA*037, MICA*038, MICA*039, MICA*040, MICA*041, MICA*042, MICA*043, MICA*044, MICA*045, MICA*046, MICA*047, MICA*048, MICA*049, MICA*050, MICA*051, MICA*052, MICA*053, MICA*054, MICA*055, MICA*056, MICA*057, MICA*058, MICA*059, MICA*060, MICA*061, MICA*062, MICA_, MICB*001, MICB*002:01:01, MICB*002:01:02, MICB*003, MICB*004:01:01, MICB*004:01:02, MICB*005:01, MICB*005:02:01, MICB*005:02:02, MICB*005:02:03, MICB*005:02:04, MICB*005:03, MICB*005:04, MICB*005:05, MICB*006, MICB*007, MICB*008, MICB*010, MICB*011, MICB*012, MICB*013, MICB*014, MICB*015, MICB*016, MICB*018, MICB*019, MICB*020, MICB*022, MICB_, TAP1*01:01, TAP1*02:01:01, TAP1*02:01:02, TAP1*03:01, TAP1*04:01, TAP1*05:01, TAP1_, TAP2*01:01, TAP2*01:02, TAP2*01:03, TAP2*02:01, TAP2_, KIR2DL1*001, KIR2DL1*0020101, KIR2DL1*0020102, KIR2DL1*0020103, KIR2DL1*00301, KIR2DL1*0030201, KIR2DL1*0030202, KIR2DL1*0030203, KIR2DL1*0030204, KIR2DL1*0030205, KIR2DL1*0030206, KIR2DL1*0030207, KIR2DL1*0030208, KIR2DL1*0030209, KIR2DL1*0030210, KIR2DL1*00303, KIR2DL1*0040101, KIR2DL1*0040102, KIR2DL1*00402, KIR2DL1*00403, KIR2DL1*005, KIR2DL1*006, KIR2DL1*007, KIR2DL1*008, KIR2DL1*009, KIR2DL1*010, KIR2DL1*01101, KIR2DL1*01102, KIR2DL1*01201, KIR2DL1*014, KIR2DL1*015, KIR2DL1*016, KIR2DL1*017, KIR2DL1*018, KIR2DL1*019, KIR2DL1*025, KIR2DL2*0010101, KIR2DL2*0010102, KIR2DL2*0010103, KIR2DL2*0010104, KIR2DL2*0010105, KIR2DL2*0010106, KIR2DL2*0010107, KIR2DL*00102, KIR2DL2*002, KIR2DL2*0030101, KIR2DL2*0030102, KIR2DL2*0030103, KIR2DL2*0030104, KIR2DL2*0030105, KIR2DL2*0030106, KIR2DL2*0030107, KIR2DL2*00302, KIR2DL2*00303, KIR2DL2*00304, KIR2DL2*004, KIR2DL2*005, KIR2DL2*00601, KIR2DL2*00602, KIR2DL2*007, KIR2DL2*008, KIR2DL2*009, KIR2DL2*010, KIR2DL3*0010101, KIR2DL3*0010102, KIR2DL3*0010103, KIR2DL3*0010104, KIR2DL3*0010105, KIR2DL3*0010106, KIR2DL3*0010107, KIR2DL3*0010108, KIR2DL3*0010109, KIR2DL3*0010110, KIR2DL3*0010111, KIR2DL3*00102, KIR2DL3*00103, KIR2DL3*00104, KIR2DL3*0020101, KIR2DL3*0020102, KIR2DL3*0020103, KIR2DL3*003, KIR2DL3*004, KIR2DL3*005, KIR2DL3*006, KIR2DL3*007, KIR2DL3*009, KIR2DL3*010, KIR2DL3*011, KIR2DL3*01201, KIR2DL3*013, KIR2DL3*014, KIR2DL3*015, KIR2DL3*016, KIR2DL3*017, KIR2DL4*00101, KIR2DL4*0010201, KIR2DL4*0010202, KIR2DL4*0010301, KIR2DL4*0010302, KIR2DL4*0010303, KIR2DL4*0010304, KIR2DL4*0010305, KIR2DL4*0010306, KIR2DL4*0010307, KIR2DL4*0010308, KIR2DL4*00104, KIR2DL4*00105, KIR2DL4*00201, KIR2DL4*00202, KIR2DL4*003, KIR2DL4*004, KIR2DL4*00501, KIR2DL4*00502, KIR2DL4*00601, KIR2DL4*00602, KIR2DL4*007, KIR2DL4*0080101, KIR2DL4*0080102, KIR2DL4*0080103, KIR2DL4*0080104, KIR2DL4*0080105, KIR2DL4*0080201, KIR2DL4*0080202, KIR2DL4*0080203, KIR2DL4*0080204, KIR2DL4*00901, KIR2DL4*010, KIR2DL4*011, KIR2DL4*01201, KIR2DL4*013, KIR2DL4*017, KIR2DL5A*0010101, KIR2DL5A*0010102, KIR2DL5A*0010103, KIR2DL5A*00102, KIR2DL5A*00103, KIR2DL5A*00104, KIR2DL5A*00105, KIR2DL5A*0050101, KIR2DL5A*0050102, KIR2DL5A*0050103, KIR2DL5A*0050104, KIR2DL5A*01201, KIR2DL5A*01202, KIR2DL5B*0020101, KIR2DL5B*0020102, KIR2DL5B*0020103, KIR2DL5B*0020104, KIR2DL5B*0020105, KIR2DL5B*0020106, KIR2DL5B*0020107, KIR2DL5B*00202, KIR2DL5B*003, KIR2DL5B*004, KIR2DL5B*00601, KIR2DL5B*00602, KIR2DL5B*00603, KIR2DL5B*007, KIR2DL5B*0070102, KIR2DL5B*0080101, KIR2DL5B*0080102, KIR2DL5B*00802, KIR2DL5B*009, KIR2DL5B*010, KIR2DL5B*011, KIR2DL5B*01301, KIR2DL5B*01302, KIR2DL5B*01303, KIR2DP1*00101, KIR2DP1*0010201, KIR2DP1*0010202, KIR2DP1*0010203, KIR2DP1*0020101, KIR2DP1*0020102, KIR2DP1*0020103, KIR2DP1*0020104, KIR2DP1*0020105, KIR2DP1*0020106,

KIR2DP1*0020107, KIR2DP1*0020108, KIR2DP1*0020109, KIR2DP1*0030101, KIR2DP1*0030102, KIR2DP1*004, KIR2DP1*005, KIR2DP1*006, KIR2DP1*007, KIR2DP1*008, KIR2DP1*009, KIR2DP1*010, KIR2DS1*001, KIR2DS1*0020101, KIR2DS1*0020102, KIR2DS1*0020103, KIR2DS1*0020104, KIR2DS1*0020105, KIR2DS1*0020106, KIR2DS1*00202, KIR2DS1*00301, KIR2DS1*00302, KIR2DS1*004, KIR2DS1*00501, KIR2DS1*00502, KIR2DS1*006, KIR2DS1*008, KIR2DS2*0010101, KIR2DS2*0010102, KIR2DS2*0010103, KIR2DS2*0010104, KIR2DS2*0010105, KIR2DS2*0010106, KIR2DS2*0010107, KIR2DS2*0010108, KIR2DS2*0010109, KIR2DS2*0010110, KIR2DS2*0010111, KIR2DS2*0010112, KIR2DS2*00102, KIR2DS2*00103, KIR2DS2*00104, KIR2DS2*002, KIR2DS2*003, KIR2DS2*004, KIR2DS2*005, KIR2DS2*006, KIR2DS3*00101, KIR2DS3*00102, KIR2DS3*0010301, KIR2DS3*0010302, KIR2DS3*00104, KIR2DS3*00105, KIR2DS3*00106, KIR2DS3*0020101, KIR2DS3*0020102, KIR2DS3*0020103, KIR2DS3*004, KIR2DS4*0010101, KIR2DS4*0010102, KIR2DS4*0010103, KIR2DS4*0010104, KIR2DS4*0010105, KIR2DS4*0010106, KIR2DS4*0010107, KIR2DS4*0010108, KIR2DS4*0010109, KIR2DS4*00102, KIR2DS4*00103, KIR2DS4*00104, KIR2DS4*0030101, KIR2DS4*0030102, KIR2DS4*0030103, KIR2DS4*0030104, KIR2DS4*0040101, KIR2DS4*0040102, KIR2DS4*0060101, KIR2DS4*0060102, KIR2DS4*007, KIR2DS4*008, KIR2DS4*009, KIR2DS4*010, KIR2DS4*01101, KIR2DS4*01102, KIR2DS4*012, KIR2DS4*013, KIR2DS4*014, KIR2DS4*015, KIR2DS5*001, KIR2DS5*0020101, KIR2DS5*0020102, KIR2DS5*0020103, KIR2DS5*0020104, KIR2DS5*003, KIR2DS5*004, KIR2DS5*005, KIR2DS5*006, KIR2DS5*007, KIR2DS5*00801, KIR2DS5*00802, KIR2DS5*009, KIR2DS5*010, KIR3DL1*0010101, KIR3DL1*0010102, KIR3DL1*00102, KIR3DL1*002, KIR3DL1*00401, KIR3DL1*00402, KIR3DL1*0050101, KIR3DL1*0050102, KIR3DL1*00502, KIR3DL1*006, KIR3DL1*0070101, KIR3DL1*0070102, KIR3DL1*008, KIR3DL1*009, KIR3DL1*01501, KIR3DL1*0150201, KIR3DL1*0150202, KIR3DL1*0150203, KIR3DL1*01503, KIR3DL1*016, KIR3DL1*01701, KIR3DL1*01702, KIR3DL1*018, KIR3DL1*019, KIR3DL1*020, KIR3DL1*021, KIR3DL1*022, KIR3DL1*023, KIR3DL1*025, KIR3DL1*026, KIR3DL1*027, KIR3DL1*028, KIR3DL1*0290101, KIR3DL1*0290102, KIR3DL1*030, KIR3DL1*03101, KIR3DL1*03102, KIR3DL1*032, KIR3DL1*033, KIR3DL1*034, KIR3DL1*035, KIR3DL1*036, KIR3DL1*037, KIR3DL1*038, KIR3DL1*039, KIR3DL1*040, KIR3DL1*041, KIR3DL1*042, KIR3DL1*043, KIR3DL1*044, KIR3DL1*051, KIR3DL1*052, KIR3DL1*053, KIR3DL1*054, KIR3DL1*056, KIR3DL1*057, KIR3DL1*059, KIR3DL1*060, KIR3DL1*061, KIR3DL1*062, KIR3DL1*063, KIR3DL1*064, KIR3DL1*065, KIR3DL1*066, KIR3DL1*067, KIR3DL1*068, KIR3DL1*072, KIR3DL2*0010101, KIR3DL2*0010102, KIR3DL2*00102, KIR3DL2*0010301, KIR3DL2*0010302, KIR3DL2*0020101, KIR3DL2*0020102, KIR3DL2*0020103, KIR3DL2*0020104, KIR3DL2*0020105, KIR3DL2*0020106, KIR3DL2*00202, KIR3DL2*00301, KIR3DL2*00302, KIR3DL2*004, KIR3DL2*00501, KIR3DL2*006, KIR3DL2*0070101, KIR3DL2*0070102, KIR3DL2*0070103, KIR3DL2*008, KIR3DL2*00901, KIR3DL2*00902, KIR3DL2*00903, KIR3DL2*010, KIR3DL2*011, KIR3DL2*012, KIR3DL2*01301, KIR3DL2*014, KIR3DL2*015, KIR3DL2*016, KIR3DL2*017, KIR3DL2*018, KIR3DL2*019, KIR3DL2*020, KIR3DL2*021, KIR3DL2*022, KIR3DL2*023, KIR3DL2*056, KIR3DL3*00101, KIR3DL3*00102, KIR3DL3*00103, KIR3DL3*00201, KIR3DL3*00202, KIR3DL3*00203, KIR3DL3*00204, KIR3DL3*00205, KIR3DL3*00206, KIR3DL3*00207, KIR3DL3*00208, KIR3DL3*0030101, KIR3DL3*0030102, KIR3DL3*0030103, KIR3DL3*0030104, KIR3DL3*00401, KIR3DL3*0040201, KIR3DL3*0040202, KIR3DL3*005, KIR3DL3*00601, KIR3DL3*00602, KIR3DL3*007, KIR3DL3*00801, KIR3DL3*00802, KIR3DL3*0090101, KIR3DL3*0090102, KIR3DL3*0090103, KIR3DL3*00902, KIR3DL3*00903, KIR3DL3*01001, KIR3DL3*01002, KIR3DL3*01101, KIR3DL3*01102, KIR3DL3*012, KIR3DL3*01301, KIR3DL3*01302, KIR3DL3*01303, KIR3DL3*01304, KIR3DL3*01305, KIR3DL3*01306, KIR3DL3*01307, KIR3DL3*01401, KIR3DL3*0140201, KIR3DL3*0140202, KIR3DL3*0140203, KIR3DL3*01403, KIR3DL3*01404, KIR3DL3*01405, KIR3DL3*01406, KIR3DL3*01501, KIR3DL3*01502, KIR3DL3*01601, KIR3DL3*01602, KIR3DL3*017, KIR3DL3*01801, KIR3DL3*019, KIR3DL3*020, KIR3DL3*02101, KIR3DL3*02102, KIR3DL3*022, KIR3DL3*023, KIR3DL3*02501, KIR3DL3*02502, KIR3DL3*026, KIR3DL3*02701, KIR3DL3*028, KIR3DL3*029, KIR3DL3*030, KIR3DL3*031, KIR3DL3*032, KIR3DL3*033, KIR3DL3*034, KIR3DL3*035, KIR3DL3*036, KIR3DL3*048, KIR3DP1*001, KIR3DP1*002, KIR3DP1*0030101, KIR3DP1*0030102, KIR3DP1*0030201, KIR3DP1*0030202, KIR3DP1*0030203, KIR3DP1*0030204, KIR3DP1*0030205, KIR3DP1*0030206, KIR3DP1*00303, KIR3DP1*0030401, KIR3DP1*0030402, KIR3DP1*004, KIR3DP1*005, KIR3DP1*006, KIR3DP1*007, KIR3DP1*008, KIR3DP1*0090101, KIR3DP1*0090102, KIR3DP1*0090103, KIR3DP1*00902, KIR3DP1*010, KIR3DS1*010, KIR3DS1*011, KIR3DS1*012, KIR3DS1*0130101, KIR3DS1*0130102, KIR3DS1*0130103, KIR3DS1*01302, KIR3DS1*014, KIR3DS1*045, KIR3DS1*046, KIR3DS1*047, KIR3DS1*048, KIR3DS1*050, KIR3DS1*055, KIR3DS1*058, B2M, TAPBP_variant1, TAPBP_variant2, TAPBP_variant3, CANX_variant1, CANX_variant2, CALR, PDIA2, PDIA3, ERAP1_variant1, ERAP1_variant2, TPP2, BLMH, LAP3, PSMA1_variant1, PSMA1_variant2, PSMA1_variant3, PSMA2, PSMA3_variant1, PSMA3_variant2, PSMA4_variant1, PSMA4_variant2, PSMA4_variant3, PSMA5, PSMA6, PSMA7, PSMA8_variant1, PSMA8_variant2, PSMA8_variant3, PSMB1, PSMB2, PSMB3, PSMB4, PSMB5_variant1, PSMB5_variant2, PSMB5_variant3, PSMB6, PSMB7, PSMB8_variant1, PSMB8_variant2, PSMB9, PSMB10, PSMB11, PSMC1, PSMC2, PSMC3, PSMC4_variant1, PSMC4_variant2, PSMC5, PSMC6, PSMD1_variant1, PSMD1_variant2, PSMD2, PSMD3, PSMD4, PSMD5, PSMD6, PSMD7, PSMD8, PSMD9, PSMD10_variant1, PSMD10_variant2, PSMD11, PSMD12_variant1, PSMD12_variant2, PSMD13_variant1, PSMD13_variant2, and PSMD14.

Within another specific embodiment, the oligonucleotide array comprises the capture oligonucleotides having the nucleic acid sequences set forth in Table X, below, or the oligonucleotide array comprises the oligonucleotides in Table X that have names beginning with "HPT", "HPE" or "HPN" as shown in Table X. In Table X, oligo names start with "HNN", "HPN", "HPE" or "HPT." "HNN" indicates that the oligo is a negative control oligonucleotide. "HPN" indicates a "normal" (unchanged) oligo, "HPT" indicates a "truncated" oligo, and "HPE" indicates an "extended" oligo. The "HPT" and "HPE" modifications were made to ensure proper melting temperature. The "HPT", "HPE" or "HPN" oligios in Table X are designed to collectively target transcripts (e.g., cDNA or cRNA) encoding a subset of clinically relevant HLA molecules as well as their 5'UTR regions. The Table also contains negative control oligos, which help better identification of thresholds for positive and negative signals. Further, in certain embodiments, it may be desirable to detect changes in 5' UTR sequences, since such changes may result in altered expression of HLA transcripts due to regulation of transcription. The clinically relevant HLA alleles targeted by the oligos in Table X include: A*01:01:01:01, A*01:01:01:01, A*01:01:02, A*01:01:03, A*01:01:04, A*01:01:05, A*01:01:06, A*01:01:07, A*01:01:08, A*01:01:09, A*01:01:10, A*01:01:11, A*01:01:12, A*01:01:13, A*01:01:14, A*01:01:15, A*01:01:16, A*01:01:17, A*01:01:18, A*01:01:19, A*01:01:20, A*01:01:21, A*01:01:22, A*01:01:23, A*01:01:24, A*01:01:25, A*01:01:26, A*01:01:27, A*01:01:28, A*01:01:29, A*01:01:30, A*01:01:31, A*01:01:32, A*01:01:33, A*01:01:34, A*01:01:35, A*01:01:36, A*01:01:37, A*01:01:39, A*01:01:40, A*01:01:41, A*01:01:42, A*01:01:43, A*01:02, A*01:03, A*02:01:01:01, A*02:01:01:03, A*02:01:02, A*02:01:03, A*02:01:04, A*02:01:05, A*02:01:06, A*02:01:07, A*02:01:08, A*02:01:09, A*02:01:10, A*02:01:11, A*02:01:12, A*02:01:13, A*02:01:15, A*02:01:17, A*02:01:18, A*02:01:19, A*02:01:21, A*02:01:22, A*02:01:23, A*02:01:24, A*02:01:25, A*02:01:26, A*02:01:27, A*02:01:28, A*02:01:29, A*02:01:30, A*02:01:31, A*02:01:32, A*02:01:33, A*02:01:34, A*02:01:35, A*02:01:36, A*02:01:37, A*02:01:38, A*02:01:39, A*02:01:40, A*02:01:41, A*02:01:42, A*02:01:43, A*02:01:44, A*02:01:45, A*02:01:46, A*02:01:47, A*02:01:48, A*02:01:49, A*02:01:50, A*02:01:51, A*02:01:52, A*02:01:53, A*02:01:54, A*02:01:55, A*02:01:56, A*02:01:57, A*02:01:58, A*02:01:59, A*02:01:60, A*02:01:61, A*02:01:62, A*02:01:63, A*02:02, A*02:03:01, A*02:03:02, A*02:03:03, A*02:03:04, A*02:04, A*02:05:01, A*02:05:02, A*02:05:03, A*02:05:04, A*02:05:05, A*02:06:01, A*02:06:02, A*02:06:03, A*02:06:04, A*02:06:05, A*02:06:06, A*02:06:07, A*02:06:08, A*02:06:09, A*02:06:10, A*02:07, A*02:08, A*02:09, A*02:10, A*02:11:01, A*02:11:02, A*02:11:03, A*02:11:04, A*02:12, A*02:13, A*02:14, A*02:16, A*02:17:01, A*02:17:02, A*02:19, A*02:20:01, A*02:20:02, A*02:21, A*02:22:01, A*02:22:02, A*02:24:01, A*02:24:02, A*02:25, A*02:26, A*02:27, A*02:30, A*02:34, A*02:36, A*02:37, A*02:38, A*02:42, A*02:44, A*02:45, A*02:49, A*02:51, A*02:54, A*02:55, A*02:58, A*02:60:01, A*02:60:02, A*02:67, A*02:74:01, A*02:74:02, A*03:01:01:01, A*03:01:01:03, A*03:01:02, A*03:01:03, A*03:01:04, A*03:01:05, A*03:01:06, A*03:01:07, A*03:01:08, A*03:01:09, A*03:01:10, A*03:01:11, A*03:01:12, A*03:01:13, A*03:01:14, A*03:01:15, A*03:01:16, A*03:01:17, A*03:01:18, A*03:01:19, A*03:01:20, A*03:01:21, A*03:01:22, A*03:01:23, A*03:01:24, A*03:01:25, A*03:01:26, A*03:01:27, A*03:01:28, A*03:01:29, A*03:01:30, A*03:01:31, A*03:02:01, A*03:02:02, A*03:05, A*03:07, A*03:08, A*03:10, A*11:01:01, A*11:01:02, A*11:01:03, A*11:01:04, A*11:01:05, A*11:01:06, A*11:01:07, A*11:01:08, A*11:01:09, A*11:01:10, A*11:01:11, A*11:01:12, A*11:01:13, A*11:01:14, A*11:01:15, A*11:01:16, A*11:01:17, A*11:01:18, A*11:01:19, A*11:01:20, A*11:01:21, A*11:01:22, A*11:01:23, A*11:01:24, A*11:01:25, A*11:01:26, A*11:01:27, A*11:01:28, A*11:01:29, A*11:01:30, A*11:01:31, A*11:01:32, A*11:02:01, A*11:02:02, A*11:02:03, A*11:03, A*11:04, A*11:05, A*11:06, A*11:10, A*11:12, A*11:13, A*11:19, A*11:20, A*23:01:01, A*23:01:02, A*23:01:03, A*23:01:04, A*23:01:05, A*23:01:06, A*23:01:07, A*23:02, A*23:05, A*23:09, A*24:02:01:01, A*24:02:01:03, A*24:02:02, A*24:02:04, A*24:02:05, A*24:02:06, A*24:02:07, A*24:02:08, A*24:02:09, A*24:02:10, A*24:02:11, A*24:02:12, A*24:02:13, A*24:02:14, A*24:02:15, A*24:02:16, A*24:02:17, A*24:02:18, A*24:02:19, A*24:02:20, A*24:02:21, A*24:02:22, A*24:02:23, A*24:02:24, A*24:02:25, A*24:02:26, A*24:02:27, A*24:02:28, A*24:02:29, A*24:02:30, A*24:02:31, A*24:02:32, A*24:02:33, A*24:02:34, A*24:02:35, A*24:02:36, A*24:02:37, A*24:02:38, A*24:02:39, A*24:02:40, A*24:02:41, A*24:02:42, A*24:02:43, A*24:02:44, A*24:02:45, A*24:02:46, A*24:02:47, A*24:02:48, A*24:02:49, A*24:02:50, A*24:02:51, A*24:03:01, A*24:03:02, A*24:04, A*24:05, A*24:06, A*24:07, A*24:08, A*24:10, A*24:13:01, A*24:13:02, A*24:14, A*24:17, A*24:18, A*24:20, A*24:21:01, A*24:21:02, A*24:22, A*24:23, A*24:25, A*24:26, A*24:28, A*24:29, A*24:31, A*24:35, A*24:46, A*24:51, A*24:58, A*25:01:01, A*25:01:02, A*25:01:03, A*25:01:04, A*25:01:05, A*25:02, A*26:01:01, A*26:01:02, A*26:01:03, A*26:01:04, A*26:01:05, A*26:01:06, A*26:01:07, A*26:01:08, A*26:01:09, A*26:01:10, A*26:01:11, A*26:01:12, A*26:01:13, A*26:01:14, A*26:01:15, A*26:01:16, A*26:01:17, A*26:01:18, A*26:01:19, A*26:01:20, A*26:01:21, A*26:01:22, A*26:02, A*26:03:01, A*26:03:02, A*26:05, A*26:07:01, A*26:07:02, A*26:08, A*26:09, A*26:10, A*26:12, A*26:16, A*26:18, A*29:01:01, A*29:01:02, A*29:01:03, A*29:02:01:01, A*29:02:01:02, A*29:02:02, A*29:02:03, A*29:02:04, A*29:02:05, A*29:02:06, A*29:02:07, A*29:02:08, A*29:02:09, A*30:01:01, A*30:01:02, A*30:01:03, A*30:01:04, A*30:01:05, A*30:02:01, A*30:02:02, A*30:02:03, A*30:02:04, A*30:02:05, A*30:03, A*30:04:01, A*30:04:02, A*30:06, A*30:08, A*30:09, A*30:10, A*30:11:01, A*30:11:02, A*30:12, A*31:01:02, A*31:01:03, A*31:01:04, A*31:01:05, A*31:01:06, A*31:01:07, A*31:01:08, A*31:01:09, A*31:01:10, A*31:02, A*31:03, A*31:04, A*31:06, A*31:08, A*31:09, A*31:12, A*32:01:01, A*32:01:02, A*32:01:03, A*32:01:04, A*32:01:05, A*32:01:06, A*32:01:07, A*32:01:08, A*32:01:09, A*32:01:10, A*32:01:11, A*32:02, A*32:03, A*32:05, A*32:06, A*33:01:01, A*33:01:02, A*33:01:03, A*33:01:04, A*33:01:05, A*33:01:06, A*33:03:01, A*33:03:02, A*33:03:04, A*33:03:05, A*33:03:06, A*33:03:07, A*33:03:08, A*33:05, A*34:01:01, A*34:01:02, A*34:02:01, A*34:02:02, A*34:03, A*34:05, A*36:01, A*36:03, A*43:01, A*66:01, A*66:02, A*66:03, A*68:01:01:01, A*68:01:01:02, A*68:01:02, A*68:01:03, A*68:01:04, A*68:01:05, A*68:01:06, A*68:01:07, A*68:01:08, A*68:01:09, A*68:01:10, A*68:02:01:01, A*68:02:01:02, A*68:02:01:03, A*68:02:02, A*68:02:03, A*68:02:04, A*68:03:01, A*68:03:02, A*68:03:03, A*68:04, A*68:05, A*68:07, A*68:13, A*68:15, A*68:16, A*68:17, A*68:23, A*68:25, A*69:01, A*74:01, A*74:03, A*74:04, A*74:09, A*74:11, A*80:01, B*07:02:01, B*07:02:02, B*07:02:03, B*07:02:04, B*07:02:05, B*07:02:06, B*07:02:07, B*07:02:08, B*07:02:09, B*07:02:10, B*07:02:11, B*07:02:12, B*07:02:13, B*07:02:14, B*07:02:15, B*07:02:16, B*07:02:17, B*07:02:18, B*07:02:19, B*07:02:20, B*07:02:21, B*07:02:22, B*07:02:23, B*07:02:24, B*07:02:25, B*07:02:26, B*07:02:27, B*07:02:28, B*07:04, B*07:05:01, B*07:05:02, B*07:05:03, B*07:05:04, B*07:05:05, B*07:05:06, B*07:06, B*07:07, B*07:09, B*07:10, B*07:13, B*07:14, B*07:15, B*07:20, B*07:21, B*07:22:01, B*07:22:02, B*07:33, B*07:36, B*08:01:01, B*08:01:02, B*08:01:03, B*08:01:04, B*08:01:05, B*08:01:06, B*08:01:07, B*08:01:08, B*08:01:09, B*08:01:10, B*08:01:11, B*08:01:12, B*08:01:13, B*08:01:14, B*08:01:15, B*08:01:16, B*08:02, B*08:03, B*08:04, B*08:05, B*08:12:01, B*08:12:02, B*08:12:03, B*13:01:01, B*13:01:02, B*13:01:03, B*13:01:04, B*13:01:05, B*13:01:06, B*13:02:01, B*13:02:02, B*13:02:03, B*13:02:04, B*13:02:05, B*13:02:06, B*13:02:07, B*13:02:08, B*13:02:09, B*13:02:10, B*13:02:11, B*13:02:12, B*13:03, B*13:04, B*13:09, B*13:11, B*13:13, B*14:01:01, B*14:01:02, B*14:02:01, B*14:02:02, B*14:02:03, B*14:02:04, B*14:02:05, B*14:02:06, B*14:03, B*14:05, B*14:06:01, B*14:06:02, B*15:01:01:01, B*15:01:02, B*15:01:03, B*15:01:04, B*15:01:06, B*15:01:07, B*15:01:08, B*15:01:09, B*15:01:10, B*15:01:11, B*15:01:12, B*15:01:13, B*15:01:14, B*15:01:15, B*15:01:16, B*15:01:17, B*15:01:18, B*15:01:19, B*15:01:20, B*15:01:21, B*15:01:22, B*15:01:23, B*15:01:24, B*15:02:01, B*15:02:02, B*15:02:03, B*15:02:04, B*15:02:05, B*15:03:01, B*15:03:02, B*15:03:03, B*15:04, B*15:05:01, B*15:05:02, B*15:06, B*15:07:01, B*15:07:02, B*15:08, B*15:09, B*15:10:01, B*15:10:02, B*15:11:01, B*15:11:02, B*15:11:03, B*15:11:04, B*15:11:05, B*15:12, B*15:13:01, B*15:13:02, B*15:14, B*15:15, B*15:16:01, B*15:16:02, B*15:16:03, B*15:17:01:01, B*15:17:01:02, B*15:17:02, B*15:18:01, B*15:18:02, B*15:18:03, B*15:18:04, B*15:20, B*15:21, B*15:23, B*15:24, B*15:25:01, B*15:25:02, B*15:25:03, B*15:27:01, B*15:27:02, B*15:27:03, B*15:29, B*15:30, B*15:31, B*15:32, B*15:34, B*15:35, B*15:37, B*15:38:01, B*15:38:02, B*15:39:01, B*15:39:02, B*15:40, B*15:45, B*15:46, B*15:47, B*15:48, B*15:50, B*15:52, B*15:53, B*15:54, B*15:56, B*15:58, B*15:61, B*15:63, B*15:70, B*15:71, B*15:86, B*18:01:01, B*18:01:02, B*18:01:03, B*18:01:04, B*18:01:05, B*18:01:06, B*18:01:07, B*18:01:08, B*18:01:09, B*18:01:10, B*18:01:11, B*18:01:12, B*18:01:13, B*18:01:14, B*18:02, B*18:03, B*18:04, B*18:06, B*18:07:01, B*18:07:02, B*18:08, B*27:01, B*27:02:01, B*27:02:02, B*27:03, B*27:04:01, B*27:04:02, B*27:04:03, B*27:05:02, B*27:05:03, B*27:05:04, B*27:05:05, B*27:05:06, B*27:05:07, B*27:05:08, B*27:05:09, B*27:05:10, B*27:05:11, B*27:05:12, B*27:05:13, B*27:05:14, B*27:05:15, B*27:05:16, B*27:05:17, B*27:06, B*27:07, B*27:08, B*27:09, B*27:10, B*27:11, B*27:12, B*27:13, B*27:14, B*27:20, B*27:21, B*35:01:01:01, B*35:01:01:02, B*35:01:02, B*35:01:03, B*35:01:04, B*35:01:05, B*35:01:06, B*35:01:07, B*35:01:08, B*35:01:09, B*35:01:10, B*35:01:11, B*35:01:12, B*35:01:13, B*35:01:14, B*35:01:15, B*35:01:16, B*35:01:17, B*35:01:18, B*35:01:19, B*35:01:20, B*35:01:21, B*35:01:22, B*35:01:23, B*35:01:24, B*35:01:25, B*35:01:26, B*35:01:27, B*35:01:28, B*35:01:29, B*35:02:01, B*35:02:02, B*35:02:03, B*35:02:04, B*35:03:01, B*35:03:02, B*35:03:03, B*35:03:04, B*35:03:05, B*35:03:06, B*35:03:07, B*35:03:08, B*35:03:09, B*35:03:10, B*35:04:01, B*35:04:02, B*35:04:03, B*35:05:01, B*35:05:02, B*35:06, B*35:08:01, B*35:08:02, B*35:08:03, B*35:08:04, B*35:09:01, B*35:09:02, B*35:10, B*35:11:01, B*35:11:02, B*35:12:01, B*35:12:02, B*35:12:03, B*35:13, B*35:14:01, B*35:14:02, B*35:15, B*35:16, B*35:17, B*35:18, B*35:19, B*35:20:01, B*35:20:02, B*35:21, B*35:22, B*35:23, B*35:27, B*35:28, B*35:30, B*35:32, B*35:33, B*35:43:01, B*35:43:02, B*35:46, B*37:01:01, B*37:01:02, B*37:01:03, B*37:01:04, B*37:01:05, B*37:01:06, B*37:01:07, B*37:01:08, B*37:01:09, B*38:01:01, B*38:01:02, B*38:01:03, B*38:01:04, B*38:01:05, B*38:02:01, B*38:02:02, B*38:02:03, B*38:04, B*38:05, B*38:06, B*38:09, B*39:01:01:01, B*39:01:03, B*39:01:04, B*39:01:05, B*39:01:06, B*39:01:07, B*39:01:08, B*39:01:09, B*39:01:10, B*39:01:11, B*39:01:12, B*39:02:01, B*39:02:02, B*39:03, B*39:04, B*39:05:01, B*39:05:02, B*39:06:01, B*39:06:02, B*39:07, B*39:08, B*39:09, B*39:10:01, B*39:10:02, B*39:11, B*39:12, B*39:13:01, B*39:13:02, B*39:14, B*39:15, B*39:24:01, B*39:24:02, B*40:01:01, B*40:01:02, B*40:01:03, B*40:01:04, B*40:01:05, B*40:01:06, B*40:01:07, B*40:01:08, B*40:01:09, B*40:01:10, B*40:01:11, B*40:01:12, B*40:01:13, B*40:01:14, B*40:01:15, B*40:01:16, B*40:01:17, B*40:01:18, B*40:01:19, B*40:01:20, B*40:01:21, B*40:01:22, B*40:01:23, B*40:02:01, B*40:02:02, B*40:02:03, B*40:02:04, B*40:02:05, B*40:02:06, B*40:02:07, B*40:02:08, B*40:02:09, B*40:02:10, B*40:02:11, B*40:02:12, B*40:03, B*40:04, B*40:05, B*40:06:01:01, B*40:06:01:02, B*40:06:02, B*40:06:03, B*40:06:04, B*40:07, B*40:08, B*40:09, B*40:10:01, B*40:10:02, B*40:11:01, B*40:11:02, B*40:12, B*40:14:01, B*40:14:02, B*40:14:03, B*40:16, B*40:18, B*40:20, B*40:21, B*40:23, B*40:27:01, B*40:27:02, B*40:31, B*40:35, B*40:36, B*40:37, B*40:38, B*40:39, B*40:40, B*40:42, B*40:44, B*40:49, B*40:50, B*40:52, B*41:01, B*41:02:01, B*41:02:02, B*41:02:03, B*41:02:04, B*41:03:01, B*41:03:02, B*42:01:01, B*42:01:02, B*42:02, B*44:02:01:01, B*44:02:02, B*44:02:03, B*44:02:04, B*44:02:05, B*44:02:06, B*44:02:07, B*44:02:08, B*44:02:09, B*44:02:10, B*44:02:11, B*44:02:12, B*44:02:13, B*44:02:14, B*44:02:15, B*44:02:16, B*44:02:17, B*44:02:18, B*44:02:19, B*44:02:20, B*44:02:21, B*44:03:01, B*44:03:02, B*44:03:03, B*44:03:04, B*44:03:05, B*44:03:06, B*44:03:07, B*44:03:08, B*44:03:09, B*44:03:10, B*44:03:11, B*44:03:12, B*44:03:13, B*44:03:14, B*44:04, B*44:05:01, B*44:05:02, B*44:05:03, B*44:06, B*44:07, B*44:09, B*44:10, B*44:12, B*44:15, B*44:18, B*44:22, B*45:01, B*45:06, B*46:01:01, B*46:01:02, B*46:01:03, B*46:01:04, B*46:01:05, B*46:01:06, B*46:01:07, B*46:02, B*47:01:01:01, B*47:01:01:02, B*47:01:02, B*47:02, B*47:03, B*48:01:01, B*48:01:02, B*48:01:03, B*48:02:01, B*48:02:02, B*48:03:01, B*48:03:02, B*48:04, B*48:06, B*48:07, B*48:08, B*49:01:01, B*49:01:02, B*49:01:03, B*49:02, B*50:01:01, B*50:01:02, B*50:01:03, B*50:02, B*51:01:01, B*51:01:02, B*51:01:03, B*51:01:04, B*51:01:05, B*51:01:06, B*51:01:07, B*51:01:08, B*51:01:09, B*51:01:10, B*51:01:11, B*51:01:12, B*51:01:13, B*51:01:14, B*51:01:15, B*51:01:16, B*51:01:17, B*51:01:18, B*51:01:19, B*51:01:20, B*51:01:21, B*51:01:22, B*51:01:23, B*51:01:24, B*51:01:25, B*51:01:26, B*51:01:27, B*51:01:28, B*51:02:01, B*51:02:02, B*51:02:03, B*51:02:04, B*51:02:05, B*51:04, B*51:05, B*51:06:01, B*51:06:02, B*51:07:01, B*51:07:02, B*51:08, B*51:09:01, B*51:09:02, B*51:10, B*51:14, B*51:19, B*51:21, B*51:22, B*51:31, B*51:32, B*51:34, B*51:37, B*52:01:01:01, B*52:01:01:02, B*52:01:02, B*52:01:03, B*52:01:04, B*52:01:05, B*52:01:06, B*52:01:07, B*52:01:08, B*52:01:09, B*53:01:01, B*53:01:02, B*53:01:03, B*53:01:04, B*53:01:05, B*53:02, B*53:04, B*53:08:01, B*53:08:02, B*54:01:01, B*54:01:02, B*54:02, B*55:01:01, B*55:01:02, B*55:01:03, B*55:01:04, B*55:01:05, B*55:01:06, B*55:01:07, B*55:02:01, B*55:02:02, B*55:02:03, B*55:02:04, B*55:02:05, B*55:02:06, B*55:04, B*55:07, B*55:08, B*55:10, B*55:12, B*55:16, B*56:01:01, B*56:01:02, B*56:01:03, B*56:01:04, B*56:02, B*56:03, B*56:04, B*56:06, B*56:07, B*56:09, B*56:11, B*57:01:01, B*57:01:02, B*57:01:03, B*57:01:04, B*57:01:05, B*57:01:06, B*57:01:07, B*57:01:08, B*57:01:09, B*57:01:10, B*57:01:11, B*57:02:01, B*57:02:02, B*57:03:01, B*57:03:02, B*57:04, B*57:06, B*58:01:01, B*58:01:02, B*58:01:03, B*58:01:04, B*58:01:05, B*58:01:06, B*58:01:07, B*58:01:08, B*58:01:09, B*58:02, B*58:06, B*59:01:01:01, B*59:01:01:02, B*67:01:01, B*67:01:02, B*67:02, B*73:01, B*78:01:01, B*78:01:02, B*78:02:01, B*78:02:02, B*81:01, B*82:01, B*82:02, B*83:01, C*01:02:01, C*01:02:02, C*01:02:03, C*01:02:04, C*01:02:05, C*01:02:06, C*01:02:07, C*01:02:08, C*01:02:09, C*01:02:10, C*01:02:11, C*01:02:12, C*01:02:13, C*01:02:14, C*01:03, C*01:04, C*01:05, C*01:06, C*01:07, C*01:08, C*01:10, C*01:16, C*01:18, C*01:30, C*02:02:01, C*02:02:02, C*02:02:03, C*02:02:05, C*02:02:06, C*02:02:07, C*02:02:08, C*02:02:09, C*02:02:10, C*02:02:11, C*02:02:12, C*02:02:13, C*02:02:14, C*02:02:15, C*02:02:16, C*02:02:17, C*02:02:18, C*02:02:19, C*02:02:20, C*02:03, C*02:14, C*02:18, C*03:02:01, C*03:02:02:01, C*03:02:02:02, C*03:02:03, C*03:02:04, C*03:02:05, C*03:02:06, C*03:02:07, C*03:02:08, C*03:03:01, C*03:03:02, C*03:03:03, C*03:03:04, C*03:03:05, C*03:03:06, C*03:03:07, C*03:03:08, C*03:03:09, C*03:03:10, C*03:03:11, C*03:03:12, C*03:03:13, C*03:03:14, C*03:03:15, C*03:03:16, C*03:04:01:01, C*03:04:01:02, C*03:04:02, C*03:04:03, C*03:04:04, C*03:04:05, C*03:04:06, C*03:04:07, C*03:04:08, C*03:04:09, C*03:04:10, C*03:04:11, C*03:04:12, C*03:04:13, C*03:04:14, C*03:04:15, C*03:04:16, C*03:04:17, C*03:04:18, C*03:04:19, C*03:04:20, C*03:04:21, C*03:04:22, C*03:04:23, C*03:05, C*03:06, C*03:07, C*03:08, C*03:09, C*03:12, C*03:13, C*03:15, C*03:16, C*03:17, C*03:19, C*03:36, C*03:37, C*03:38:01, C*03:38:02, C*04:01:01:01, C*04:01:01:02, C*04:01:01:03, C*04:01:01:04, C*04:01:02, C*04:01:03, C*04:01:04, C*04:01:05, C*04:01:06, C*04:01:07, C*04:01:08, C*04:01:09, C*04:01:10, C*04:01:11, C*04:01:12, C*04:01:13, C*04:01:14, C*04:01:15, C*04:01:16, C*04:01:17, C*04:01:18, C*04:01:19, C*04:01:20, C*04:01:21, C*04:01:22, C*04:01:23, C*04:01:24, C*04:01:25, C*04:01:26, C*04:01:27, C*04:01:28, C*04:01:29, C*04:01:30, C*04:01:31, C*04:01:32, C*04:01:33, C*04:03, C*04:04:01, C*04:04:02, C*04:05, C*04:06, C*04:07, C*04:08, C*04:10, C*04:13, C*04:14, C*04:15:01, C*04:15:02, C*04:15:03, C*04:27, C*05:01:01:01, C*05:01:01:02, C*05:01:02, C*05:01:03, C*05:01:04, C*05:01:05, C*05:01:06, C*05:01:07, C*05:01:08, C*05:01:09, C*05:01:10, C*05:01:11, C*05:01:12, C*05:01:13, C*05:01:14, C*05:01:15, C*05:01:16, C*05:01:17, C*05:05, C*05:09, C*06:02:01:01, C*06:02:01:02, C*06:02:03, C*06:02:04, C*06:02:05, C*06:02:06, C*06:02:07, C*06:02:08, C*06:02:09, C*06:02:10, C*06:02:11, C*06:02:12, C*06:02:13, C*06:02:14, C*06:02:15, C*06:02:16, C*06:02:17, C*06:03, C*06:04, C*06:06, C*06:08, C*06:09, C*06:10, C*06:15, C*06:24, C*07:01:01, C*07:01:02, C*07:01:03, C*07:01:04, C*07:01:05, C*07:01:06, C*07:01:07, C*07:01:08, C*07:01:09, C*07:01:10, C*07:01:11, C*07:01:12, C*07:01:13, C*07:01:14, C*07:01:15, C*07:01:16, C*07:01:17, C*07:01:18, C*07:01:19, C*07:01:20, C*07:01:21, C*07:01:22, C*07:01:23, C*07:01:24, C*07:02:01:01, C*07:02:01:03, C*07:02:02, C*07:02:03, C*07:02:04, C*07:02:05, C*07:02:06, C*07:02:07, C*07:02:08, C*07:02:09, C*07:02:10, C*07:02:11, C*07:02:12, C*07:02:13, C*07:02:14, C*07:02:15, C*07:02:16, C*07:02:17, C*07:02:18, C*07:02:19, C*07:02:20, C*07:02:21, C*07:02:22, C*07:02:23, C*07:02:24, C*07:02:25, C*07:02:26, C*07:02:27, C*07:02:28, C*07:02:29, C*07:03, C*07:04:01, C*07:04:02, C*07:04:03, C*07:04:04, C*07:04:05, C*07:04:06, C*07:04:06, C*07:05, C*07:06, C*07:07, C*07:08, C*07:09, C*07:10, C*07:12, C*07:13, C*07:14, C*07:17, C*07:18, C*07:26, C*07:27:01, C*07:27:02, C*07:29, C*07:35, C*07:43, C*07:56:01, C*07:56:02, C*07:66, C*07:67, C*08:01:01, C*08:01:02, C*08:01:03, C*08:01:04, C*08:01:05, C*08:02:01, C*08:02:02, C*08:02:03, C*08:02:04, C*08:02:05, C*08:02:06, C*08:03:01, C*08:03:02, C*08:04, C*08:05, C*08:06, C*08:11, C*08:12, C*08:13, C*08:20, C*08:21, C*08:27, C*12:02:01, C*12:02:02, C*12:02:03, C*12:02:04, C*12:02:05, C*12:02:06, C*12:03:01:01, C*12:03:01:02, C*12:03:02, C*12:03:03, C*12:03:04, C*12:03:05, C*12:03:06, C*12:03:07, C*12:03:08, C*12:03:09, C*12:03:10, C*12:03:11, C*12:03:12, C*12:03:13, C*12:03:14, C*12:03:15, C*12:03:16, C*12:03:17, C*12:04:01, C*12:04:02, C*12:05, C*12:07, C*12:12, C*14:02:01, C*14:02:02, C*14:02:03, C*14:02:04, C*14:02:05, C*14:02:06, C*14:02:07, C*14:03, C*14:04, C*14:06, C*15:02:01, C*15:02:02, C*15:02:03, C*15:02:04, C*15:02:05, C*15:02:06, C*15:02:07, C*15:03, C*15:04, C*15:05:01, C*15:05:02, C*15:05:03, C*15:05:04, C*15:05:05, C*15:05:06, C*15:06:01, C*15:06:02, C*15:06:03, C*15:07, C*15:08, C*15:09, C*15:11, C*15:13, C*15:17, C*15:19, C*15:20, C*16:01:01, C*16:01:02, C*16:01:03, C*16:01:04, C*16:01:05, C*16:01:06, C*16:02:01, C*16:02:02, C*16:02:03, C*16:02:04, C*16:02:05, C*16:02:06, C*16:02:07, C*16:02:08, C*16:04:01, C*16:08, C*17:01:01:01, C*17:01:01:02, C*17:01:02, C*17:01:03, C*17:01:04, C*17:01:05, C*17:01:06, C*17:03, C*17:04, C*18:01, C*18:03, E*01:01:01:01, E*01:01:01:02, E*01:01:01:03, E*01:03:01:01, E*01:03:01:02, E*01:03:02:01, E*01:03:02:02, E*01:03:03, E*01:03:04, E*01:04, F*01:01:01:01, F*01:01:01:02, F*01:01:01:03, F*01:01:01:04, F*01:01:01:05, F*01:01:01:06, F*01:01:01:07, F*01:01:01:08, F*01:01:02:01, F*01:01:02:02, F*01:01:02:03, F*01:01:02:04, F*01:01:02:05, F*01:01:02:06, F*01:01:03:01, F*01:01:03:02, F*01:01:03:03, F*01:01:03:04, F*01:02, F*01:03:01:01, F*01:03:01:02, F*01:04, G*01:01:01:01, G*01:01:01:02, G*01:01:01:03, G*01:01:01:04, G*01:01:01:05, G*01:01:01:06, G*01:01:02:01, G*01:01:02:02, G*01:01:03:01, G*01:01:03:02, G*01:01:04, G*01:01:05, G*01:01:06, G*01:01:07, G*01:01:08, G*01:01:09, G*01:01:11, G*01:01:12, G*01:01:13, G*01:01:14, G*01:01:15, G*01:01:16, G*01:01:17, G*01:01:18, G*01:01:19, G*01:01:20, G*01:02, G*01:03:01:01, G*01:03:01:02, G*01:04:01, G*01:04:02, G*01:04:03, G*01:04:04, G*01:04:05, G*01:06, G*01:07, G*01:08, G*01:09, G*01:10, G*01:11, G*01:12, G*01:14, G*01:15, G*01:16, G*01:17, DPA1*01:03:01:01, DPA1*01:03:01:02, DPA1*01:03:01:03, DPA1*01:03:01:04, DPA1*01:03:01:05, DPA1*01:03:02, DPA1*01:03:03, DPA1*01:03:04, DPA1*01:04, DPA1*01:05, DPA1*01:06:01, DPA1*01:06:02, DPA1*01:07, DPA1*01:08, DPA1*01:09, DPA1*01:10, DPA1*02:01:01, DPA1*02:01:02, DPA1*02:01:03, DPA1*02:01:04, DPA1*02:01:05, DPA1*02:01:06, DPA1*02:01:07, DPA1*02:02:01, DPA1*02:02:02, DPA1*02:02:03, DPA1*02:03, DPA1*02:04, DPA1*03:01, DPA1*03:02, DPA1*03:03, DPA1*04:01, DPB1*01:01:01, DPB1*01:01:02, DPB1*01:01:03, DPB1*02:01:02, DPB1*02:01:03, DPB1*02:01:04, DPB1*02:01:05, DPB1*02:01:06, DPB1*02:01:07, DPB1*02:02, DPB1*03:01:01, DPB1*03:01:02, DPB1*04:01:01:01, DPB1*04:01:01:02, DPB1*04:01:02, DPB1*04:02:01:01, DPB1*04:02:01:02, DPB1*05:01:01, DPB1*05:01:02, DPB1*06:01:01, DPB1*08:01, DPB1*09:01, DPB1*100:01, DPB1*101:01, DPB1*102:01, DPB1*103:01, DPB1*104:01, DPB1*105:

01, DPB1*106:01, DPB1*107:01, DPB1*108:01, DPB1*109:01, DPB1*10:01, DPB1*110:01, DPB1*111:01, DPB1*112:01, DPB1*113:01, DPB1*114:01, DPB1*115:01, DPB1*116:01, DPB1*117:01, DPB1*118:01, DPB1*119:01, DPB1*11:01:01, DPB1*11:01:02, DPB1*121:01, DPB1*122:01, DPB1*123:01, DPB1*124:01, DPB1*125:01, DPB1*126:01, DPB1*127:01, DPB1*128:01, DPB1*129:01, DPB1*130:01, DPB1*131:01, DPB1*132:01, DPB1*133:01, DPB1*134:01, DPB1*13:01, DPB1*14:01, DPB1*15:01, DPB1*16:01, DPB1*17:01, DPB1*18:01, DPB1*19:01, DPB1*20:01:01, DPB1*20:01:02, DPB1*21:01, DPB1*22:01, DPB1*23:01, DPB1*24:01, DPB1*25:01, DPB1*26:01:01, DPB1*26:01:02, DPB1*27:01, DPB1*28:01, DPB1*29:01, DPB1*30:01, DPB1*31:01, DPB1*32:01, DPB1*33:01, DPB1*34:01, DPB1*35:01:01, DPB1*35:01:02, DPB1*36:01, DPB1*37:01, DPB1*38:01, DPB1*39:01, DPB1*40:01, DPB1*41:01:01, DPB1*41:01:02, DPB1*44:01, DPB1*45:01, DPB1*46:01, DPB1*47:01, DPB1*48:01, DPB1*49:01, DPB1*50:01, DPB1*51:01, DPB1*52:01, DPB1*53:01, DPB1*54:01, DPB1*55:01, DPB1*56:01, DPB1*57:01, DPB1*58:01, DPB1*59:01, DPB1*60:01, DPB1*62:01, DPB1*63:01, DPB1*65:01, DPB1*66:01, DPB1*67:01, DPB1*68:01, DPB1*69:01, DPB1*70:01, DPB1*71:01, DPB1*72:01, DPB1*73:01, DPB1*74:01, DPB1*75:01, DPB1*76:01, DPB1*77:01, DPB1*78:01, DPB1*79:01, DPB1*80:01, DPB1*81:01, DPB1*82:01, DPB1*83:01, DPB1*84:01, DPB1*85:01, DPB1*86:01, DPB1*87:01, DPB1*88:01, DPB1*89:01, DPB1*90:01, DPB1*91:01, DPB1*92:01, DPB1*93:01, DPB1*94:01, DPB1*95:01, DPB1*96:01, DPB1*97:01, DPB1*98:01, DPB1*99:01, DQA1*01:01:01, DQA1*01:01:02, DQA1*01:02:01:01, DQA1*01:02:01:02, DQA1*01:02:01:03, DQA1*01:02:01:04, DQA1*01:02:02, DQA1*01:02:03, DQA1*01:02:04, DQA1*01:03:01:01, DQA1*01:03:01:02, DQA1*01:04:01:01, DQA1*01:04:01:02, DQA1*01:04:02, DQA1*01:05, DQA1*01:06, DQA1*01:07, DQA1*02:01, DQA1*03:01:01, DQA1*03:02, DQA1*03:03, DQA1*04:01:01, DQA1*04:01:02, DQA1*04:02, DQA1*04:04, DQA1*05:01:01:01, DQA1*05:01:01:02, DQA1*05:01:02, DQA1*05:02, DQA1*05:03, DQA1*05:04, DQA1*05:05:01:01, DQA1*05:05:01:02, DQA1*05:05:01:03, DQA1*05:06, DQA1*05:07, DQA1*05:08, DQA1*05:09, DQA1*05:10, DQA1*05:11, DQA1*06:01:01, DQA1*06:01:02, DQB1*02:01:01, DQB1*02:01:02, DQB1*02:01:03, DQB1*02:01:04, DQB1*02:02, DQB1*02:03, DQB1*02:04, DQB1*02:05, DQB1*02:06, DQB1*03:01:01:01, DQB1*03:01:01:02, DQB1*03:01:01:03, DQB1*03:01:02, DQB1*03:01:03, DQB1*03:01:04, DQB1*03:01:05, DQB1*03:01:06, DQB1*03:02:01, DQB1*03:02:02, DQB1*03:02:03, DQB1*03:02:04, DQB1*03:02:05, DQB1*03:03:02:01, DQB1*03:03:02:02, DQB1*03:03:02:03, DQB1*03:03:03, DQB1*03:03:04, DQB1*03:04, DQB1*03:05:01, DQB1*03:05:02, DQB1*03:05:03, DQB1*03:05:04, DQB1*03:06, DQB1*03:07, DQB1*03:08, DQB1*03:09, DQB1*03:10, DQB1*03:11, DQB1*03:12, DQB1*03:13, DQB1*03:14, DQB1*03:15, DQB1*03:16, DQB1*03:17, DQB1*03:18, DQB1*03:19, DQB1*03:20, DQB1*03:21, DQB1*03:22, DQB1*03:23, DQB1*03:24, DQB1*03:25, DQB1*03:26, DQB1*03:27, DQB1*03:28, DQB1*03:29, DQB1*03:30, DQB1*03:31, DQB1*03:32, DQB1*03:33, DQB1*03:34, DQB1*03:35, DQB1*03:36, DQB1*03:37, DQB1*03:38, DQB1*04:01:01, DQB1*04:01:02, DQB1*04:02:01, DQB1*04:02:02, DQB1*04:03:01, DQB1*04:03:02, DQB1*04:04, DQB1*04:05, DQB1*04:06, DQB1*04:07, DQB1*04:08, DQB1*05:01:01:01, DQB1*05:01:01:02, DQB1*05:01:02, DQB1*05:01:03, DQB1*05:02:01, DQB1*05:02:02, DQB1*05:02:03, DQB1*05:03:01:01, DQB1*05:03:01:02, DQB1*05:03:02, DQB1*05:03:03, DQB1*05:03:04, DQB1*05:03:05, DQB1*05:04, DQB1*05:05, DQB1*05:06, DQB1*05:07, DQB1*05:08, DQB1*05:09, DQB1*05:10, DQB1*05:11, DQB1*05:12, DQB1*06:01:01, DQB1*06:01:02, DQB1*06:01:03, DQB1*06:01:04, DQB1*06:01:05, DQB1*06:01:06, DQB1*06:02:01, DQB1*06:02:02, DQB1*06:03:01, DQB1*06:03:02, DQB1*06:04:01, DQB1*06:04:02, DQB1*06:04:03, DQB1*06:05:01, DQB1*06:05:02, DQB1*06:06, DQB1*06:07:01, DQB1*06:07:02, DQB1*06:08:01, DQB1*06:08:02, DQB1*06:09, DQB1*06:10, DQB1*06:11:01, DQB1*06:11:02, DQB1*06:12, DQB1*06:13, DQB1*06:14:01, DQB1*06:14:02, DQB1*06:15, DQB1*06:16, DQB1*06:17, DQB1*06:18, DQB1*06:19, DQB1*06:20, DQB1*06:21, DQB1*06:22, DQB1*06:23, DQB1*06:24, DQB1*06:25, DQB1*06:27, DQB1*06:28, DQB1*06:29, DQB1*06:30, DQB1*06:31, DQB1*06:32, DQB1*06:33, DQB1*06:34, DQB1*06:35, DQB1*06:36, DQB1*06:37, DQB1*06:38, DQB1*06:39, DQB1*06:40, DQB1*06:41, DQB1*06:42, DQB1*06:43, DQB1*06:44, DRA*01:01:01:01, DRA*01:01:01:02, DRA*01:01:01:03, DRA*01:01:02, DRA*01:02:01, DRA*01:02:02, DRA*01:02:03, DRB1*01:01:01, DRB1*01:01:02, DRB1*01:01:03, DRB1*01:01:04, DRB1*01:01:05, DRB1*01:01:06, DRB1*01:01:07, DRB1*01:01:08, DRB1*01:01:09, DRB1*01:01:10, DRB1*01:01:11, DRB1*01:01:12, DRB1*01:01:13, DRB1*01:01:14, DRB1*01:01:15, DRB1*01:01:16, DRB1*01:01:17, DRB1*01:01:18, DRB1*01:01:19, DRB1*01:01:20, DRB1*01:02:01, DRB1*01:02:02, DRB1*01:02:03, DRB1*01:02:04, DRB1*01:02:05, DRB1*01:03, DRB1*01:04, DRB1*01:05, DRB1*01:06, DRB1*01:07, DRB1*01:08, DRB1*01:09, DRB1*01:10, DRB1*01:11, DRB1*01:12, DRB1*01:13, DRB1*01:14, DRB1*01:15, DRB1*01:16, DRB1*01:17, DRB1*01:18, DRB1*01:19, DRB1*01:20, DRB1*01:21, DRB1*01:22, DRB1*01:23, DRB1*01:24, DRB1*01:25, DRB1*01:26, DRB1*01:27, DRB1*01:28, DRB1*01:29, DRB1*01:30, DRB1*01:31, DRB1*01:32, DRB1*01:34, DRB1*01:35, DRB1*01:36, DRB1*01:37, DRB1*03:01:01:01, DRB1*03:01:01:02, DRB1*03:01:02, DRB1*03:01:03, DRB1*03:01:04, DRB1*03:01:05, DRB1*03:01:06, DRB1*03:01:07, DRB1*03:01:08, DRB1*03:01:09, DRB1*03:01:10, DRB1*03:01:11, DRB1*03:01:12, DRB1*03:01:13, DRB1*03:01:14, DRB1*03:02:01, DRB1*03:02:02, DRB1*03:03, DRB1*03:04:01, DRB1*03:04:02, DRB1*03:05:01, DRB1*03:05:02, DRB1*03:05:03, DRB1*03:06, DRB1*03:07, DRB1*03:08, DRB1*03:09, DRB1*03:10, DRB1*03:11:01, DRB1*03:11:02, DRB1*03:12, DRB1*03:13:01, DRB1*03:13:02, DRB1*03:14, DRB1*03:15, DRB1*03:16, DRB1*03:17, DRB1*03:18, DRB1*03:19, DRB1*03:20, DRB1*03:21, DRB1*03:22, DRB1*03:23, DRB1*03:24, DRB1*03:25, DRB1*03:26, DRB1*03:27, DRB1*03:28, DRB1*03:29, DRB1*03:30, DRB1*03:31, DRB1*03:32, DRB1*03:33, DRB1*03:34, DRB1*03:35, DRB1*03:36, DRB1*03:37, DRB1*03:38, DRB1*03:39, DRB1*03:40, DRB1*03:41, DRB1*03:42, DRB1*03:43, DRB1*03:44, DRB1*03:45, DRB1*03:46, DRB1*03:47, DRB1*03:48, DRB1*03:49, DRB1*03:50, DRB1*03:51, DRB1*03:52, DRB1*03:53, DRB1*03:54, DRB1*03:55, DRB1*03:56, DRB1*03:57, DRB1*03:58, DRB1*03:59, DRB1*03:60, DRB1*03:61, DRB1*03:62, DRB1*03:63, DRB1*03:64, DRB1*03:65, DRB1*04:01:01, DRB1*04:01:02, DRB1*04:01:03, DRB1*04:01:04, DRB1*04:01:05, DRB1*04:01:06, DRB1*04:01:07, DRB1*04:02:01,

DRB1*04:02:02, DRB1*04:02:03, DRB1*04:03:01, DRB1*04:03:02, DRB1*04:03:03, DRB1*04:03:04, DRB1*04:03:05, DRB1*04:03:06, DRB1*04:03:07, DRB1*04:04:01, DRB1*04:04:02, DRB1*04:04:03, DRB1*04:04:04, DRB1*04:04:05, DRB1*04:04:06, DRB1*04:05:01, DRB1*04:05:02, DRB1*04:05:03, DRB1*04:05:04, DRB1*04:05:05, DRB1*04:05:06, DRB1*04:05:07, DRB1*04:05:08, DRB1*04:05:09, DRB1*04:05:10, DRB1*04:05:11, DRB1*04:05:12, DRB1*04:06:01, DRB1*04:06:02, DRB1*04:06:03, DRB1*04:06:04, DRB1*04:07:01, DRB1*04:07:02, DRB1*04:07:03, DRB1*04:07:04, DRB1*04:08:01, DRB1*04:08:02, DRB1*04:09, DRB1*04:10, DRB1*04:100, DRB1*04:101, DRB1*04:102, DRB1*04:11, DRB1*04:12, DRB1*04:13, DRB1*04:14, DRB1*04:15, DRB1*04:16, DRB1*04:17:01, DRB1*04:17:02, DRB1*04:18, DRB1*04:19, DRB1*04:20, DRB1*04:21, DRB1*04:22, DRB1*04:23, DRB1*04:24, DRB1*04:25, DRB1*04:26, DRB1*04:27, DRB1*04:28, DRB1*04:29, DRB1*04:30, DRB1*04:31, DRB1*04:32, DRB1*04:33, DRB1*04:34, DRB1*04:35, DRB1*04:36, DRB1*04:37, DRB1*04:38, DRB1*04:39, DRB1*04:40, DRB1*04:41, DRB1*04:42, DRB1*04:43, DRB1*04:44, DRB1*04:45, DRB1*04:46, DRB1*04:47, DRB1*04:48, DRB1*04:49, DRB1*04:50, DRB1*04:51, DRB1*04:52, DRB1*04:53, DRB1*04:54, DRB1*04:55, DRB1*04:56, DRB1*04:57, DRB1*04:58, DRB1*04:59, DRB1*04:60, DRB1*04:61, DRB1*04:62, DRB1*04:63, DRB1*04:64, DRB1*04:65, DRB1*04:66, DRB1*04:67, DRB1*04:68, DRB1*04:69, DRB1*04:70, DRB1*04:71, DRB1*04:72:01, DRB1*04:72:02, DRB1*04:73, DRB1*04:74, DRB1*04:75, DRB1*04:76, DRB1*04:77, DRB1*04:78, DRB1*04:79, DRB1*04:80, DRB1*04:82, DRB1*04:83, DRB1*04:84, DRB1*04:85, DRB1*04:86, DRB1*04:87, DRB1*04:88, DRB1*04:89, DRB1*04:90, DRB1*04:91, DRB1*04:92, DRB1*04:93, DRB1*04:95, DRB1*04:96, DRB1*04:97, DRB1*04:98, DRB1*04:99, DRB1*07:01:01:01, DRB1*07:01:01:02, DRB1*07:01:02, DRB1*07:01:03, DRB1*07:01:04, DRB1*07:03, DRB1*07:04, DRB1*07:05, DRB1*07:06, DRB1*07:07, DRB1*07:08, DRB1*07:09, DRB1*07:11, DRB1*07:12, DRB1*07:13, DRB1*07:14, DRB1*07:15, DRB1*07:16, DRB1*07:17, DRB1*07:18, DRB1*07:19, DRB1*07:20, DRB1*07:21, DRB1*08:01:01, DRB1*08:01:02, DRB1*08:01:03, DRB1*08:01:04, DRB1*08:01:05, DRB1*08:02:01, DRB1*08:02:02, DRB1*08:02:03, DRB1*08:02:04, DRB1*08:03:02, DRB1*08:04:01, DRB1*08:04:02, DRB1*08:04:03, DRB1*08:04:04, DRB1*08:04:05, DRB1*08:04:06, DRB1*08:04:07, DRB1*08:05, DRB1*08:06, DRB1*08:07, DRB1*08:08, DRB1*08:09, DRB1*08:10, DRB1*08:11, DRB1*08:12, DRB1*08:13, DRB1*08:14, DRB1*08:15, DRB1*08:16, DRB1*08:17, DRB1*08:18, DRB1*08:19, DRB1*08:20, DRB1*08:21, DRB1*08:22, DRB1*08:23, DRB1*08:24, DRB1*08:25, DRB1*08:26, DRB1*08:27, DRB1*08:28, DRB1*08:29, DRB1*08:30:01, DRB1*08:30:02, DRB1*08:30:03, DRB1*08:31, DRB1*08:32, DRB1*08:33, DRB1*08:34, DRB1*08:35, DRB1*08:36, DRB1*08:37, DRB1*08:38, DRB1*08:39, DRB1*08:40, DRB1*08:41, DRB1*08:42, DRB1*08:43, DRB1*08:44, DRB1*08:45, DRB1*08:46, DRB1*08:47, DRB1*08:48, DRB1*09:01:02, DRB1*09:01:03, DRB1*09:01:04, DRB1*09:01:05, DRB1*09:01:06, DRB1*09:01:07, DRB1*09:02:01, DRB1*09:02:02, DRB1*09:03, DRB1*09:04, DRB1*09:05, DRB1*09:06, DRB1*09:07, DRB1*09:08, DRB1*09:09, DRB1*09:10, DRB1*09:11, DRB1*09:12, DRB1*09:13, DRB1*09:14, DRB1*09:15, DRB1*09:16, DRB1*10:01:01, DRB1*10:01:02, DRB1*10:01:03, DRB1*10:02, DRB1*10:03, DRB1*11:01:01, DRB1*11:01:02, DRB1*11:01:03, DRB1*11:01:04, DRB1*11:01:05, DRB1*11:01:06, DRB1*11:01:07, DRB1*11:01:08, DRB1*11:01:09, DRB1*11:01:10, DRB1*11:01:11, DRB1*11:01:12, DRB1*11:01:13, DRB1*11:01:14, DRB1*11:01:15, DRB1*11:02:01, DRB1*11:02:02, DRB1*11:03, DRB1*11:04:01, DRB1*11:04:02, DRB1*11:04:03, DRB1*11:04:04, DRB1*11:04:05, DRB1*11:04:06, DRB1*11:04:07, DRB1*11:04:08, DRB1*11:05, DRB1*11:06:01, DRB1*11:06:02, DRB1*11:07, DRB1*11:08:01, DRB1*11:08:02, DRB1*11:09, DRB1*11:100, DRB1*11:101, DRB1*11:102, DRB1*11:103, DRB1*11:104, DRB1*11:105, DRB1*11:106, DRB1*11:107, DRB1*11:108, DRB1*11:109, DRB1*11:10:01, DRB1*11:10:02, DRB1*11:110, DRB1*11:111, DRB1*11:112, DRB1*11:113, DRB1*11:11:01, DRB1*11:11:02, DRB1*11:12:01, DRB1*11:12:02, DRB1*11:13:01, DRB1*11:13:02, DRB1*11:14:01, DRB1*11:14:02, DRB1*11:15, DRB1*11:16, DRB1*11:17, DRB1*11:18, DRB1*11:19:01, DRB1*11:19:02, DRB1*11:19:03, DRB1*11:20, DRB1*11:21, DRB1*11:22, DRB1*11:23, DRB1*11:24, DRB1*11:25, DRB1*11:26, DRB1*11:27:01, DRB1*11:27:02, DRB1*11:27:03, DRB1*11:28:01, DRB1*11:28:02, DRB1*11:29, DRB1*11:30, DRB1*11:31, DRB1*11:32, DRB1*11:33, DRB1*11:34, DRB1*11:35, DRB1*11:36, DRB1*11:37, DRB1*11:38, DRB1*11:39, DRB1*11:40, DRB1*11:41, DRB1*11:42, DRB1*11:43, DRB1*11:44, DRB1*11:45, DRB1*11:46:01, DRB1*11:46:02, DRB1*11:47, DRB1*11:48, DRB1*11:49:01, DRB1*11:49:02, DRB1*11:50, DRB1*11:51, DRB1*11:52, DRB1*11:53, DRB1*11:54:01, DRB1*11:54:02, DRB1*11:55, DRB1*11:56, DRB1*11:57, DRB1*11:58:01, DRB1*11:58:02, DRB1*11:59, DRB1*11:60, DRB1*11:61, DRB1*11:62, DRB1*11:63, DRB1*11:64, DRB1*11:65:01, DRB1*11:65:02, DRB1*11:66, DRB1*11:67, DRB1*11:68, DRB1*11:69, DRB1*11:70, DRB1*11:72, DRB1*11:73, DRB1*11:74:01, DRB1*11:74:02, DRB1*11:75, DRB1*11:76, DRB1*11:77, DRB1*11:78, DRB1*11:79, DRB1*11:80, DRB1*11:81, DRB1*11:82, DRB1*11:83, DRB1*11:84, DRB1*11:85, DRB1*11:86, DRB1*11:87, DRB1*11:88, DRB1*11:89, DRB1*11:90, DRB1*11:91, DRB1*11:92, DRB1*11:93, DRB1*11:94, DRB1*11:95, DRB1*11:96, DRB1*11:97, DRB1*11:98, DRB1*11:99, DRB1*12:01:01, DRB1*12:01:02, DRB1*12:01:03, DRB1*12:01:04, DRB1*12:02:01, DRB1*12:02:02, DRB1*12:02:03, DRB1*12:02:04, DRB1*12:02:05, DRB1*12:03:02, DRB1*12:04, DRB1*12:05, DRB1*12:06, DRB1*12:07, DRB1*12:08, DRB1*12:09, DRB1*12:10, DRB1*12:11, DRB1*12:12, DRB1*12:13, DRB1*12:14, DRB1*12:15, DRB1*12:16, DRB1*12:17, DRB1*12:18, DRB1*12:19, DRB1*12:20, DRB1*12:21, DRB1*12:22, DRB1*12:23, DRB1*12:25, DRB1*12:26, DRB1*12:27, DRB1*12:28, DRB1*12:29, DRB1*12:30, DRB1*12:32, DRB1*12:33, DRB1*12:34, DRB1*13:01:01, DRB1*13:01:02, DRB1*13:01:03, DRB1*13:01:04, DRB1*13:01:05, DRB1*13:01:06, DRB1*13:01:07, DRB1*13:01:08, DRB1*13:01:09, DRB1*13:02:01, DRB1*13:02:02, DRB1*13:02:03, DRB1*13:02:04, DRB1*13:02:05, DRB1*13:03:01, DRB1*13:03:02, DRB1*13:03:03, DRB1*13:03:04, DRB1*13:03:05, DRB1*13:03:06, DRB1*13:04, DRB1*13:05:01, DRB1*13:05:02, DRB1*13:06, DRB1*13:07:01, DRB1*13:07:02, DRB1*13:08, DRB1*13:09, DRB1*13:10, DRB1*13:100, DRB1*13:101, DRB1*13:102, DRB1*13:103, DRB1*13:104, DRB1*13:105, DRB1*13:106, DRB1*13:107,

DRB1*13:108, DRB1*13:109, DRB1*13:110, DRB1*13:111, DRB1*13:112, DRB1*13:114, DRB1*13:115, DRB1*13:116, DRB1*13:117, DRB1*13:118, DRB1*13:119, DRB1*13:11:01, DRB1*13:11:02, DRB1*13:12:01, DRB1*13:12:02, DRB1*13:13, DRB1*13:14:01, DRB1*13:14:02, DRB1*13:14:03, DRB1*13:15, DRB1*13:16, DRB1*13:17, DRB1*13:18, DRB1*13:19, DRB1*13:20, DRB1*13:21:01, DRB1*13:21:02, DRB1*13:22, DRB1*13:23:01, DRB1*13:23:02, DRB1*13:24, DRB1*13:25, DRB1*13:26, DRB1*13:27, DRB1*13:28, DRB1*13:29, DRB1*13:30, DRB1*13:31, DRB1*13:32, DRB1*13:33:01, DRB1*13:33:02, DRB1*13:33:03, DRB1*13:34, DRB1*13:35, DRB1*13:36, DRB1*13:37, DRB1*13:38, DRB1*13:39, DRB1*13:40, DRB1*13:41, DRB1*13:42, DRB1*13:43, DRB1*13:44, DRB1*13:45, DRB1*13:46, DRB1*13:47, DRB1*13:48, DRB1*13:49, DRB1*13:50:01, DRB1*13:50:02, DRB1*13:51, DRB1*13:52, DRB1*13:53, DRB1*13:54, DRB1*13:55, DRB1*13:56, DRB1*13:57, DRB1*13:58, DRB1*13:59, DRB1*13:60, DRB1*13:61:01, DRB1*13:61:02, DRB1*13:62, DRB1*13:63, DRB1*13:64, DRB1*13:65, DRB1*13:66:01, DRB1*13:66:02, DRB1*13:67, DRB1*13:68, DRB1*13:69, DRB1*13:70, DRB1*13:71, DRB1*13:72, DRB1*13:73, DRB1*13:74, DRB1*13:75, DRB1*13:76, DRB1*13:77, DRB1*13:78, DRB1*13:79, DRB1*13:80, DRB1*13:81, DRB1*13:82, DRB1*13:83, DRB1*13:84, DRB1*13:85, DRB1*13:86, DRB1*13:87, DRB1*13:88, DRB1*13:89, DRB1*13:90, DRB1*13:91, DRB1*13:92, DRB1*13:93, DRB1*13:94, DRB1*13:95, DRB1*13:96:01, DRB1*13:96:02, DRB1*13:97, DRB1*13:98, DRB1*13:99, DRB1*14:01:01, DRB1*14:01:02, DRB1*14:01:03, DRB1*14:02, DRB1*14:03:01, DRB1*14:03:02, DRB1*14:04, DRB1*14:05:01, DRB1*14:05:02, DRB1*14:05:03, DRB1*14:06:01, DRB1*14:06:02, DRB1*14:07:01, DRB1*14:07:02, DRB1*14:08, DRB1*14:09, DRB1*14:10, DRB1*14:100, DRB1*14:101, DRB1*14:102, DRB1*14:103, DRB1*14:104, DRB1*14:105, DRB1*14:106, DRB1*14:107, DRB1*14:108, DRB1*14:109, DRB1*14:11, DRB1*14:110, DRB1*14:111, DRB1*14:112, DRB1*14:113, DRB1*14:114, DRB1*14:115, DRB1*14:116, DRB1*14:117, DRB1*14:12:01, DRB1*14:12:02, DRB1*14:13, DRB1*14:14, DRB1*14:15, DRB1*14:16, DRB1*14:17, DRB1*14:18, DRB1*14:19, DRB1*14:20, DRB1*14:21, DRB1*14:22, DRB1*14:23:01, DRB1*14:23:02, DRB1*14:23:03, DRB1*14:24, DRB1*14:25, DRB1*14:26, DRB1*14:27, DRB1*14:28, DRB1*14:29, DRB1*14:30, DRB1*14:31, DRB1*14:32:01, DRB1*14:32:02, DRB1*14:33, DRB1*14:34, DRB1*14:35, DRB1*14:36, DRB1*14:37, DRB1*14:38, DRB1*14:39, DRB1*14:40, DRB1*14:41, DRB1*14:42, DRB1*14:43, DRB1*14:44:01, DRB1*14:44:02, DRB1*14:45, DRB1*14:46, DRB1*14:47, DRB1*14:48, DRB1*14:49, DRB1*14:50, DRB1*14:51, DRB1*14:52, DRB1*14:53, DRB1*14:54, DRB1*14:55, DRB1*14:56, DRB1*14:57, DRB1*14:58, DRB1*14:59, DRB1*14:60, DRB1*14:61, DRB1*14:62, DRB1*14:63, DRB1*14:64, DRB1*14:65, DRB1*14:67, DRB1*14:68, DRB1*14:69, DRB1*14:70, DRB1*14:71, DRB1*14:72, DRB1*14:73, DRB1*14:74, DRB1*14:75, DRB1*14:76, DRB1*14:77, DRB1*14:78, DRB1*14:79, DRB1*14:80, DRB1*14:81, DRB1*14:82, DRB1*14:83, DRB1*14:84, DRB1*14:85, DRB1*14:86, DRB1*14:87, DRB1*14:88, DRB1*14:89, DRB1*14:90, DRB1*14:91, DRB1*14:93, DRB1*14:94, DRB1*14:95, DRB1*14:96, DRB1*14:97, DRB1*14:98, DRB1*14:99, DRB1*15:01:01:01, DRB1*15:01:01:02, DRB1*15:01:02, DRB1*15:01:03, DRB1*15:01:04, DRB1*15:01:05, DRB1*15:01:06, DRB1*15:01:07, DRB1*15:01:08, DRB1*15:01:09, DRB1*15:01:10, DRB1*15:01:11, DRB1*15:01:12, DRB1*15:01:13, DRB1*15:01:14, DRB1*15:01:15, DRB1*15:01:16, DRB1*15:01:17, DRB1*15:02:01, DRB1*15:02:02, DRB1*15:02:03, DRB1*15:02:04, DRB1*15:02:05, DRB1*15:02:06, DRB1*15:02:07, DRB1*15:02:08, DRB1*15:03:01:01, DRB1*15:03:01:02, DRB1*15:03:02, DRB1*15:04, DRB1*15:05, DRB1*15:06, DRB1*15:07, DRB1*15:08, DRB1*15:09, DRB1*15:10, DRB1*15:11, DRB1*15:12, DRB1*15:13, DRB1*15:14, DRB1*15:15, DRB1*15:16, DRB1*15:18, DRB1*15:19, DRB1*15:20, DRB1*15:21, DRB1*15:22, DRB1*15:23, DRB1*15:24, DRB1*15:25, DRB1*15:26, DRB1*15:27, DRB1*15:28, DRB1*15:29, DRB1*15:30, DRB1*15:31, DRB1*15:32, DRB1*15:33, DRB1*15:34, DRB1*15:35, DRB1*15:36, DRB1*15:37, DRB1*15:38, DRB1*15:39, DRB1*15:40, DRB1*15:41, DRB1*15:42, DRB1*15:43, DRB1*15:44, DRB1*15:45, DRB1*15:46, DRB1*15:47, DRB1*15:48, DRB1*15:49, DRB1*15:51, DRB1*15:52, DRB1*15:53, DRB1*15:54, DRB1*15:55, DRB1*15:56, DRB1*15:57, DRB1*15:58, DRB1*16:01:01, DRB1*16:01:02, DRB1*16:02:01, DRB1*16:02:02, DRB1*16:03, DRB1*16:04, DRB1*16:05:01, DRB1*16:05:02, DRB1*16:07, DRB1*16:08, DRB1*16:09, DRB1*16:10, DRB1*16:11, DRB1*16:12, DRB1*16:14, DRB1*16:15, DRB1*16:16, DRB1*16:17, DRB1*16:18, DRB3*01:01:02:01, DRB3*01:01:02:02, DRB3*01:01:03, DRB3*01:01:04, DRB3*01:01:05, DRB3*01:02, DRB3*01:03, DRB3*01:04, DRB3*01:05, DRB3*01:06, DRB3*01:07, DRB3*01:08, DRB3*01:09, DRB3*01:10, DRB3*01:11, DRB3*01:12, DRB3*01:13, DRB3*01:14, DRB3*01:15, DRB3*02:01, DRB3*02:02:01:01, DRB3*02:02:01:02, DRB3*02:02:02, DRB3*02:02:03, DRB3*02:02:04, DRB3*02:02:05, DRB3*02:03, DRB3*02:04, DRB3*02:05, DRB3*02:06, DRB3*02:07, DRB3*02:08, DRB3*02:09, DRB3*02:10, DRB3*02:11, DRB3*02:12, DRB3*02:13, DRB3*02:14, DRB3*02:15, DRB3*02:16, DRB3*02:17, DRB3*02:18, DRB3*02:19, DRB3*02:20, DRB3*02:21, DRB3*02:22, DRB3*02:23, DRB3*02:24, DRB3*02:25, DRB3*02:26, DRB3*02:27, DRB3*02:28, DRB3*03:01:01, DRB3*03:01:02, DRB3*03:01:03, DRB3*03:02, DRB3*03:03, DRB4*01:01:01:01, DRB4*01:02, DRB4*01:03:01:01, DRB4*01:03:01:03, DRB4*01:03:02, DRB4*01:03:03, DRB4*01:03:04, DRB4*01:04, DRB4*01:05, DRB4*01:06, DRB4*01:07, DRB4*01:08, DRB5*01:01:01, DRB5*01:01:02, DRB5*01:02, DRB5*01:03, DRB5*01:04, DRB5*01:05, DRB5*01:06, DRB5*01:07, DRB5*01:09, DRB5*01:11, DRB5*01:12, DRB5*01:13, DRB5*01:14, DRB5*02:02, DRB5*02:03, DRB5*02:04, DRB5*02:05, ABCEFG_negative_control, DRA_negative_control, DRB_negative_control, DQA_negative_control, DQB_negative_control, DPA_negative_control, and DPB_negative_control.

Within a specific embodiment, the oligonucleotide array comprises one or more of the negative control oligonucleotides having the nucleic acid sequences set forth in Table VI, below. The oligonucleotides in Table VI are negative control oligonucleotides for classical and non-classical HLA molecules. Within another specific embodiment, the oligonucleotide array comprises one or more of the negative control oligonucleotides having the nucleic acid sequences set forth in Table VII, below. The oligonucleotides in Table VII are negative control oligonucleotides for accessory molecules. Within yet another specific embodiment, the oligonucleotide array comprises one or more of the negative control oligonucleotides having the nucleic acid sequences set forth in Table VIII, below. The oligonucleotides in Table VIII are negative control oligonucleotides for KIR molecules. Within still another specific embodiment, the oligonucleotide array comprises one or more of the negative control oligonucleotides having the nucleic acid sequences set forth in Table IX, below. The oligonucleotides in Table IX are negative control oligonucleotides for blood group determining molecules. Within still another specific embodiment, the oligonucleotide array comprises one or more of the negative control oligonucleotides having the nucleic acid sequences set forth in Table X and denoted by "HNN" in Table X, below.

In Tables I-X, within each of the three columns of sequences, the leftmost column indicates the SEQ ID NO ("SIN"), the middle column indicates the name of the sequence (e.g., "N001087" in Table 1) (or in certain Tables, e.g., Tables III-IX, the oligonucleotides' names are just numbers), and the rightmost column indicates the nucleic acid sequences (containing A, C, G, and T). In Tables I and II, the letter "E" at the beginning of an oligonucleotide name indicates that the oligo is "extended" and "N" indicates "normal" (i.e., not extended). In Table X, oligo names begin with "HNN," "HPN," "HPE," or "HPT." As discussed above, "HNN" indicates that the oligo is a negative control oligonucleotide, "HPN" indicates a "normal" (unchanged) oligo, "HPT" indicates a "truncated" oligo, and "HPE" indicates an "extended" oligo. The "HPT" and "HPE" modifications were made to ensure proper melting temperature.

Lengthy table referenced here

US08969254-20150303-T00001

Please refer to the end of the specification for access instructions.

Lengthy table referenced here

US08969254-20150303-T00002

Please refer to the end of the specification for access instructions.

Lengthy table referenced here

US08969254-20150303-T00003

Please refer to the end of the specification for access instructions.

Lengthy table referenced here

US08969254-20150303-T00004

Please refer to the end of the specification for access instructions.

Lengthy table referenced here

US08969254-20150303-T00005

Please refer to the end of the specification for access instructions.

Lengthy table referenced here

US08969254-20150303-T00006

Please refer to the end of the specification for access instructions.

Lengthy table referenced here

US08969254-20150303-T00007

Please refer to the end of the specification for access instructions.

Lengthy table referenced here

US08969254-20150303-T00008

Please refer to the end of the specification for access instructions.

Lengthy table referenced here

US08969254-20150303-T00009

Please refer to the end of the specification for access instructions.

Lengthy table referenced here

US08969254-20150303-T00010

Please refer to the end of the specification for access instructions.

It is to be understood that an oligonucleotide array as described herein can comprise the capture oligonucleotides set forth in any one or more of Tables I-X, above. Further, an oligonucleotide array preferably comprises all of the oligonucleotide sequences set forth in at least one of Tables I-V and the non-negative controls in Table X (oligos with names starting with "HPN", "HPE" or "HPT", but not "HNN"), but within certain embodiments can include fewer oligonucleotides, such as, e.g., 5%, 10%, 20%, 30%, 40%, 50%, 60%, 70%, 80, 90%, 95% or 98% of the sequences set forth in any of Tables I-V. In other embodiments, an oligonucleotide array can comprise nearly all or all (e.g., 70%, 75%, 80%, 85%, 90%, 95%, 98%, 99%, or 100%) of the sequences set forth in one of Tables I-V and fewer than all or nearly all of the sequences set forth in one of the other of Tables I-IX, e.g., 0%, 1%, 5%, 10%, 15%, 20%, 25%, 30%, 35%, 40%, 45%, 50%, 55%, 60%, 65%, 70%, 75%, 80%, 85%, 90%, 95%, 98% or 99% of the oligonucleotides set forth in one or more other of Tables I-IX. By way of example, and without limitation, an oligonucleotide array can comprise all of the capture oligonucleotides set forth in Table I, 50% of the capture oligonucleotides set forth in Table II, and 10% of the capture oligonucleotides set forth in Table III, and optionally, one or more of the oligonucleotides having a sequence set forth in any one or more of Tables VI-IX or the oligos with names starting with "HNN" in Table X.

Solution or Solid Phase Methods for Oligonucleotide Synthesis

Detailed descriptions of the procedures for solution and solid phase synthesis of nucleic acids by phosphite-triester, phosphotriester, and H-phosphonate chemistries are widely available. For example, the solid phase phosphoramidite triester method of Beaticage and Carruthers using an automated synthesizer is described in, e.g., Itakura, U.S. Pat. No. 4,401, 796; Carruthers, U.S. Pat. Nos. 4,458,066 and 4,500,707. See also Needham-VanDevanter, Nucleic Acids Res. 12:6159-6168 (1984); Beigelman Nucleic Acids Res 23:3989-3994 (1995); Oligonucleotide Synthesis: A Practical Approach, Gait (ed.), IRL Press, Washington D.C. (1984), see Jones, chapt 2, Atkinson, chapter 3, and Sproat, chapert 4; Froehler, Tetrahedron Lett. 27:469-472 (1986); Froehler, Nucleic Acids Res. 14:5399-5407 (1986). Methods to purify oligonucleotides include native acrylamide gel electrophoresis, anion-exchange HPLC, as described in Pearson J. Chrom. 255:137-149 (1983). The sequence of the synthetic oligonucleotide can be verified using any chemical degradation method, e.g., see Maxam (1980) Methods in Enzymology 65:499-560, Xiao Antisense Nucleic Acid Drug Dev 6:247-258 (1996), or for solid-phase chemical degradation procedures, Rosenthal, Nucleic Acids Symp. Ser. 18:249-252 (1987).

Solid-Support Based Oligonucleotide Synthesis

An array of capture oligonucleotides at known locations on a single substrate surface can be formed using a variety of techniques known to those skilled in the art of polymer synthesis on solid supports. For example, "light directed" methods (which are one technique in a family of methods known as VLSIPS™ methods) are described in U.S. Pat. No. 5,143, 854. The light directed methods discussed in the '854 patent involve activating predefined regions of a substrate or solid support and then contacting the substrate with a preselected monomer solution. The predefined regions can be activated with a light source shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

Other useful techniques include mechanical techniques (e.g., flow channel, spotting or pin-based methods). In each of the "flow channel" or "spotting" methods, certain activated regions of the substrate are mechanically separated from other regions when the monomer solutions are delivered to the various reaction sites.

A typical "flow channel" method applied to the compounds and libraries of the present invention can generally be described as follows. Diverse probe sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form an array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

Another method which is useful for the preparation of an array of diverse oligonucleotides on a single substrate involves "pin based synthesis." This method is described in detail in U.S. Pat. No. 5,288,514. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry used is such that relatively similar reaction conditions may be utilized to perform each of the reactions, multiple chemical coupling steps can be conducted simultaneously. In the first step of the process, a substrate on which the chemical coupling steps are conducted is provided. The substrate is optionally provided with a spacer (e.g., 15-mer of poly-dT) having active sites on which the capture oligonucleotides are attached or constructed.

Methods for HLA Tissue Typing Using Oligonucleotide Arrays

Within one embodiment, a method for human leukocyte antigen (HLA) tissue typing is provided, wherein said method comprises: (a) contacting a cDNA- or cRNA-containing sample under hybridization conditions with a plurality of capture oligonucleotides specific for HLA polypeptides, wherein said hybridization conditions facilitate hybridization of a subset of the capture oligonucleotides to complementary sequences present in the cDNA or cRNA; (b) detecting a hybridization pattern for said cDNA or cRNA; and (c) assigning to the sample, based on the hybridization pattern, an HLA tissue type; wherein the capture oligonucleotides are from about 17 to about 60 nucleotides in length and each capture oligonucleotide with respect to its exact complement has a melting temperature of about 64 degrees Celsius; wherein said capture oligonucleotides comprise subsets of oligonucleotides that collectively target classical HLA polypeptide-encoding nucleic acids ("classical HLA oligo subsets"), each classical HLA oligo subset targeting a different classical HLA polypeptide-encoding nucleic acid; and wherein each of said classical HLA oligo subsets comprises a set of overlapping oligonucleotides that cover every single nucleotide position in the mRNA sequences coding for the classical HLA polypeptides from 5' to 3' and are sequentially shifted by 1-5 nucleotides from the 5' end of the preceding overlapping oligonucleotide. In a specific embodiment, the capture oligonucleotides comprise subsets of oligonucleotides that collectively target all known classical HLA polypeptide-encoding nucleic acids. In one embodiment, the capture oligonucleotides are immobilized on a substrate (e.g, a microarray).

In another embodiment, a method for human leukocyte antigen (HLA) tissue typing is provided, wherein said method comprises: (a) contacting a cDNA- or cRNA-containing sample under hybridization conditions with a plurality of capture oligonucleotides specific for HLA polypeptides, wherein said hybridization conditions facilitate hybridization of a subset of the capture oligonucleotides to complementary sequences present in the cDNA or cRNA; (b) detecting a hybridization pattern for said cDNA or cRNA; and (c) assigning to the sample, based on the hybridization pattern, an HLA tissue type; wherein the capture oligonucleotides are from about 17 to about 60 nucleotides in length and each capture oligonucleotide with respect to its exact complement has a melting temperature of about 64 degrees Celsius; wherein said capture oligonucleotides comprise subsets of oligonucleotides that collectively target a panel of reference classical HLA polypeptide-encoding nucleic acids, wherein the panel comprises nucleic acids encoding all reference classical HLA polypeptides to which it is desired to test the HLA cDNA or cRNA in the sample for hybridization potential ("classical HLA oligo subsets"), each classical HLA oligo subset targeting a different classical HLA polypeptide-encoding nucleic acid; and wherein each of said classical HLA oligo subsets comprises a set of overlapping oligonucleotides that cover every single nucleotide position in the mRNA sequences coding for the classical HLA polypeptides from 5' to 3' and are sequentially shifted by 1-5 nucleotides from the 5' end of the preceding overlapping oligonucleotide.

Within certain embodiments of the above-describe method for HLA tissue typing, in the step (a), the cDNA or cRNA was detectably labeled during the making, and the detecting step (c) comprises detecting the detectably labeled cDNA or cRNA. Within other embodiments, the detecting step (b) comprises the use of labeled detection probes.

Within another embodiment, the capture oligonucleotides in the above-described method for HLA tissue typing further comprise a plurality of oligonucleotide subsets that collectively targets non-classical HLA polypeptide-encoding nucleic acids ("non-classical HLA oligo subsets"), each non-classical HLA oligo subset targeting a different non-classical HLA polypeptide-encoding nucleic acid; wherein each of said non-classical HLA oligo subsets comprises a set of overlapping oligonucleotides that cover every single nucleotide position in the mRNA sequences coding for the non-classical HLA polypeptides from 5' to 3' and are sequentially shifted by 1-5 nucleotides from the 5' end of the preceding overlapping oligonucleotide. In a specific embodiment, the plurality of oligonucleotide subsets that collectively targets non-classical HLA polypeptide-encoding nucleic acids collectively target all known non-classical HLA polypeptide-encoding nucleic acids. In one embodiment, the capture oligonucleotides are immobilized on a substrate (e.g, a microarray). In another embodiment, said capture oligonucleotides comprise subsets of oligonucleotides that collectively target a panel of reference non-classical HLA polypeptide-encoding nucleic acids, wherein the panel comprises nucleic acids encoding all reference non-classical HLA polypeptides to which it is desired to test the HLA cDNA or cRNA in the sample for hybridization potential ("non-classical HLA oligo subsets"), each classical HLA oligo subset targeting a different non-classical HLA polypeptide-encoding nucleic acid.

Within another embodiment, the capture oligonucleotides in the above-described method for HLA tissue typing further comprise a plurality of oligonucleotide subsets that collectively targets nucleic acids encoding accessory molecules ("accessory molecule oligo subsets"), and said method further comprises the step of assigning to the cell, based on the hybridization pattern, an accessory molecule phenotype; wherein each of said accessory molecule oligo subsets comprises a set of overlapping oligonucleotides that cover every single nucleotide position in the mRNA sequences coding for the accessory molecules from 5' to 3' and are sequentially shifted by 1-5 nucleotides from the 5' end of the preceding overlapping oligonucleotide.

Within still another embodiment, the capture oligonucleotides in the above-described method for HLA tissue typing further comprise a plurality of oligonucleotide subsets targeting killer-cell immunoglobulin-like receptor (KIR) polypeptide-encoding nucleic acids ("KIR oligo subsets"), and said method further comprises the step of assigning to the cell, based on the hybridization pattern, a KIR polypeptide phenotype; wherein each of said KIR oligo subsets comprises a set of overlapping oligonucleotides that cover every single nucleotide position in the mRNA sequences coding for the KIR polypeptides from 5' to 3' and are sequentially shifted by 1-5 nucleotides from the 5' end of the preceding overlapping oligonucleotide.

Within yet another embodiment, the capture oligonucleotides in the above-described method for HLA tissue typing further comprise a plurality of oligonucleotide subsets targeting blood group-determining polypeptide encoding nucleic acids ("blood group determining oligo subsets"), and said method further comprises the step of assigning to the cell, based on the hybridization pattern, a blood group phenotype; wherein each of said blood group determining oligo subsets comprises a set of overlapping oligonucleotides that cover every single nucleotide position in the mRNA sequences coding for the blood group-determining polypeptides from 5' to 3' and are sequentially shifted by 1-5 nucleotides from the 5' end of the preceding overlapping oligonucleotide.

In any of the above-described embodiments, the array can further comprise negative control oligonucleotides, such as, e.g., one or more of those having the nucleic acid sequences set forth in Tables VI-IX, or the oligos with names starting with "HNN" in Table X, above.

In any of the above-described embodiments, cDNA or cRNA can be made from an mRNA-containing sample according to any suitable method in the art (e.g., PCR). Further, the sample can be obtained from any suitable source, such as, e.g., a cell or cells. A cell or cells can be obtained from any suitable source of cells, such as, e.g., cells from a tissue from e.g., a subject (e.g., a donor or recipient or patient), cells obtained from blood or other bodily fluid, or cell line.

Within certain embodiments, the microarray can comprise any suitable substrate, e.g., solid support, such as those described herein. The fidelity of the hybridization assay is governed by the stability differences between perfectly matched and mismatched duplexes. Preferably, a single set of hybridization conditions that can provide a clear discrimination between matches and mismatches for all polymorphisms in each target gene (e.g., HLA polypeptide-encoding gene) should be used.

Within one embodiment, the cDNA samples were hybridized to custom oligonucleotide slides at 64° C. for 16 h, however, other hybridization conditions are also possible, can be determined by one of ordinary skill in the art.

The detecting step (b) in the above method can be carried out according to any suitable methods. For example, in one embodiment, the cDNA or cRNA hay have been directly labeled (e.g., with fluorescent dye). In another embodiment, labeled detection probes (e.g., fluorescent detection probes) can be used. For example, in a certain embodiments, when the capture oligonucleotides are immobilized on a solid support, such as, not limited to a microarray, the labeled detection probes can be hybridized to the microarray according to suitable methods known in the art. Such detection probes are designed with specific nucleic acids sequences to target the nucleic acids hybridized to the capture oligonucleotides attached to the array substrate (e.g., slide). Method for designing such detection probes are known in the art. Briefly, the probe sequences are assembled computationally based upon nucleotide sequence databases of the target loci. The detection probes are labeled and are detected using a suitable detector (e.g., in the case of fluorescent dyes, a fluorescent scanner may be used to detect and quantify the intensity of the signal.

Those of skill in the art will understand that the above-described detection probe sequences are exemplary, and that other probes having other nucleic acid sequences can also be used, alternatively, or in addition, to detect the microarray targets described herein. Further, the sequences of such detection probes can be determined according to routine methods known in the art.

In the above methods, the probe signal (of either the directly labeled cDNA or cRNA sample or of the detection probes) can be analyzed using pattern recognition software. A specific approach for analyzing the probe signal (and hybridization pattern) is described in detail in Example 2, below.

Based on the analysis of the microarray data, the HLA tissue type is assigned based on the specific combination of HLA alleles present in the sample.

Diagnostic Methods Using Oligonucleotide Arrays

Within a specific embodiment, methods for deriving donor/recipient compatibility in tissue transplants are provided. Tissue transplants can include, e.g., both solid organs and cells (e.g., bone marrow). In order to determine donor/recipient compatibility in tissue transplants, the practitioner should compare the HLA tissue type of both the potential donor and the recipient. The HLA tissue type of each is assigned according to the methods described above.

Once the HLA tissue types of the patient and potential donor are determined, donor/recipient compatibility is derived according to the following criteria: donor and recipient are considered fully matched when their HLA are phenotypically identical across HLA-A, HLA-B, HLA-C, HLA-DRA, HLADRB1, HLA-DRB1,4,5, HLA-DQA1, HLA-DQB1, HLA-DPA1, HLA-DPB1. In the case that a matched donor cannot be found, a mismatch must be accepted at the discretion of the physician conducting the donor search.

Within other embodiments, methods for diagnosing or predicting the likelihood of an HLA-linked genetic defect, disease, inadequate or undesirable response to a vaccine, biologic treatment (recombinant protein, biosimilar or equivalent), or infectious organism or condition in said subject, wherein the step is based on one or more assigned tissue types or phenotypes selected from the group consisting of: a classical HLA tissue type, a non-classical HLA tissue type, an accessory molecule phenotype, a KIR polypeptide phenotype, and a blood group phenotype. HLA associated diseases include, for example, and without limitation, type 1 diabetes mellitus (see, Larsen, C. E. & Alper, C. A. Current Opinion in Immunology 16, 660-667 (2004)); rheumatoid arthritis (see, Khan et al. (1983), Tissue Antigens, 22: 182-185), and ankylosing spondylitis (Gonzalez-Roces, S., et al. Tissue Antigens, 49: 116-123).

Within other embodiments, methods for diagnosing or predicting the likelihood of an HLA-linked genetic defect, disease, inadequate or undesirable response to a vaccine, biologic treatment (recombinant protein, biosimilar or equivalent), or infectious organism or condition in said subject, wherein the step is based on one or more assigned HLA tissue types or phenotypes selected from the group consisting of: a classical HLA tissue type, a non-classical HLA tissue type, an accessory molecule phenotype, a KIR polypeptide phenotype, and a blood group phenotype.

Within still other embodiments, methods for determining the likely response of a subject to a particular treatment regimen are provided, wherein the treatment regimen is selected from the group consisting of: bone marrow transplantation, immunosuppressive regimen, antiviral drug regimen, antiviral drug resistance, antiretroviral drug regimen, and autoimmunity drug regimen, and wherein the method is based on determining according to the method described herein one or more assigned HLA tissue types or phenotypes selected from the group consisting of: a classical HLA tissue type, a non-classical HLA tissue type, an accessory molecule phenotype, a KIR polypeptide phenotype, and a blood group phenotype.

Within yet other embodiments, methods for determining whether a subject is likely to develop antiretroviral drug resistance or cancer drug regimen resistance are provided, wherein the method is based on determining according to the method described herein one or more assigned HLA tissue types or phenotypes selected from the group consisting of: a classical HLA tissue type, a non-classical HLA tissue type, an accessory molecule phenotype, a KIR polypeptide phenotype, and a blood group phenotype.

The following examples are meant to illustrate, not limit, the invention.

EXAMPLES

Example 1

Design of Oligonucleotide Microarray

This Example demonstrates the design of a microarray for rapid and economical identification of HLA profiles of individuals and characterization of the HLA genotypes and polymorphisms in antigen processing and presentation machinery. The set of HLA capture oligonucleotide spotted on the array comprised 3821 classical HLA-I class I sequences (1193 HLA-A, 1799 HLA-B and 829 HLA-C), 1249 HLA-II class II sequences (901 HLA-DR, 169 HLA-DP, 147 HLA-DQ, 11 HLA-DM, 21 HLA-DO), and 188 other HLA region sequences (i.e., non-classical HLA) (9 HLA-E, 21-F, 46-G, 101 MIC, and 11 TAP), 504 KIR and 68 antigen presentation and processing genes (accessory molecules), a total of 5830 coding sequences. The array also contained 65 negative control sequences for all probes for all coding sequences. The total number of probes covering the complete set of HLA loci and accessory molecules on each array was 178,857 providing a dense tiling coverage (the overlapping probes are sequentially shifted by 1-2 nucleotides (i.e., step 1 or step 2 shifts) of all HLA polypeptides. The flow chart shown in FIG. 1 describes the processing steps in HLA typing using microarray. Each of the steps is described in detail, below.

Capture Oligonucleotide Design

The primary data necessary to design the capture oligonucleotides consists of gene and allele identifiers and the associated nucleotide sequences. The sequences are organized into sequence groups of sufficient homology to produce an accurate alignment. Sequence groups can consist of all alleles of a locus, or of multiple loci when they are highly homologous. Sequence groups include: HLA class I (HLA-A, -B, -C, -E, -F, and -G), HLA-DRB (DRB1, DRB3, DRB4, and DRB5), HLA-DRA, HLA-DQA, HLA-DQB, HLA-DPA, HLA-DPB, HLA-DMA, HLA-DMB, HLA-DOA, HLA-DOB, TAP1, TAP2, MICA, MICB, KIR, endoplasmic reticulum genes (B2M, tapasin, CANX, CALR, PDIA2, PDIA3, ERAP1), aminopeptidase genes (TPP2, BLMH, LAP3), proteasome (PSMA1, PSMA2, PSMA3, PSMA4, PSMA5, PSMA6, PSMA7, PSMA8, PSMB1, PSMB2, PSMB3, PSMB4, PSMB5, PSMB6, PSMB7, PSMB8, PSMB9, PSMB10, PSMB11, PSMC1, PSMC2, PSMC3, PSMC4, PSMC5, PSMC6, PSMD1, PSMD2, PSMD3, PSMD4, PSMD5, PSMD6, PSMD7, PSMD8, PSMD9, PSMD10, PSMD11, PSMD12, PSMD13, and PSMD14). Specific parameters of this method are selected to produce the best results for the sets of genes and alleles that are targeted for typing. These parameters include the tiling interval (step size, e.g., sequential shifting by 1 or 2 nucleotides), target melting temperature (each capture oligonucleotide is designed to have the closest possible melting temperature to the target melting temperature); and negative control replacement interval (this is the interval at which replacements are made in a consensus sequence of a sequence group to create capture oligonucleotides that do not occur in the target genes and alleles).

Negative Control

For each sequence group, an artificial negative control sequence is generated. The sequences in this group are aligned and a consensus sequence is determined. Alternate nucleotides are chosen at specific intervals (10 nt) within the consensus sequence and replaced by nucleotides not represented in the sequence alignment at the given position. If the nucleotide at a selected position is not fully conserved, the nearest fully conserved residue is selected for nucleotide replacement.

To preserve target melting temperature the following replacements can be done: A to T, T to A, C to G, and G to C. The nucleotide on the left (e.g., the A in "A to T") represents a conserved one from the sequences, and the nucleotide on the right (e.g., the T in "A to T") represents those present in the negative control probes. See, FIG. 2, which demonstrates a set of probes (P1 to P13) covering A*02:01:01:01 sequence and their corresponding negative control probes (P1N to P 13N) generated based on the consensus sequence of HLA class I sequence group.

Sequence Alignments

A sequence alignment is generated containing all the sequences from within a sequence group as well as the corresponding negative control sequence for that group. The aligned sequences are used in the remaining steps.

Tiling

Capture oligonucleotide sequences are subsequences of the alignment generated by stepping through each sequence at a specific interval called the step size. The step size will determine whether a capture oligonucleotide is created for each position (e.g. step size=1) or a subset of positions (e.g. step size=2, for every second position). The following capture oligonucleotide selection process is applied for each position:

A capture oligonucleotide sequence is a subsequence in the alignment determined by a start position and an end position.

For a given start position, the end position giving the closest melting temperature to a target melting temperature is identified.

Length restrictions: capture oligonucleotides shorter than 20 nucleotides are extended to 20 by appending thymines to the sequence. Capture oligonucleotides longer than 60 nucleotides are truncated to 60.

The capture oligonucleotide sequence becomes part of the final set of capture oligonucleotides under the condition that the sequence is not already represented in the final set of capture oligonucleotides.

FIG. 3 shows a set of tiling capture oligonucleotides (P1 to P13) covering A*02:01:01:01 sequence.

Computational Capture Oligonucleotide Generation

Determination of Optimal Target Melting Temperature

Figure 4:
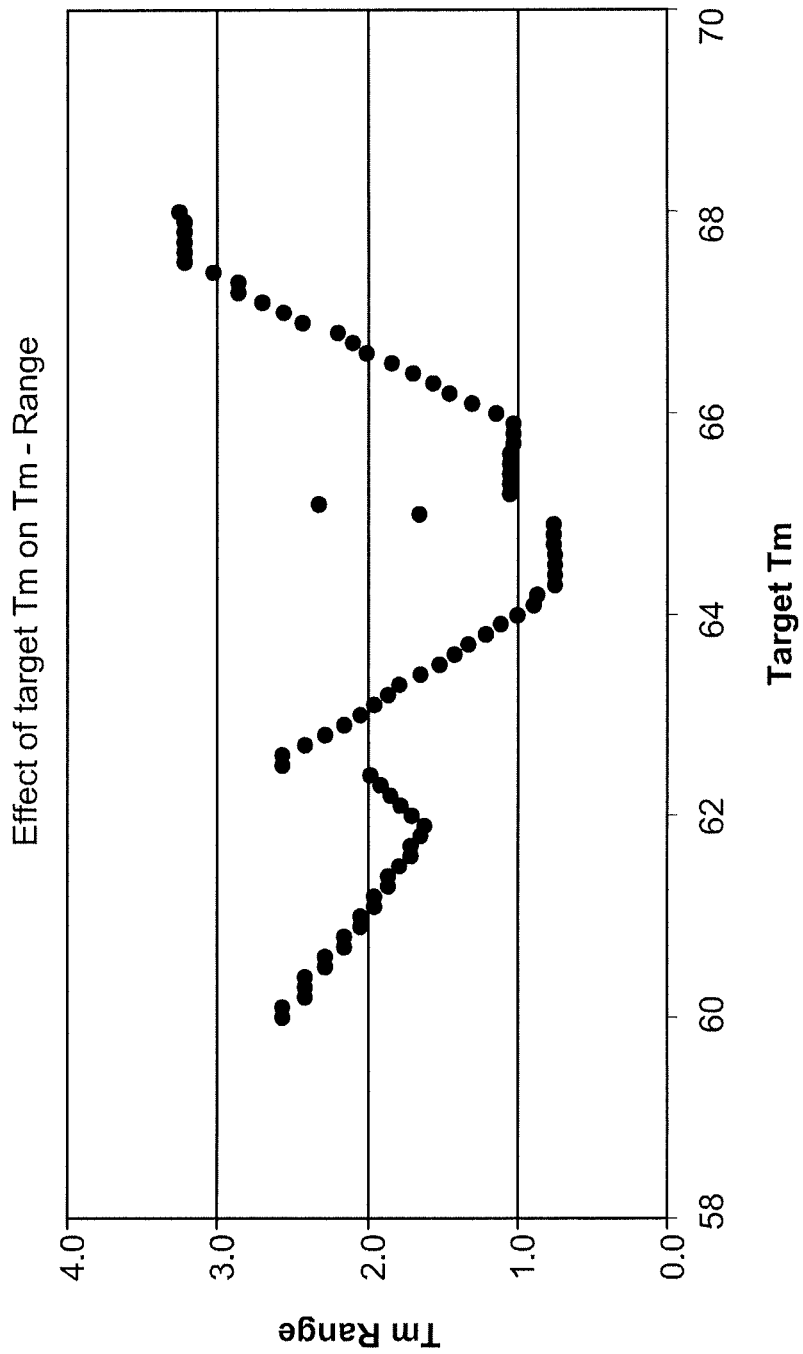
FIG. 4. is a graph demonstrating the relationship between target melting temperature and the capture oligonucleotide melting temperature range.

The optimal melting temperature was defined using a systematic analysis. This analysis identified that the targeted melting temperature is 64.3° C. providing the minimal deviation from the target temperature of all capture oligonucleotides. See FIG. 4, which demonstrates the relationship between target melting temperature and the capture oligonucleotide melting temperature range.

The steps listed above were executed to create a tiled microarray of a given target melting temperature. The actual melting temperatures of capture oligonucleotides (with respect to their exact complements) in the array will span a range specific to that chip. In general, an optimal target melting temperature is chosen which will minimize the range of the melting temperatures of the generated capture oligonucleotides. This is done computationally by performing the steps of the previous section iteratively over a range of target melting temperatures. The final capture oligonucleotides are those generated using the optimal target melting temperature giving the narrowest melting temperature range.

Melting Temperature

Melting temperature was calculated for the nucleotide sequences according to the following formula: $Tm=64.9+41*(N_G+N_c-16.4)/(N_A+N_T+N_G+N_C)$, where $N_A$, $N_T$, $N_G$, and $N_C$ are the number of the bases A,T,G,C in the sequence, respectively.

Figure 5A:
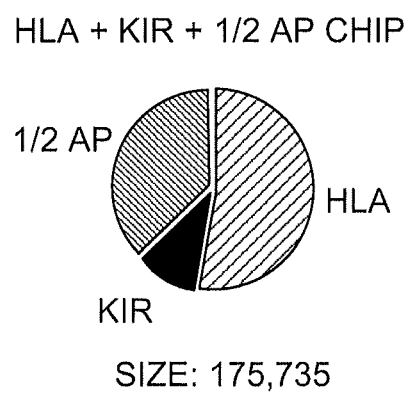
FIG. 5 contains pie graphs demonstrating the portioning of capture oligonucleotides with regard to (A) typing targets and (B) negative control oligonucleotides.
Figure 5B:
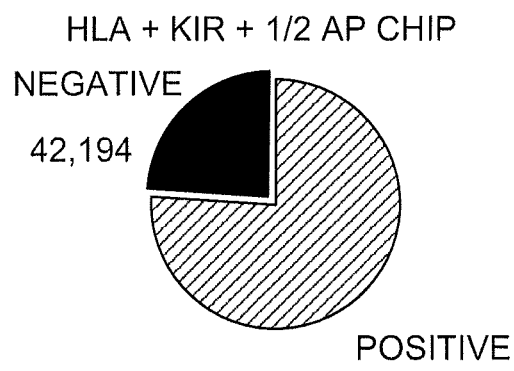
Figure 6A:
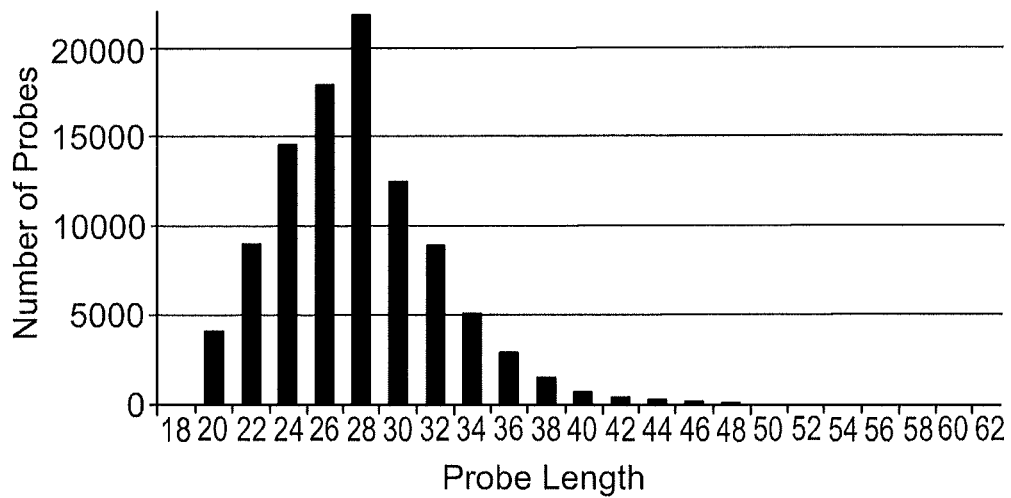
FIG. 6 shows histograms of capture oligonucleotide distribution according to (A) capture oligonucleotide length and (B) melting temperature.
Figure 6B:
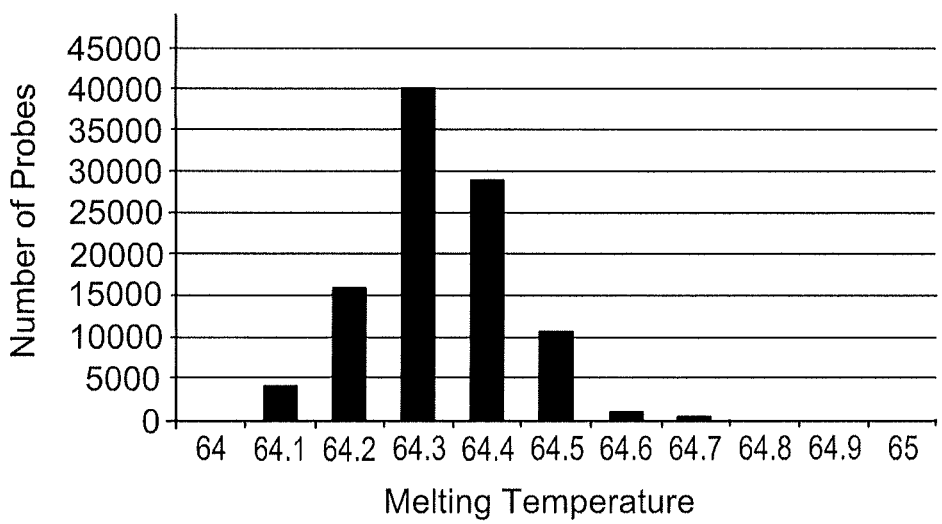

The method of capture oligonucleotide generation outlined above was applied to the HLA, KIR, and accessory molecules (antigen presentation) systems with the intent of generating no more than 180,000 probes. This can be achieved by using a step size of 2 for the set of accessory molecules. The pie charts in FIG. 5A and FIG. 5B demonstrate that this method results in the majority of capture oligonucleotide detecting (i.e., targeting nucleic acids encoding) HLA alleles, followed by accessory molecules and KIR molecules. The strategy of targeting the optimal melting temperature results in a wide range of probe lengths (FIG. 6A), but a minimal range of probe melting temperatures (FIG. 6B).

Example 2

Microarray Experiment—Handling of Samples and Extraction of Probe Signals

The microarray and hybridization experiment was performed using Agilent custom-made 4×180K arrays with four identical arrays printed on each slide. Capture oligonucleotides were designed using eArray<earray.chem.agilent.com/earray> software—input data were the working set of capture oligonucleotides. Arrays were printed using Agilent's SurePrint technology and included Agilent's control probes.

Peripheral blood samples were collected from six donors and from five HLA typed EBV transformed reference B cell lines. Standard HLA typing was performed by an external clinical HLA typing laboratory. Donor RNA from frozen PBMC and cell lines were isolated using Total RNA Isolation Mini Kit (RNeasy) from Qiagen. RNA quality was determined using The RNA 6000 Nano Chip kit from Agilent Technologies. Fluorescent cRNA sample for hybridization to the capture oligonucleotides immobilized on the array were synthesized from total RNA using the Agilent single color direct labeling kit. The labeled sample cRNA was hybridized to custom slides at 64° C. for 16 h, based on the reference capture oligonucleotide melting temperature of 64.3° C. and advice from the microarray producer. The slides were scanned using an Agilent Microarray scanner. After the slides were scanned using an Agilent Microarray scanner, Agilent Feature Extraction program was used to convert the fluorescence intensity into signal files.

Samples were hybridized to an HLA chip array. Standard Agilent hybridization protocol was followed at a temperature of 64° C. The chips were scanned using an Agilent Microarray scanner and they hybridization pattern (signals of bound, labeled cRNA) was detected using Agilent Feature Extraction program.

Probe Signal Preprocessing

Global scaling of signals was performed, so that all arrays had the same minimum, maximum, and average signal. Normalization that mapped signals to a scale of 1-20,000 was performed where minimum was set to 1, maximum to 20,000, and the array-wide average to 1,000. The detailed steps involved in signal preparation is shown below:

Signal Preparation
1. Signal extraction
   a. If a capture oligonucleotide is found on the chip multiple times, then only one instance is considered.
2. Scaling
   a. 4,000 probes with minimum=1
   b. Maximum=20,000
   c. Mean=1,000
3. Elimination of bad (incorrect) signals
   a. Remove from further analysis probes with global high signals (the probe signals are equal to or larger than 10000 for every array)
   b. The elimination is applied to all variants of algorithms This transformation produced comparable signals for all microarrays. The data from 32 array experiments showed high reproducibility of array-wide signals. The correlation coefficients were always r>0.97 for samples from the same individual, while for samples from different individuals were 0.8<r<0.96. These values of r were sufficient to identify when the same sample has been used in different arrays.

Statistical analysis was performed for probe signals at each alignment position. The maximum, minimum, mean, median, and geometric mean of the probe signals at each alignment poistion were calculated as shown for an exemplary alignment position in FIG. 7.

Data cleaning programs were made for outlier detection. Problematic probes, such as probes with constant global high signal of 20,000 on most of the 32 arrays, were identified. The signals of these probes were marked as not trustworthy.

Signal Analysis and Prediction of HLA Profiles

Figure 8:
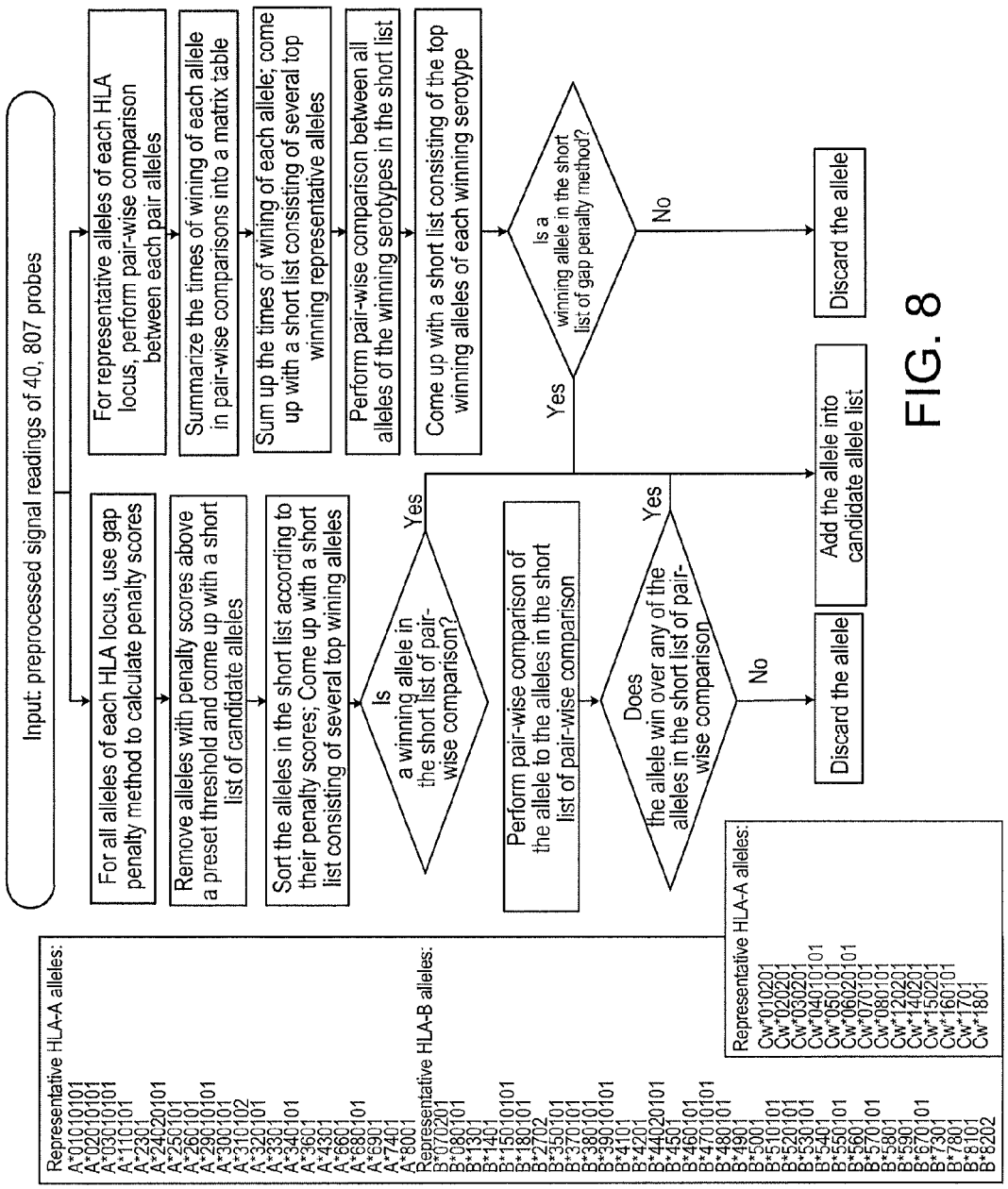
FIG. 8 is flow diagram showing the approach for combining gap penalty method and pair-wise comparison method for identification of sample HLA alleles.

Two complimentary methods, gap penalty method and pairwise comparison methods, were applied for the prediction of sample HLA profiles. FIG. 8 shows the process of combining these two methods for accurate prediction of candidate HLA alleles. Each of the methods will be introduced in details.

Gap Penalty Method

Figure 9A:
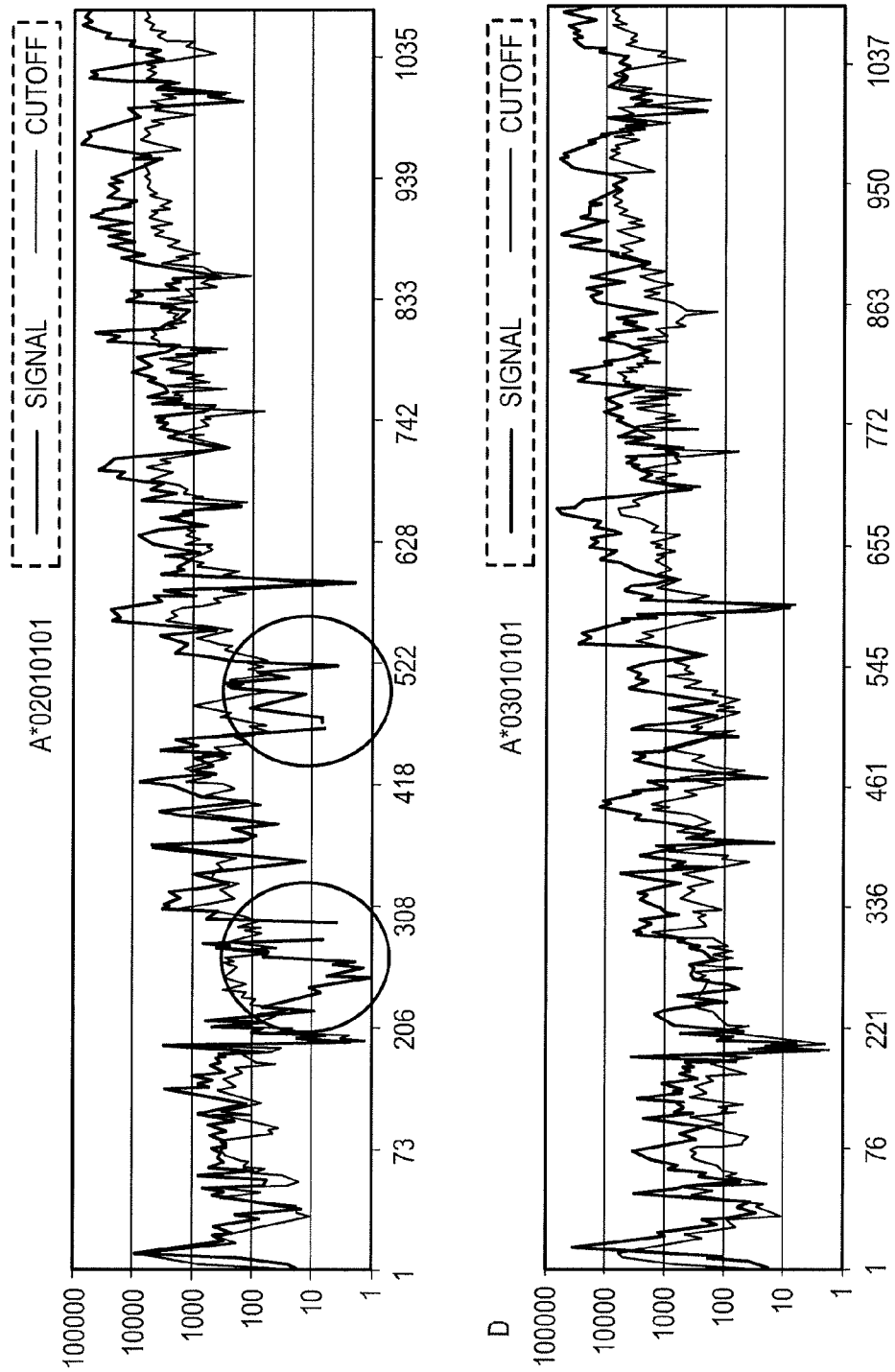
FIG. 9 contains graphs showing A*02010101 and A*03010101 probe signals of (A) sample D and (B) sample E. The thick, darker lines plot probe signals at each alignment position and the thinner, lighter-colored lines plots thresholds (cutoffs) at each position. The threshold used here is the 10% of the maximum signal at each position.
Figure 9B:
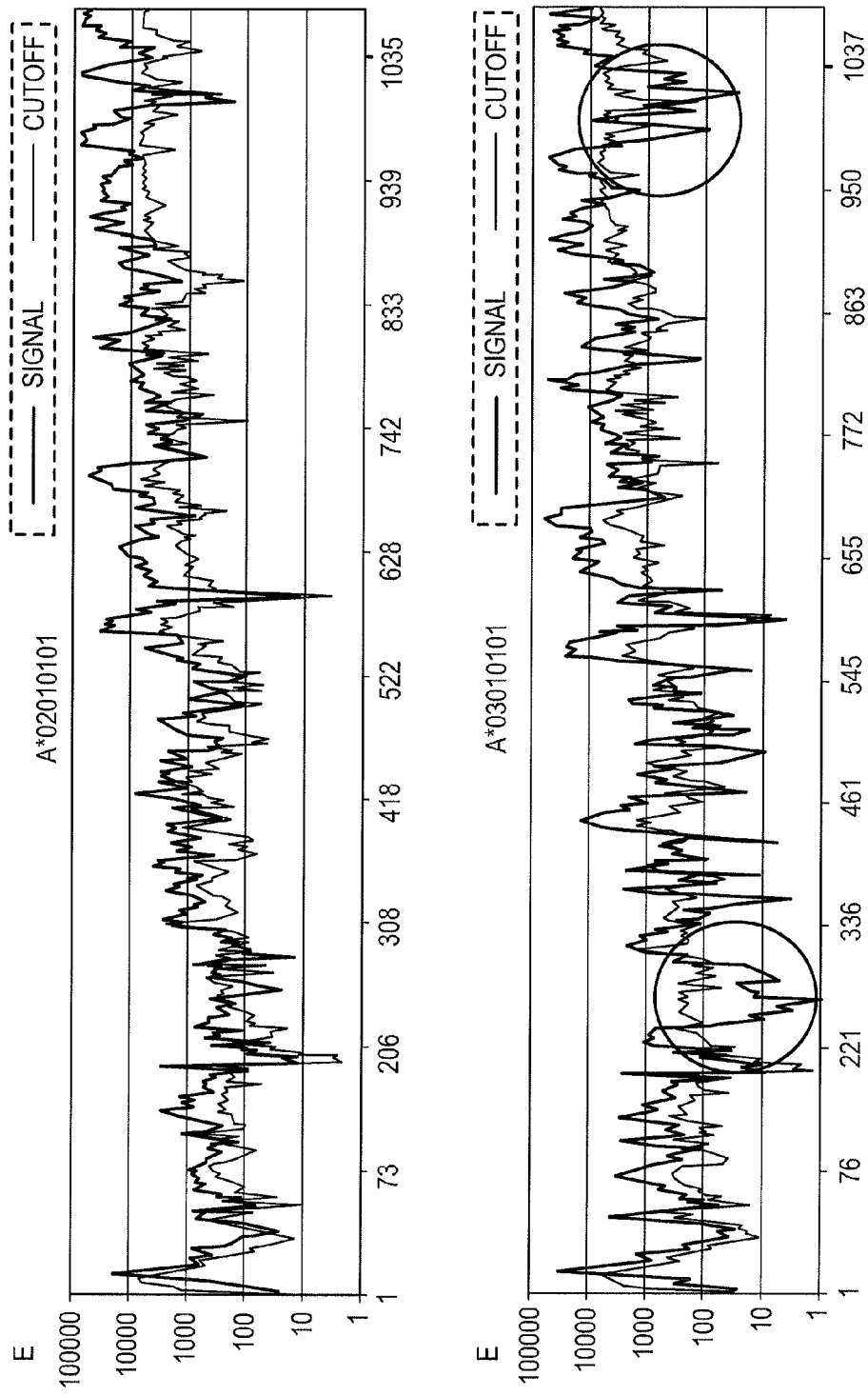

If an allele is present in a sample, the majority of the probe signals of that allele should be reasonably high. If an allele has a long region of continuous probes with very low signals, it is highly likely that the allele is not present in the sample. As marked out by circles in FIG. 9A, there are two regions with continuous low signal probes for A*02010101. It suggests that A*02010101 is not presented in sample D. Similarly, in FIG. 9B, there are two regions with continuous low signal probes for A*03010101. It suggests that A*03010101 is not presented in sample D. Using this rational, the gap penalty method was developed.

The detail steps involved in gap penalty method are described in detail, below:

Gap Penalty
1. For each allele, three scores are generated and used with cutoffs to eliminate obviously negative alleles: gap penalty, maximum gap length, and the average signal of an allele;
2. Cutoff for low probe signals (default value: 10% of the maximum signal at a position):
   a. This parameter defines gaps as a percentage of maximum signal;

b. Gap is a signal having less than the cutoff percent of maximum signal;
3. Gap penalty threshold:
   a. Contiguous gap positions contribute to this score exponentially;
   b. Noncontiguous gaps are simply added together;
   c. Penalty of an allele=$\Sigma G_i \times G_i$, where $G_i$ is the length of ith gap in the sequence;
   d. High potential as a ranking method;
4. Maximum gap length threshold (default value: 11):
   a. Gap length is the number of contiguous positions below the low probe signal percentage (see point 2);
5. Average signal threshold (Default value: 2.5):
   a. The allele must have a score, 10/average signal, less than this cutoff;
   b. The average signal is inverted in order to make this score inversely proportional to the allele's probability of being present (to fit with the other gap length and gap penalty).

Pairwise Comparison Method

Figure 10A:
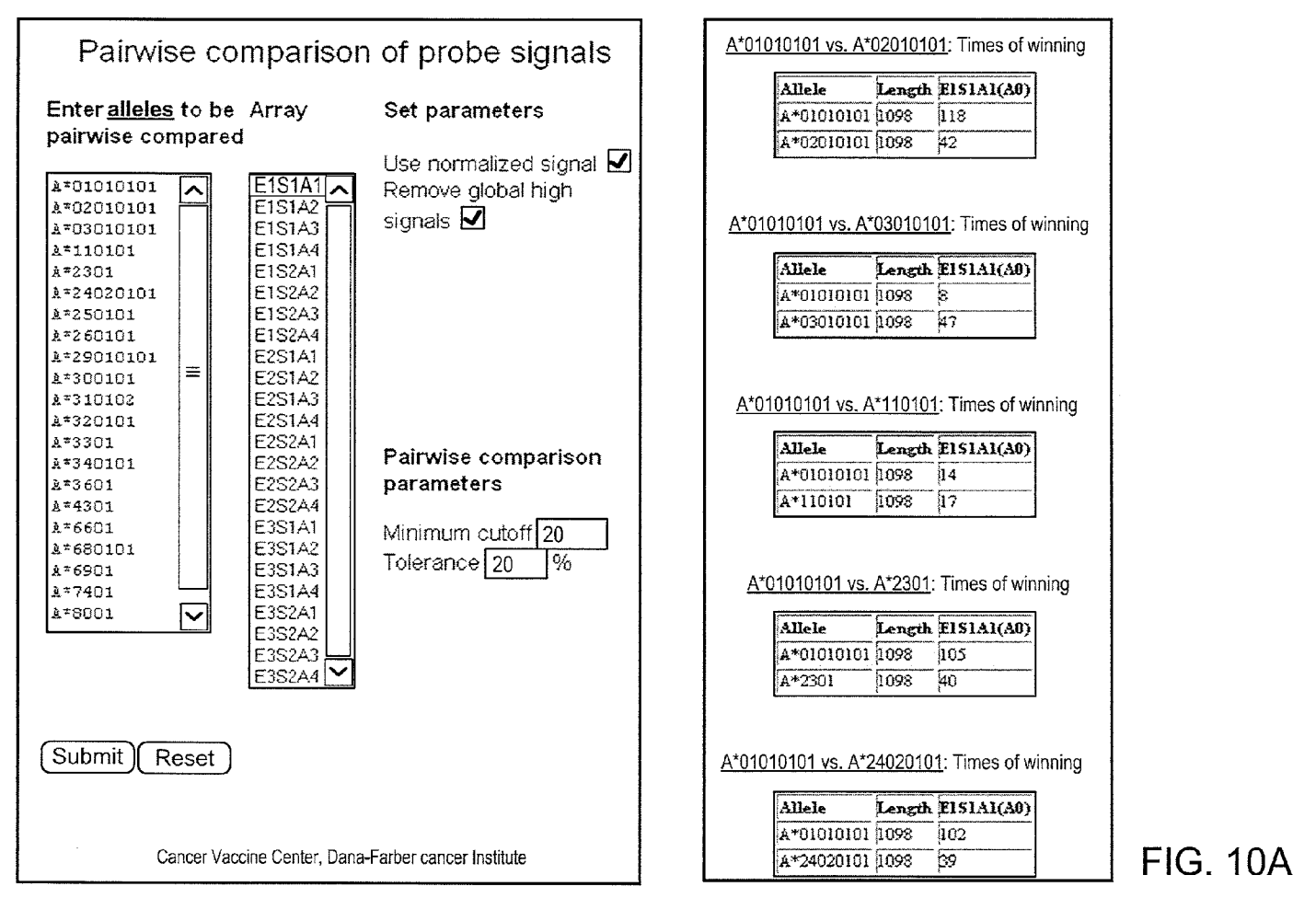

Given two alleles present in a multiple sequence alignment, the pairwise comparison method identifies the capture oligonucleotides containing sequence variations between the two alleles, compares the signals of each capture oligonucleotide pair, and votes on winning based on the signals. The detailed steps involved in the gap penalty method are shown below and in FIGS. 10A-C:

Pairwise Comparison
1. This is a triple layer method:
   a. Probes (oligonucleotides) from a pair of alleles are compared and voting is performed;
   b. The winner of the two alleles is accessed;
   c. The winner of all the alleles over all the comparisons is assessed;
2. Rules for ignoring a position when comparing two alleles:
   a. Low signal—if both signals <20;
   b. Similar—signal difference <30% of higher signal;
   c. Unique probe—winning probe is only present in 1 allele;
   d. Uninformative—winner is in a pre-defined set probes that are similar across all arrays;
   e. Masking—if the following three criteria are fulfilled;
      i. Loser signal<median signal for this position;
      ii. Winning probe's HLA coverage>twice that of losing probe;
      iii. Winning probe's HLA coverage>100 (class I); 20 (class II);
3. Elimination strategy—after all pairs have been compared, an allele will be eliminated from the list of candidates if:
   a. The winning allele is not a partial sequence; and
      i. The loosing allele has 1 or less votes and the difference in votes >=4; or
      ii. the losing votes are >1 and the difference >=20;
4. Ranking strategy (alternative to elimination):
   a. Difference in votes is calculated for each allele pair;
   b. The average of all difference for an allele is calculated.

* * *

Patents, patent applications, publications, product descriptions, and protocols are cited throughout this application, the disclosures of which are incorporated herein by reference in their entireties for all purposes.

A number of embodiments of the invention have been described. Nevertheless, it will be understood that various modifications may be made without departing from the spirit and scope of the invention. It is further to be understood that all values are approximate, and are provided for description. Accordingly, other embodiments are within the scope of the following claims.

LENGTHY TABLES

The patent contains a lengthy table section. A copy of the table is available in electronic form from the USPTO web site (http://seqdata.uspto.gov/?pageRequest=docDetail&DocID=US08969254B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08969254B2). An electronic copy of the "Sequence Listing" will also be available from the USPTO upon request and payment of the fee set forth in 37 CFR 1.19(b)(3).

What is claimed is:

1. A method for human leukocyte antigen (HLA) tissue typing, said method comprising:
   (a) contacting a cDNA-or cRNA-containing sample under hybridization conditions with a plurality of capture oligonucleotides specific for HLA polypeptides, wherein said hybridization conditions facilitate hybridization of at least a portion of the plurality of capture oligonucleotides to complementary sequences present in the cDNA or cRNA;
   (b) detecting a hybridization pattern for said cDNA or cRNA; and
   (c) assigning to the sample, based on the hybridization pattern, an HLA tissue type;

wherein the capture oligonucleotides are from about 17 to about 60 nucleotides in length and each capture oligonucleotide with respect to its exact complement has a melting temperature of about 64 degrees Celsius;

wherein said capture oligonucleotides comprise subsets of oligonucleotides that collectively target classical HLA polypeptide-encoding nucleic acids ("classical HLA oligo subsets"), each classical HLA oligo subset targeting a different classical HLA polypeptide-encoding nucleic acid;

wherein each of said classical HLA oligo subsets comprises a set of overlapping oligonucleotides that cover every single nucleotide position in each of the full-length coding regions of mRNA sequences coding for the classical HLA polypeptides from 5' to 3' and are sequentially shifted by 1-5 nucleotides from the 5' end of the preceding overlapping oligonucleotide, and wherein said classical HLA oligo subsets comprise the sequences set forth in Table I or the normal (indicated by "HPN"), extended (indicated by "HPE") and truncated (indicated by "HPT") sequences set forth in Table X.

2. The method of claim 1, wherein said classical HLA polypeptide-encoding nucleic acids encode HLA polypeptides selected from the group consisting of HLA-A, HLA-B, HLA-C, HLA-DR, HLA-DP, and HLA-DQ.

3. The method of claim 1, wherein said capture oligonucleotides further comprise a plurality of oligonucleotide subsets that collectively targets non-classical HLA polypeptide-encoding nucleic acids ("non-classical HLA oligo subsets"), each non-classical HLA oligo subset targeting a different non-classical HLA polypeptide-encoding nucleic acid;

wherein each of said non-classical HLA oligo subsets comprises a set of overlapping oligonucleotides that cover every single nucleotide position in the mRNA sequences coding for the non-classical HLA polypeptides from 5' to 3' and are sequentially shifted by 1-5 nucleotides from the 5' end of the preceding overlapping oligonucleotide.

4. The method of claim 3, wherein said non-classical HLA polypeptide-encoding nucleic acids encode HLA polypeptides selected from the group consisting of HLA-E, HLA-F, HLA-G, DM, DO and MIC.

5. The method of claim 1, wherein said capture oligonucleotides further comprise a plurality of oligonucleotide subsets that collectively targets nucleic acids encoding accessory molecules important in HLA-linked peptide presentation and/or processing ("accessory molecule oligo subsets"), and said method further comprises the step of assigning to the sample, based on the hybridization pattern, an accessory molecule phenotype;

wherein each of said accessory molecule oligo subsets comprises a set of overlapping oligonucleotides that cover every single nucleotide position in the mRNA sequences coding for the accessory molecules from 5' to 3' and are sequentially shifted by 1-5 nucleotides from the 5' end of the preceding overlapping oligonucleotide.

6. The method of claim 5, wherein said accessory molecules are selected from the group consisting of LMP2, LMP7, LMP10, tripeptidyl peptidase II (TPPII), bleomycin hydrolase (BLMH), leucine aminopeptidase 3 (LAP3), transporter associated with antigen processing (TAP) 1, TAP2,β2-microglobulin, TAP binding protein (tapasin), calnexin (CANX), calreticulin (CALR), protein disulfide isomerase family A member 2 (PDIA2), protein disulfide isomerase family A member 3 (PDIA3), ERp57, endoplasmic reticulum aminopeptidase (ERAP) 1, ERAP2, proteasome (prosome macropain) subunit althap (PSMA) type I (PSMA1), PSMA2, PSMA3, PSMA4, PSMA5, PSMA6, PSMA7, PSMA8, proteasome (prosome macropain) subunit beta (PSMB) type 1 (PSMB1), PSMB2, PSMB3, PSMB4, PSMB5, PSMB6, PSMB7, PSMB8, PSMB9, PSMB10, PSMB11, proteasome (prosome macropain) 26S subunit ATPase (PSMC) 1 (PSMC1); PSMC2, PSMC3, PSMC4, PSMC5, PSMC6, proteasome (prosome macropain) 26S subunit non-ATPase (PSMD) 1 (PSMD1), PSMD2, PSMD3, PSMD4, PSMD5, PSMD6, PSMD7, PSMD8, PSMD9, PSMD10, PSMD11, PSMD12, PSMD13, and PSMD14.

7. The method of claim 1, wherein said capture oligonucleotides further comprise a plurality of oligonucleotide subsets targeting killer-cell immunoglobulin-like receptor (KIR) polypeptide-encoding nucleic acids ("KIR oligo subsets"), and said method further comprises the step of assigning to the sample, based on the hybridization pattern, a KIR polypeptide phenotype; wherein each of said KIR oligo subsets comprises a set of overlapping oligonucleotides that cover every single nucleotide position in the mRNA sequences coding for the KIR polypeptides from 5' to 3' and are sequentially shifted by 1-5 nucleotides from the 5' end of the preceding overlapping oligonucleotide.

8. The method of claim 1, wherein said capture oligonucleotides further comprise a plurality of oligonucleotide subsets targeting blood group-determining polypeptide encoding nucleic acids ("blood group determining oligo subsets"), and said method further comprises the step of assigning to the sample, based on the hybridization pattern, a blood group phenotype;

wherein each of said blood group determining oligo subsets comprises a set of overlapping oligonucleotides that cover every single nucleotide position in the mRNA sequences coding for the blood group-determining polypeptides from 5' to 3' and are sequentially shifted by 1-5 nucleotides from the 5' end of the preceding overlapping oligonucleotide.

9. The method of claim 8, wherein said blood group determining polypeptides are selected from the group consisting ABO (ABO), Chido Rodgers (CH/RG), Colton (CO), Cromer (CROM), Diego (DI) (band 3), Dombrock (DO), Duffy (DARC), Gerbich (Ge), Gill (GIL), Globoside and Pk, H (H), I (I), Indian (IN), John Milton Hagen (JMH), Kell (KEL) and Kx(XK), Kidd (JK), Knops (KN), Landsteiner-Wiener (LW), Lewis (LE), Lutheran (LU), MNS (MNS, Glycophorins A, B and E), Ok (OK), Raph (RAPH), Rh(RH) and Rh-gp (RHAG), Scianna (SC), T/Tn, Xg (XG), and Yt (YT).

10. The method of claim 1, further comprising the step of deriving from the HLA tissue type assigned in step (c) donor/recipient transplant compatibility.

11. The method of claim 3, wherein said non-classical HLA oligo subsets comprise the sequences set forth in Table II.

12. The method of claim 5, wherein said accessory molecule oligo subsets comprise the sequences set forth in Table III.

13. The method of claim 7, wherein said KIR oligo subsets comprise the sequences set forth in Table IV.

14. The method of claim 8, wherein said blood group determining oligo subsets comprise the sequences set forth in Table V.

15. The method of claim 1, wherein the cDNA or cRNA in said sample was detectably labeled during its synthesis, and said detecting step (b) comprises detecting the detectably labeled cDNA or cRNA.

16. The method of claim 1, wherein said cDNA or cRNA-containing sample is obtained from a human subject.

17. The method of claim 16, further comprising the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, wherein the step is based on at least the classical HLA tissue type assigned in step (c).

18. The method of claim 16, further comprising the step of determining the likely response of said subject to a particular treatment regimen selected from the group consisting of: bone marrow transplantation, immunosuppressive regimen, antiviral drug regimen, antiviral drug resistance, antiretroviral drug regimen, and autoimmunity drug regimen, wherein the step is based on at least the classical HLA tissue type assigned in step (c).

19. The method of claim 16, further comprising the step of determining whether the subject is likely to develop antiretroviral drug resistance or cancer drug regimen resistance, wherein the step is based on at least the classical HLA tissue type assigned in step (c).

20. The method of claim 1, wherein said capture oligonucleotides further comprise at least one set of negative control oligonucleotides.

21. The method of claim 20, wherein said at least one set of negative control oligonucleotides comprises two or more of the nucleic acid sequences set forth in at least one of Tables VI-IX and Table X.

22. The method of claim 1, wherein said classical HLA oligo subsets collectively target all known classical HLA polypeptide-encoding nucleic acids.

23. The method of claim 3, wherein said non-classical HLA oligo subsets collectively target all known non-classical HLA polypeptide-encoding nucleic acids.

24. The method of claim 1, wherein said capture oligonucleotides are immobilized on a substrate.

25. The method of claim 1, wherein the detecting step (b) comprises the use of labeled detection probes, wherein the labeled detection probes hybridize to the cDNA or cRNA that has hybridized to the at least a portion of the plurality of capture oligonucleotides and are detectable such that the hybridization pattern of said cDNA or cRNA can be determined.

26. The method of claim 17, wherein the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, is further based on one or more of a non-classical HLA tissue type, an accessory molecule phenotype, a KIR polypeptide phenotype, and a blood group phenotype.

27. The method of claim 18, wherein the step of determining the likely response of said subject to a particular treatment regimen selected from the group consisting of: bone marrow transplantation, immunosuppressive regimen, antiviral drug regimen, antiviral drug resistance, antiretroviral drug regimen, and autoimmunity drug regimen is further based on one or more of a non-classical HLA tissue type, an accessory molecule phenotype, a KIR polypeptide phenotype, and a blood group phenotype.

28. A method for human leukocyte antigen (HLA) tissue typing, said method comprising:
(a) contacting a cDNA- or cRNA-containing sample under hybridization conditions with a plurality of capture oligonucleotides specific for HLA polypeptides, wherein said hybridization conditions facilitate hybridization of at least a portion of the plurality of capture oligonucleotides to complementary sequences present in the cDNA or CRNA;
(b) detecting a hybridization pattern for said cDNA or CRNA; and
(c) assigning to the sample, based on the hybridization pattern, an HLA tissue type;
wherein the capture oligonucleotides are from about 17 to about 60 nucleotides in length and each capture oligonucleotide with respect to its exact complement has a melting temperature of about 64 degrees Celsius;
wherein said capture oligonucleotides comprise subsets of oligonucleotides that collectively target classical HLA polypeptide-encoding nucleic acids ("classical HLA oligo subsets"), each classical HLA oligo subset targeting a different classical HLA polypeptide-encoding nucleic acid; and
wherein each of said classical HLA oligo subsets comprises a set of overlapping oligonucleotides that cover every single nucleotide position in each of the full-length coding regions of mRNA sequences coding for the classical HLA polypeptides from 5' to 3' and are sequentially shifted by 1-5 nucleotides from the 5' end of the preceding overlapping oligonucleotide;
wherein said cDNA or cRNA-containing sample is obtained from a human subject;
wherein the method further comprising the step of determining whether the human subject is likely to develop antiretroviral drug resistance or cancer drug regimen resistance, the step being based on at least the classical HLA tissue type assigned in step (c); and
wherein the step of determining whether the subject is likely to develop antiretroviral drug resistance or cancer drug regimen resistance is further based on one or more of a non-classical HLA tissue type, an accessory molecule phenotype, a KIR polypeptide phenotype, and a blood group phenotype.

29. The method of claim 28, wherein said classical HLA polypeptide-encoding nucleic acids encode HLA polypeptides selected from the group consisting of HLA-A, HLA-B, HLA-C, HLA-DR, HLA-DP, and HLA-DQ.

30. The method of claim 28, wherein said classical HLA oligo subsets comprise the sequences set forth in Table I or the normal (indicated by "HPN"), extended (indicated by "HPE") and truncated (indicated by "HPT") sequences set forth in Table X.

31. The method of claim 28, wherein said capture oligonucleotides further comprise a plurality of oligonucleotide subsets that collectively targets non-classical HLA polypeptide-encoding nucleic acids ("non-classical HLA oligo subsets"), each non-classical HLA oligo subset targeting a different non-classical HLA polypeptide-encoding nucleic acid;
wherein each of said non-classical HLA oligo subsets comprises a set of overlapping oligonucleotides that cover every single nucleotide position in the mRNA sequences coding for the non-classical HLA polypeptides from 5' to 3' and are sequentially shifted by 1-5 nucleotides from the 5' end of the preceding overlapping oligonucleotide.

32. The method of claim 31, wherein said non-classical HLA polypeptide-encoding nucleic acids encode HLA polypeptides selected from the group consisting of HLA-E, HLA-F, HLA-G, DM, DO and MIC.

33. The method of claim 28, wherein said capture oligonucleotides further comprise a plurality of oligonucleotide subsets that collectively targets nucleic acids encoding accessory molecules important in HLA-linked peptide presentation and/or processing ("accessory molecule oligo subsets"), and said method further comprises the step of assigning to the sample, based on the hybridization pattern, an accessory molecule phenotype;

wherein each of said accessory molecule oligo subsets comprises a set of overlapping oligonucleotides that cover every single nucleotide position in the mRNA sequences coding for the accessory molecules from 5' to 3' and are sequentially shifted by 1-5 nucleotides from the 5' end of the preceding overlapping oligonucleotide.

34. The method of claim 33, wherein said accessory molecules are selected from the group consisting of LMP2, LMP7, LMP10, tripeptidyl peptidase II (TPPII), bleomycin hydrolase (BLMH), leucine aminopeptidase 3 (LAP3), transporter associated with antigen processing (TAP) 1, TAP2,β2-microglobulin, TAP binding protein (tapasin), calnexin (CANX), calreticulin (CALR), protein disulfide isomerase family A member 2 (PDIA2), protein disulfide isomerase family A member 3 (PDIA3), ERp57, endoplasmic reticulum aminopeptidase (ERAP) 1, ERAP2, proteasome (prosome macropain) subunit althap (PSMA) type I (PSMA1), PSMA2, PSMA3, PSMA4, PSMA5, PSMA6, PSMA7, PSMA8, proteasome (prosome macropain) subunit beta (PSMB) type 1 (PSMB1), PSMB2, PSMB3, PSMB4, PSMB5, PSMB6, PSMB7, PSMB8, PSMB9, PSMB10, PSMB11, proteasome (prosome macropain) 26S subunit ATPase (PSMC) 1 (PSMC1); PSMC2, PSMC3, PSMC4, PSMC5, PSMC6, proteasome (prosome macropain) 26S subunit non-ATPase (PSMD) 1 (PSMD1), PSMD2, PSMD3, PSMD4, PSMD5, PSMD6, PSMD7, PSMD8, PSMD9, PSMD10, PSMD11, PSMD12, PSMD13, and PSMD14.

35. The method of claim 28, wherein said capture oligonucleotides further comprise a plurality of oligonucleotide subsets targeting killer-cell immunoglobulin-like receptor (KIR) polypeptide-encoding nucleic acids ("KIR oligo subsets"), and said method further comprises the step of assigning to the sample, based on the hybridization pattern, a KIR polypeptide phenotype; wherein each of said KIR oligo subsets comprises a set of overlapping oligonucleotides that cover every single nucleotide position in the mRNA sequences coding for the KIR polypeptides from 5' to 3' and are sequentially shifted by 1-5 nucleotides from the 5' end of the preceding overlapping oligonucleotide.

36. The method of claim 28, wherein said capture oligonucleotides further comprise a plurality of oligonucleotide subsets targeting blood group-determining polypeptide encoding nucleic acids ("blood group determining oligo subsets"), and said method further comprises the step of assigning to the sample, based on the hybridization pattern, a blood group phenotype;
wherein each of said blood group determining oligo subsets comprises a set of overlapping oligonucleotides that cover every single nucleotide position in the mRNA sequences coding for the blood group-determining polypeptides from 5' to 3' and are sequentially shifted by 1-5 nucleotides from the 5' end of the preceding overlapping oligonucleotide.

37. The method of claim 36, wherein said blood group determining polypeptides are selected from the group consisting ABO (ABO), Chido Rodgers (CH/RG), Colton (CO), Cromer (CROM), Diego (DI) (band 3), Dombrock (DO), Duffy (DARC), Gerbich (Ge), Gill (GIL), Globoside and Pk, H (H), I (I), Indian (IN), John Milton Hagen (JMH), Kell (KEL) and Kx(XK), Kidd (JK), Knops (KN), Landsteiner-Wiener (LW), Lewis (LE), Lutheran (LU), MNS (MNS, Glycophorins A, B and E), Ok (OK), Raph (RAPH), Rh(RH) and Rh-gp (RHAG), Scianna (SC), T/Tn, Xg (XG), and Yt (YT).

38. The method of claim 28, further comprising the step of deriving from the HLA tissue type assigned in step (c) donor/recipient transplant compatibility.

39. The method of claim 31, wherein said non-classical HLA oligo subsets comprise the sequences set forth in Table II.

40. The method of claim 33, wherein said accessory molecule oligo subsets comprise the sequences set forth in Table III.

41. The method of claim 35, wherein said KIR oligo subsets comprise the sequences set forth in Table IV.

42. The method of claim 36, wherein said blood group determining oligo subsets comprise the sequences set forth in Table V.

43. The method of claim 28, wherein the cDNA or cRNA in said sample was detectably labeled during its synthesis, and said detecting step (b) comprises detecting the detectably labeled cDNA or cRNA.

44. The method of claim 28, further comprising the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, wherein the step is based on at least the classical HLA tissue type assigned in step (c).

45. The method of claim 28, further comprising the step of determining the likely response of said subject to a particular treatment regimen selected from the group consisting of: bone marrow transplantation, immunosuppressive regimen, antiviral drug regimen, antiviral drug resistance, antiretroviral drug regimen, and autoimmunity drug regimen, wherein the step is based on at least the classical HLA tissue type assigned in step (c).

46. The method of claim 28, wherein said capture oligonucleotides further comprise at least one set of negative control oligonucleotides.

47. The method of claim 46, wherein said at least one set of negative control oligonucleotides comprises two or more of the nucleic acid sequences set forth in at least one of Tables VI-IX and Table X.

48. The method of claim 28, wherein said classical HLA oligo subsets collectively target all known classical HLA polypeptide-encoding nucleic acids.

49. The method of claim 31, wherein said non-classical HLA oligo subsets collectively target all known non-classical HLA polypeptide-encoding nucleic acids.

50. The method of claim 28, wherein said capture oligonucleotides are immobilized on a substrate.

51. The method of claim 28, wherein the detecting step (b) comprises the use of labeled detection probes, wherein the labeled detection probes hybridize to the cDNA or cRNA that has hybridized to the at least a portion of the plurality of capture oligonucleotides and are detectable such that the hybridization pattern of said cDNA or cRNA can be determined.

52. The method of claim 44, wherein the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, is further based on one or more of a non-classical HLA tissue type, an accessory molecule phenotype, a KIR polypeptide phenotype, and a blood group phenotype.

53. The method of claim 52, wherein the step of determining the likely response of said subject to a particular treatment regimen selected from the group consisting of:
bone marrow transplantation, immunosuppressive regimen, antiviral drug regimen, antiviral drug resistance, antiretroviral drug regimen, and autoimmunity drug regimen is further based on one or more of a non-classical HLA tissue type, an accessory molecule phenotype, a KIR polypeptide phenotype, and a blood group phenotype.

54. A method for human leukocyte antigen (HLA) tissue typing, said method comprising:
(a) contacting a cDNA- or cRNA-containing sample under hybridization conditions with a plurality of capture oligonucleotides specific for HLA polypeptides, wherein said hybridization conditions facilitate hybridization of at least a portion of the plurality of capture oligonucleotides to complementary sequences present in the cDNA or cRNA;
(b) detecting a hybridization pattern for said cDNA or cRNA; and
(c) assigning to the sample, based on the hybridization pattern, an HLA tissue type;
wherein the capture oligonucleotides are from about 17 to about 60 nucleotides in length and each capture oligonucleotide with respect to its exact complement has a melting temperature of about 64 degrees Celsius;
wherein said capture oligonucleotides comprise subsets of oligonucleotides that collectively target classical HLA polypeptide-encoding nucleic acids ("classical HLA oligo subsets"), each classical HLA oligo subset targeting a different classical HLA polypeptide-encoding nucleic acid;
wherein each of said classical HLA oligo subsets comprises a set of overlapping oligonucleotides that cover every single nucleotide position in each of the full-length coding regions of mRNA sequences coding for the classical HLA polypeptides from 5' to 3' and are sequentially shifted by 1-5 nucleotides from the 5' end of the preceding overlapping oligonucleotide;
wherein said capture oligonucleotides further comprise at least one set of negative control oligonucleotides; and
wherein said at least one set of negative control oligonucleotides comprises two or more of the nucleic acid sequences set forth in at least one of Tables VI-IX and Table X.

55. The method of claim 54, wherein said capture oligonucleotides further comprise a plurality of oligonucleotide subsets that collectively targets non-classical HLA polypeptide-encoding nucleic acids ("non-classical HLA oligo subsets"), each non-classical HLA oligo subset targeting a different non-classical HLA polypeptide-encoding nucleic acid;
wherein each of said non-classical HLA oligo subsets comprises a set of overlapping oligonucleotides that cover every single nucleotide position in the mRNA sequences coding for the non-classical HLA polypeptides from 5' to 3' and are sequentially shifted by 1-5 nucleotides from the 5' end of the preceding overlapping oligonucleotide.

56. The method of claim 55, wherein said non-classical HLA polypeptide-encoding nucleic acids encode HLA polypeptides selected from the group consisting of HLA-E, HLA-F, HLA-G, DM, DO and MIC.

57. The method of claim 54, wherein said capture oligonucleotides further comprise a plurality of oligonucleotide subsets that collectively targets nucleic acids encoding accessory molecules important in HLA-linked peptide presentation and/or processing ("accessory molecule oligo subsets"), and said method further comprises the step of assigning to the sample, based on the hybridization pattern, an accessory molecule phenotype;
wherein each of said accessory molecule oligo subsets comprises a set of overlapping oligonucleotides that cover every single nucleotide position in the mRNA sequences coding for the accessory molecules from 5' to 3' and are sequentially shifted by 1-5 nucleotides from the 5' end of the preceding overlapping oligonucleotide.

58. The method of claim 57, wherein said accessory molecules are selected from the group consisting of LMP2, LMP7, LMP10, tripeptidyl peptidase II (TPPII), bleomycin hydrolase (BLMH), leucine aminopeptidase 3 (LAP3), transporter associated with antigen processing (TAP) 1, TAP2,β2-microglobulin, TAP binding protein (tapasin), calnexin (CANX), calreticulin (CALR), protein disulfide isomerase family A member 2 (PDIA2), protein disulfide isomerase family A member 3 (PDIA3), ERp57, endoplasmic reticulum aminopeptidase (ERAP) 1, ERAP2, proteasome (prosome macropain) subunit althap (PSMA) type I (PSMA1), PSMA2, PSMA3, PSMA4, PSMA5, PSMA6, PSMA7, PSMA8, proteasome (prosome macropain) subunit beta (PSMB) type 1 (PSMB1), PSMB2, PSMB3, PSMB4, PSMB5, PSMB6, PSMB7, PSMB8, PSMB9, PSMB10, PSMB11, proteasome (prosome macropain) 26S subunit ATPase (PSMC) 1 (PSMC1); PSMC2, PSMC3, PSMC4, PSMC5, PSMC6, proteasome (prosome macropain) 26S subunit non-ATPase (PSMD) 1 (PSMD1), PSMD2, PSMD3, PSMD4, PSMD5, PSMD6, PSMD7, PSMD8, PSMD9, PSMD10, PSMD11, PSMD12, PSMD13, and PSMD14.

59. The method of claim 54, wherein said capture oligonucleotides further comprise a plurality of oligonucleotide subsets targeting killer-cell immunoglobulin-like receptor (KIR) polypeptide -encoding nucleic acids ("KIR oligo subsets"), and said method further comprises the step of assigning to the sample, based on the hybridization pattern, a KIR polypeptide phenotype; wherein each of said KIR oligo subsets comprises a set of overlapping oligonucleotides that cover every single nucleotide position in the mRNA sequences coding for the KIR polypeptides from 5' to 3' and are sequentially shifted by 1-5 nucleotides from the 5' end of the preceding overlapping oligonucleotide.

60. The method of claim 54, wherein said capture oligonucleotides further comprise a plurality of oligonucleotide subsets targeting blood group-determining polypeptide encoding nucleic acids ("blood group determining oligo subsets"), and said method further comprises the step of assigning to the sample, based on the hybridization pattern, a blood group phenotype;
wherein each of said blood group determining oligo subsets comprises a set of overlapping oligonucleotides that cover every single nucleotide position in the mRNA sequences coding for the blood group-determining polypeptides from 5' to 3' and are sequentially shifted by 1-5 nucleotides from the 5' end of the preceding overlapping oligonucleotide.

61. The method of claim 60, wherein said blood group determining polypeptides are selected from the group consisting ABO (ABO), Chido Rodgers (CH/RG), Colton (CO), Cromer (CROM), Diego (DI) (band 3), Dombrock (DO), Duffy (DARC), Gerbich (Ge), Gill (GIL), Globoside and Pk, H (H), I (I), Indian (IN), John Milton Hagen (JMH), Kell (KEL) and Kx(XK), Kidd (JK), Knops (KN), Landsteiner-Wiener (LW), Lewis (LE), Lutheran (LU), MNS (MNS, Glycophorins A, B and E), Ok (OK), Raph (RAPH), Rh(RH) and Rh-gp (RHAG), Scianna (SC), T/Tn, Xg (XG), and Yt (YT).

62. The method of claim 54, further comprising the step of deriving from the HLA tissue type assigned in step (c) donor/recipient transplant compatibility.

63. The method of claim 55, wherein said non-classical HLA oligo subsets comprise the sequences set forth in Table II.

64. The method of claim 57, wherein said accessory molecule oligo subsets comprise the sequences set forth in Table III.

65. The method of claim 59, wherein said KIR oligo subsets comprise the sequences set forth in Table IV.

66. The method of claim 60, wherein said blood group determining oligo subsets comprise the sequences set forth in Table V.

67. The method of claim 54, wherein the cDNA or cRNA in said sample was detectably labeled during its synthesis, and said detecting step (b) comprises detecting the detectably labeled cDNA or cRNA.

68. The method of claim 54, wherein said cDNA or cRNA-containing sample is obtained from a human subject.

69. The method of claim 68, further comprising the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, wherein the step is based on at least the classical HLA tissue type assigned in step (c).

70. The method of claim 69, further comprising the step of determining the likely response of said subject to a particular treatment regimen selected from the group consisting of: bone marrow transplantation, immunosuppressive regimen, antiviral drug regimen, antiviral drug resistance, antiretroviral drug regimen, and autoimmunity drug regimen, wherein the step is based on at least the classical HLA tissue type assigned in step (c).

71. The method of claim 69, further comprising the step of determining whether the subject is likely to develop antiretroviral drug resistance or cancer drug regimen resistance, wherein the step is based on at least the classical HLA tissue type assigned in step (c).

72. The method of claim 54, wherein the detecting step (b) comprises the use of labeled detection probes, wherein the labeled detection probes hybridize to the cDNA or cRNA that has hybridized to the at least a portion of the plurality of capture oligonucleotides and are detectable such that the hybridization pattern of said cDNA or cRNA can be determined.

73. The method of claim 54, wherein said classical HLA oligo subsets collectively target all known classical HLA polypeptide-encoding nucleic acids.

74. The method of claim 55, wherein said non-classical HLA oligo subsets collectively target all known non-classical HLA polypeptide-encoding nucleic acids.

75. The method of claim 54, wherein said capture oligonucleotides are immobilized on a substrate.

76. The method of claim 69, wherein the step of diagnosing or predicting the likelihood of an HLA-linked genetic defect, disease, inadequate or undesirable response to a vaccine, biologic treatment (recombinant protein, biosimilar or equivalent), or infectious organism, or condition in said subject, is further based on one or more of a non-classical HLA tissue type, an accessory molecule phenotype, a KIR polypeptide phenotype, and a blood group phenotype.

77. The method of claim 76, wherein the step of determining the likely response of said subject to a particular treatment regimen selected from the group consisting of:

bone marrow transplantation, immunosuppressive regimen, antiviral drug regimen, antiviral drug resistance, antiretroviral drug regimen, and autoimmunity drug regimen is further based on one or more of a non-classical HLA tissue type, an accessory molecule phenotype, a KIR polypeptide phenotype, and a blood group phenotype.

\* \* \* \* \*